(12) United States Patent
McNeel et al.

(10) Patent No.: US 10,881,719 B2
(45) Date of Patent: Jan. 5, 2021

(54) COMBINATORIAL ANDROGEN DEPRIVATION WITH AN ANDROGEN RECEPTOR VACCINE

(71) Applicant: Wisconsin Alumni Research Foundation, Madison, WI (US)

(72) Inventors: Douglas McNeel, Madison, WI (US); Brian Olson, Madison, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 180 days.

(21) Appl. No.: 15/619,140

(22) Filed: Jun. 9, 2017

(65) Prior Publication Data

US 2017/0354725 A1 Dec. 14, 2017

Related U.S. Application Data

(60) Provisional application No. 62/347,646, filed on Jun. 9, 2016.

(51) Int. Cl.
| | |
|---|---|
| *A61K 38/09* | (2006.01) |
| *A61K 39/00* | (2006.01) |
| *A61K 38/08* | (2019.01) |
| *C07K 16/28* | (2006.01) |
| *C07K 16/30* | (2006.01) |

(52) U.S. Cl.
CPC ...... *A61K 39/001102* (2018.08); *A61K 38/08* (2013.01); *A61K 38/09* (2013.01); *A61K 39/0011* (2013.01); *C07K 16/2818* (2013.01); *C07K 16/2827* (2013.01); *C07K 16/3069* (2013.01); *A61K 2039/53* (2013.01); *A61K 2039/545* (2013.01); *C07K 2317/76* (2013.01)

(58) Field of Classification Search
CPC .... A61K 39/0011; A61K 38/09; A61K 38/08; C07K 16/3069
USPC .................................................... 424/174.1
See application file for complete search history.

(56) References Cited

U.S. PATENT DOCUMENTS

| 7,910,565 B2 | 3/2011 | McNeel et al. |
| 8,962,590 B2 | 2/2015 | McNeel et al. |
| 2008/0063654 A1 | 3/2008 | McNeel et al. |

OTHER PUBLICATIONS

PubChem_Nilutannide (Mar. 5, 2005, pp. 1-2).*
Arlen, et al., Antiandrogen, vaccine and combination therapy in patients with nonmetastatic hormone refractory prostate cancer, Journal of Urology, vol. 174, No. 2, Aug. 2005 (Aug. 2005), pp. 539-546.
Tse, et al., From Bench to Bedside: Immunotherapy for Prostate Cancer, Biomed Research International, 2014, XP002773771, ISSN: 2314-6133, pp. 1-12.
International Search Report and Written Opinion from PCT/US2017/036843, dated Oct. 2, 2017, 16 pages.
Akins EJ, et al. In situ vaccination combined with androgen ablation and regulatory T-cell depletion reduces castration-resistant tumor burden in prostate-specific pten knockout mice. Cancer Res. 2010;70:3473-82.
Antonarakis ES, et al. AR-V7 and resistance to enzalutamide and abiraterone in prostate cancer. N Engl J Med. 2014;371:1028-38.
Antonarakis ES, et al. Sequencing of Sipuleucel-T and Androgen Deprivation Therapy in Men with Hormone-Sensitive Biochemically-Recurrent Prostate Cancer: A Phase II Randomized Trial. Clin Cancer Res. 2016.
Ardiani A, et al. Combination therapy with a second-generation androgen receptor antagonist and a metastasis vaccine improves survival in a spontaneous prostate cancer model. Clin Cancer Res. 2013;19:6205-18.
Ardiani A, et al. Androgen deprivation therapy sensitizes prostate cancer cells to T-cell killing through androgen receptor dependent modulation of the apoptotic pathway. Oncotarget. 2014;5:9335-48.
Beattie BJ, et al. Pharmacokinetic assessment of the uptake of 16beta-18F-fluoro-5alpha-dihydrotestosterone (FDHT) in prostate tumors as measured by PET. J Nucl Med. 2010;51:183-92.
Chakraborty M, et al. Irradiation of tumor cells up-regulates Fas and enhances CTL lytic activity and CTL adoptive immunotherapy. J Immunol. 2003;170:6338-47.
Chakraborty M, et al. External beam radiation of tumors alters phenotype of tumor cells to render them susceptible to vaccine-mediated T-cell killing. Cancer Res. 2004;64:4328-37.
Colluru VT, et al. Preclinical and clinical development of DNA vaccines for prostate cancer. Urol Oncol. 2016;34:193-204.
Demaria S, et al. Immune-mediated inhibition of metastases after treatment with local radiation and CTLA-4 blockade in a mouse model of breast cancer. Clin Cancer Res. 2005;11:728-34.
Disselhorst JA, et al. Image-quality assessment for several positron emitters using the NEMA NU 4-2008 standards in the Siemens Inveon small-animal PET scanner. J Nucl Med. 2010;51:610-7.
Drake CG, et al. Androgen ablation mitigates tolerance to a prostate/prostate cancer-restricted antigen. Cancer cell. 2005;7:239-49.
Drake CG, et al. Metastatic castration-resistant prostate cancer: new therapies, novel combination strategies and implications for immunotherapy. Oncogene. 2014;33:5053-64.
Ellis L, et al. Development of a castrate resistant transplant tumor model of prostate cancer. Prostate. 2012;72:587-91.
Fueger BJ, et al. Impact of animal handling on the results of 18F-FDG PET studies in mice. J Nucl Med. 2006;47:999-1006.

(Continued)

*Primary Examiner* — Yan Xiao
(74) *Attorney, Agent, or Firm* — Quarles & Brady LLP

(57) ABSTRACT

It is disclosed herein methods of treating prostate cancer comprising administering to the subject the combination of androgen deprivation therapy (ADT) and a vaccine directed against the androgen receptor or a fragment of the androgen receptor. Also disclosed are methods of increasing the efficacy of androgen deprivation therapy in a subject with prostate cancer comprising administering to the subject an effective amount of a vaccine against the androgen receptor or fragments thereof wherein the method inhibits, delays or reduces the growth of the prostate cancer and/or the development of castration-resistant prostate cancer.

19 Claims, 36 Drawing Sheets
(23 of 36 Drawing Sheet(s) Filed in Color)

Specification includes a Sequence Listing.

(56) References Cited

OTHER PUBLICATIONS

Gameiro SR, et al. Radiation-induced immunogenic modulation of tumor enhances antigen processing and calreticulin exposure, resulting in enhanced T-cell killing. Oncotarget. 2013;5:403-16.
Gannon PO, et al. Characterization of the intra-prostatic immune cell infiltration in androgen-deprived prostate cancer patients. Journal of immunological methods. 2009;348:9-17.
Gan L, et al. Inhibition of the androgen receptor as a novel mechanism of taxol chemotherapy in prostate cancer. Cancer Res. 2009;69:8386-94.
Garnett CT, et al. Sublethal irradiation of human tumor cells modulates phenotype resulting in enhanced killing by cytotoxic T lymphocytes. Cancer Res. 2004;64:7985-94.
Graff JN, et al. Early evidence of anti-PD-1 activity in enzalutamide-resistant prostate cancer. Oncotarget. 2016.
Gregory CW, et al. Androgen receptor expression in androgen-independent prostate cancer is associated with increased expression of androgen-regulated genes. Cancer Res. 1998;58:5718-24.
Golden EB, et al. Local radiotherapy and granulocyte-macrophage colony-stimulating factor to generate abscopal responses in patients with metastatic solid tumours: a proof-of-principle trial. The lancet oncology. 2015;16:795-803.
Harris TJ, et al. Radiotherapy augments the immune response to prostate cancer in a time-dependent manner. Prostate. 2008;68:1319-29.
Hodge JW, et al. The tipping point for combination therapy: cancer vaccines with radiation, chemotherapy, or targeted small molecule inhibitors. Semin Oncol. 2012;39:323-39.
Hornberg E, et al. Expression of androgen receptor splice variants in prostate cancer bone metastases is associated with castration-resistance and short survival. PloS one. 2011;6:e19059.
Jemal A. et al., Cancer Statistics, 2005 (2005) CA Cancer J Clin, 55:10-30.
Kissick HT, et al. Androgens alter T-cell immunity by inhibiting T-helper 1 differentiation. Proc Natl Acad Sci U S A. 2014;111:9887-92.
Koh YT, et al. Androgen ablation augments prostate cancer vaccine immunogenicity only when applied after immunization. Prostate. 2009.
Madan RA, et al. Analysis of overall survival in patients with nonmetastatic castration-resistant prostate cancer treated with vaccine, nilutamide, and combination therapy. Clin Cancer Res. 2008;14:4526-31.
Mcneel DG, et al. Phase I trial of tremelimumab in combination with short-term androgen deprivation in patients with PSA-recurrent prostate cancer. Cancer Immunol Immunother. 2012;61:1137-47.
Mercader M, et al. T cell infiltration of the prostate induced by androgen withdrawal in patients with prostate cancer. Proc Natl Acad Sci U S A. 2001;98:14565-70.
Mercader M, et al. Early effects of pharmacological androgen deprivation in human prostate cancer. BJU Int. 2007;99:60-7.
Morse MD, et al. Prostate Cancer Patients Treated with Androgen Deprivation Therapy Develop Persistent Changes in Adaptive Immune Responses. Human immunology. 2010;71:496-504.
Morse MD, et al. T cells localized to the androgen-deprived prostate are TH1 and TH17 biased. Prostate. 2012;72:1239-47.
Oefelein et al., 1997, J Urol, 158:1460-1465.
Olson BM, et al. CD8+ T cells specific for the androgen receptor are common in patients with prostate cancer and are able to lyse prostate tumor cells. Cancer Immunol Immunother. 2011;60:781-92.
Olson BM, et al. The androgen receptor: a biologically relevant vaccine target for the treatment of prostate cancer. Cancer Immunol Immunother. 2013;62:585-96.
Pu Y, et al. Androgen receptor antagonists compromise T cell response against prostate cancer leading to early tumor relapse. Science translational medicine. 2016;8:333ra47.
Rekoske, B.T., et al. (2015). "PD-1 or PD-L1 Blockade Restores Antitumor Efficacy Following SSX2 Epitope-Modified DNA Vaccine Immunization." Cancer Immunol Res. 3:946-55.
Roden AC, et al. Augmentation of T cell levels and responses induced by androgen deprivation. J Immunol. 2004;173:6098-108.
Rowe SP, et al. PSMA-Based [(18)F]DCFPyL PET/CT Is Superior to Conventional Imaging for Lesion Detection in Patients with Metastatic Prostate Cancer. Molecular imaging and biology : MIB : the official publication of the Academy of Molecular Imaging. 2016;18:411-9.
Shen YC, et al. Combining androgen deprivation with immune checkpoint blockade delays the development of castration resistance in a murine model of prostate cancer. AACR 106th Annual Meeting 2015; 2015; Philadelphia, PA.
Slovin SF, et al. Ipilimumab alone or in combination with radiotherapy in metastatic castration-resistant prostate cancer: results from an open-label, multicenter phase I/II study. Ann Oncol. 2013;24:1813-21.
Small EJ, et al. A Randomized Phase II Trial of Sipuleucel-T with Concurrent versus Sequential Abiraterone Acetate plus Prednisone in Metastatic Castration-Resistant Prostate Cancer. Clin Cancer Res. 2015;21:3862-9.
Smith HA, et al. Expression and Immunotherapeutic Targeting of the SSX Family of Cancer-Testis Antigens in Prostate Cancer. Cancer Res. 2011;71:6785-95.
Spratt DE, et al. Androgen Receptor Upregulation Mediates Radioresistance after Ionizing Radiation. Cancer Res. 2015;75:4688-96.
Sweeney CJ, et al. Chemohormonal Therapy in Metastatic Hormone-Sensitive Prostate Cancer. The New England journal of medicine. 2015;373:737-46.
Valkenburg KC, Williams BO. Mouse models of prostate cancer. Prostate cancer. 2011:895238.
Wang S, et al. Prostate-specific deletion of the murine Pten tumor suppressor gene leads to metastatic prostate cancer. Cancer cell. 2003;4:209-21.
Watson PA, et al. Constitutively active androgen receptor splice variants expressed in castration-resistant prostate cancer require full-length androgen receptor. Proc Natl Acad Sci U S A. 2010;107:16759-65.
Weichert JP, et al. Alkylphosphocholine analogs for broad-spectrum cancer imaging and therapy. Science translational medicine. 2014;6:240ra75.
Yu Z, et al. Rapid induction of androgen receptor splice variants by androgen deprivation in prostate cancer. Clin Cancer Res. 2014;20:1590-600.
Zhu ML, et al. Tubulin-targeting chemotherapy impairs androgen receptor activity in prostate cancer. Cancer Res. 2010;70:7992-8002.
Olson B., Not just a pharmacological target: Preclinical studies and clinical development of a DNA vaccine targeting the androgen receptor, PCF Coffey-Holden Prostate Cancer Academy, Jun. 27, 2014.
Olson, B. et al., Androgen deprivation increases androgen receptor (AR) expression and enhances tumor cell susceptibility to AR-specific T-cell responses, PCF Retreat, Oct. 24, 2014.
Gulley, et al., Phase III Trial of PROSTVAC in Asymptomatic or Minimally Symptomatic Metastatic Castration-Resistant Prostate Cancer. J Clin Oncol, 2019, 37 (13), pp. 1051-1061.

* cited by examiner

D.

C.

FIGS. 12G-12I
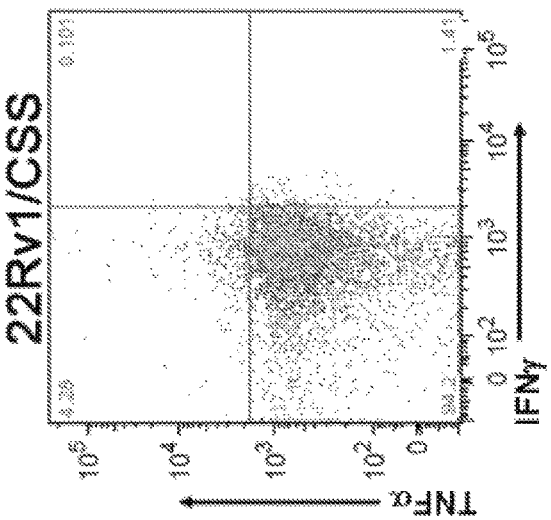
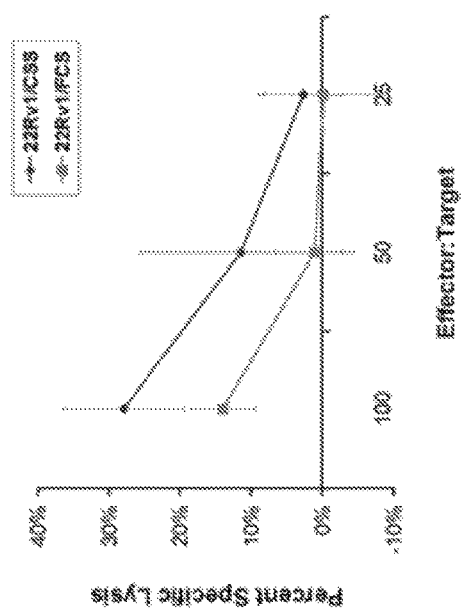
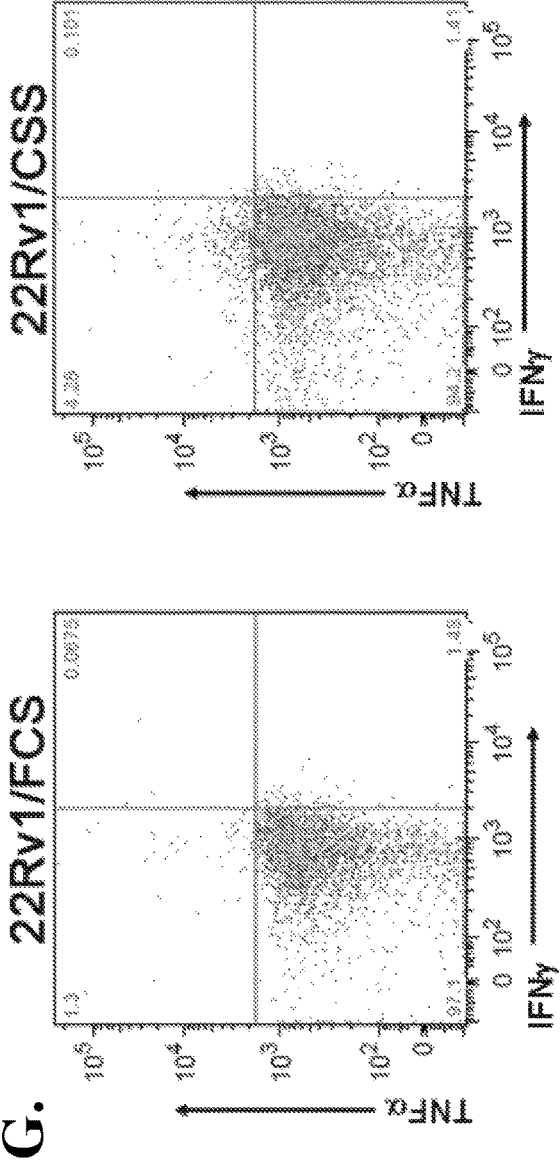
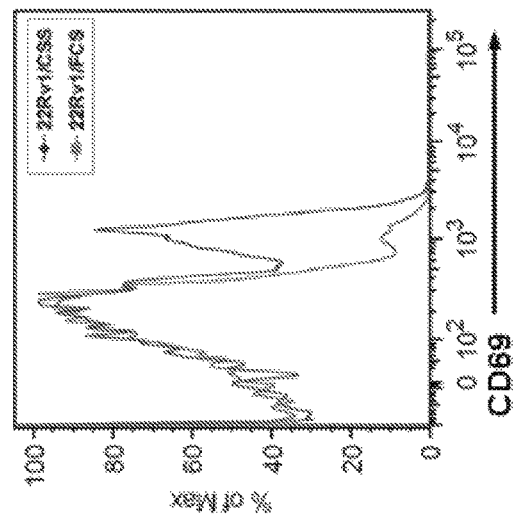

SEQUENCE LISTING

```
<160> NUMBER OF SEQ ID NOS: 20

<210> SEQ ID NO 1
<211> LENGTH: 10070
<212> TYPE: DNA
<213> ORGANISM: Homo sapiens

<400> SEQUENCE: 1
gcggagagaa ccctctgttt tcccccactc tctctccacc tcctcctgcc ttccccaccc      60
cgagtgcgga gccagagatc aaaagatgaa aaggcagtca ggtcttcagt agccaaaaaa     120
caaaacaaac aaaaacaaaa aagccgaaat aaaagaaaaa gataataact cagttcttat     180
```

-continued

```
ttgcacctac ttcagtggac actgaatttg aaggtggag attttgttt ttttcttta         240
agatctgggc atcttttgaa tctacccttc aagtattaag agacagactg tgagcctagc      300
agggcagatc ttgtccaccg tgtgtcttct tctgcacgag actttgaggc tgtcagagcg      360
cttttttgcgt ggttgctccc gcaagttttcc ttctctggag cttccgcag gtgggcagct     420
agctgcagcg actaccgcat catcacagcc tgttgaactc ttctgagcaa gagaagggga     480
ggcggggtaa gggaagtagg tggaagattc agccaagctc aaggatggaa gtgcagttag     540
ggctgggaag ggtctaccct cggccgccgt ccaagaccta ccgaggagct ttccagaatc     600
tgttccagag cgtgcgcgaa gtgatccaga acccgggccc caggcaccca gaggccgcga    660
gcgcagcacc tcccggcgcc agtttgctgc tgctgcagca gcagcagcag cagcagcagc    720
agcagcagca gcagcagcag cagcagcagc agcagcagca gcaagagact agccccaggc   780
agcagcagca gcagcagggt gaggatggtt ctccccaagc ccatcgtaga ggccccacag    840
gctacctggt cctggatgag aacagcaac cttcacagcc gcagtcggcc ctggagtgcc     900
accccgagag aggttgcgtc ccagagcctg agccgccgt ggccgccagc aaggggctgc    960
cgcagcagct gccagcacct ccggacgagg atgactcagc tgccccatcc acgttgtccc  1020
tgctgggccc cactttcccc ggcttaagca gctgctccgc tgaccttaaa gacatcctga   1080
gcgaggccag caccatgcaa ctccttcagc aacagcagca ggaagcagta tccgaaggca   1140
gcagcagcgg gagagcgagg gaggcctcgg gggctcccac ttcctccaag gacaattact   1200
tagggggcac ttcgaccatt tctgacaacg ccaaggagtt gtgtaaggca gtgtcggtgt   1260
ccatgggcct gggtgtggag gcgttggagc atctgagtcc aggggaacag cttcgggggg   1320
attgcatgta cgccccactt ttgggagttc caccgctgt gcgtcccact ccttgtgccc   1380
cattggccga atgcaaaggt tctctgctag acgacgcgc aggcaagagc actgaagata   1440
ctgctgagta ttccccttc aagggaggtt acaccaaagg gctagaaggc gagagcctag   1500
gctgctctgg cagcgctgca gcagggagct ccgggacact tgaactgccg tctaccctgt  1560
ctctctacaa gtccggagca ctggacgagg cagctgcgta ccagagtcgc gactactaca  1620
actttccact ggctctggcc ggaccgccgc cccctccgcc gctcccccat ccccacgctc  1680
gcatcaagct ggagaacccg ctggactacg cagcgcctg ggcggctgcg gcggcgcagt   1740
gccgctatgg ggacctggcg agcctgcatg cgcgggtgc agcgggaccc ggttctgggt   1800
caccctcagc cgccgcttcc tcatcctggc acactctctt cacagccgaa gaaggccagt  1860
tgtatggacc gtgtgtggt ggtggggggtg gtggcggcgg cggcggcggc ggcggcggcg   1920
gcggcggcgg cggcggcggc ggcgaggcgg gagctgtagc ccctcacggc tacactcggc  1980
cccctcaggg gctggcggc caggaaagcg acttcaccgc acctgatgtg tggtaccctg   2040
gcggcatggt gagcagagtg ccctatccca gtcccacttg tgtcaaaagc gaaatgggcc   2100
cctggatgga tagctactcc ggaccttacg gggacatgcg tttggagact gccagggacc   2160
atgttttgcc cattgactat tactttccac cccagaagac ctgcctgatc tgtggagatg   2220
aagcttctgg gtgtcactat ggagctctca catgtggaag ctgcaaggtc ttcttcaaaa    2280
gagccgctga agggaaacag aagtacctgt gcgccagcag aaatgattgc actattgata    2340
aattccgaag gaaaaattgt ccatcttgtc gtcttcggaa atgttatgaa gcagggatga    2400
ctctggggagc ccggaagctg aagaaacttg gtaatctgaa actacaggag aaggagagg    2460
cttccagcac caccagcccc actgaggaga caacccagaa gctgacagtg tcacacattg   2520
aaggctatga atgtcagccc atctttctga atgtcctgga agccattgag ccaggtgtag    2580
```

```
tgtgtgctgg acacgacaac aaccagcccg actcctttgc agccttgctc tctagcctca   2640
atgaactggg agagagacag cttgtacacg tggtcaagtg ggccaaggcc ttgcctggct   2700
tccgcaactt acacgtggac gaccagatgg ctgtcattca gtactcctgg atggggctca   2760
tggtgtttgc catgggctgg cgatccttca ccaatgtcaa ctccaggatg ctctacttcg   2820
cccctgatct ggttttcaat gagtaccgca tgcacaagtc ccggatgtac agccagtgtg   2880
tccgaatgag gcacctctct caagagtttg gatggctcca aatcaccccc caggaattcc   2940
tgtgcatgaa agcactgcta ctcttcagca ttattccagt ggatgggctg aaaaatcaaa   3000
aattctttga tgaacttcga atgaactaca tcaaggaact cgatcgtatc attgcatgca   3060
aaagaaaaaa tcccacatcc tgctcaagac gcttctacca gctcaccaag ctcctggact   3120
ccgtgcagcc tattgcgaga gagctgcatc agttcacttt tgacctgcta atcaagtcac   3180
acatggtgag cgtggacttt ccggaaatga tggcagagat catctctgtg caagtgccca   3240
agatcctttc tgggaaagtc aagcccatct atttccacac ccagtgaagc attggaaacc   3300
ctatttcccc accccagctc atgccccctt tcagatgtct tctgcctgtt ataactctgc   3360
actactcctc tgcagtgcct tggggaattt cctctattga tgtacagtct gtcatgaaca   3420
tgttcctgaa ttctatttgc tgggcttttt ttttctcttt ctctcctttc ttttcttct   3480
tccctcccta tctaaccctc ccatggcacc ttcagacttt gcttcccatt gtggctccta   3540
tctgtgtttt gaatggtgtt gtatgccttt aaatctgtga tgatcctcat atggcccagt   3600
gtcaagttgt gcttgtttac agcactactc tgtgccagcc acacaaacgt ttacttatct   3660
tatgccacgg gaagtttaga gagctaagat tatctgggga aatcaaaaca aaacaagca   3720
aacaaaaaaa aaaagcaaaa acaaaacaaa aaataagcca aaaaccttg ctagtgtttt   3780
ttcctcaaaa ataaataaat aaataaataa atacgtacat acatacacac atacatacaa   3840
acatatagaa atccccaaag aggccaatag tgacgagaag gtgaaaattg caggcccatg   3900
gggagttact gatttttttca tctcctccct ccacgggaga ctttatttttc tgccaatggc   3960
tattgccatt agagggcaga gtgacccag agctgagttg ggcagggggg tggacagaga   4020
ggagaggaca aggagggcaa tggagcatca gtacctgccc acagccttgg tccctggggg   4080
ctagactgct caactgtgga gcaattcatt atactgaaaa tgtgcttgtt gttgaaaatt   4140
tgtctgcatg ttaatgcctc accccaaac ccttttctct ctcactctct gcctccaact   4200
tcagattgac tttcaatagt ttttctaaga cctttgaact gaatgttctc ttcagccaaa   4260
acttggcgac ttccacagaa aagtctgacc actgagaaga aggagagcag agatttaacc   4320
ctttgtaagg ccccatttgg atccaggtct gctttctcat gtgtgagtca gggaggagct   4380
ggagccagag gagaagaaaa tgatagcttg gctgttctcc tgcttaggac actgactgaa   4440
tagttaaact ctcactgcca ctaccttttc cccacctta aaagacctga atgaagtttt   4500
ctgccaaact ccgtgaagcc acaagcacct tatgtcctcc cttcagtgtt ttgtgggcct   4560
gaatttcatc acactgcatt tcagccatgg tcatcaagcc tgtttgcttc ttttgggcat   4620
gttcacagat tctctgttaa gagccccac caccaagaag gttagcaggc caacagctct   4680
gacatctatc tgtagatgcc agtagtcaca aagatttctt accaactctc agatcgctgg   4740
agcccttaga caaactggaa agaaggcatc aaagggatca ggcaagctgg gcgtcttgcc   4800
cttgtccccc agagatgata ccctcccagc aagtggagaa gttctcactt ccttctttag   4860
agcagctaaa ggggctaccc agatcagggt tgaagagaaa actcaattac cagggtggga   4920
```

```
agaatgaagg cactagaacc agaaaccctg caaatgctct tcttgtcacc cagcatatcc    4980
acctgcagaa gtcatgagaa gagagaagga acaaagagga gactctgact actgaattaa    5040
aatcttcagc ggcaaagcct aaagccagat ggacaccatc tggtgagttt actcatcatc    5100
ctcctctgct gctgattctg ggctctgaca ttgcccatac tcactcagat tccccacctt    5160
tgttgctgcc tcttagtcag agggaggcca aaccattgag actttctaca gaaccatggc    5220
ttctttcgga aaggtctggt tggtgtggct ccaatacttt gccacccatg aactcagggt    5280
gtgccctggg acactggttt tatatagtct tttggcacac ctgtgttctg ttgacttcgt    5340
tcttcaagcc caagtgcaag ggaaaatgtc cacctacttt ctcatcttgg cctctgcctc    5400
cttacttagc tcttaatctc atctgttgaa ctcaagaaat caagggccag tcatcaagct    5460
gcccatttta attgattcac tctgtttgtt gagaggatag tttctgagtg acatgatatg    5520
atccacaagg gtttccttcc ctgatttctg cattgatatt aatagccaaa cgaacttcaa    5580
aacagcttta ataacaagg gagagggaa cctaagatga gtaatatgcc aatccaagac    5640
tgctggagaa aactaaagct gacaggttcc ctttttgggg tgggatagac atgttctggt    5700
tttctttatt attacacaat ctggctcatg tacaggatca cttttagctg ttttaaacag    5760
aaaaaaatat ccaccactct tttcagttac actaggttac attttaatag gtcctttaca    5820
tctgttttgg aatgattttc atcttttgtg atacacagat tgaattatat cattttcata    5880
tctctccttg taaatactag aagctctcct ttacatttct ctatcaaatt tttcatcttt    5940
atgggtttcc caattgtgac tcttgtcttc atgaatatat gtttttcatt tgcaaaagcc    6000
aaaaatcagt gaaacagcag tgtaattaaa agcaacaact ggattactcc aaatttccaa    6060
atgacaaaac tagggaaaaa tagcctacac aagcctttag gcctactctt tctgtgcttg    6120
ggtttgagtg aacaaggag attttagctt ggctctgttc tcccatggat gaaaggagga    6180
ggattttttt tttcttttgg ccattgatgt tctagccaat gtaattgaca gaagtctcat    6240
tttgcatgcg ctctgctcta caaacagagt tggtatggtt ggtatactgt actcacctgt    6300
gagggactgg ccactcagac ccacttagct ggtgagctag aagatgagga tcactcactg    6360
gaaaagtcac aaggaccatc tccaaacaag ttggcagtgc tcgatgtgga cgaagagtga    6420
ggaagagaaa aagaaggagc accagggaga aggctccgtc tgtgctgggc agcagacagc    6480
tgccaggatc acgaactctg tagtcaaaga aaagagtcgt gtggcagttt cagctctcgt    6540
tcattgggca gctcgcctag gcccagcctc tgagctgaca tgggagttgt tggattcttt    6600
gtttcatagc tttttctatg ccataggcaa tattgttgtt cttggaaagt ttattatttt    6660
tttaactccc ttactctgag aaagggatat tttgaaggac tgtcatatat ctttgaaaaa    6720
agaaaatctg taatacatat atttttatgt atgttcactg gcactaaaaa atatagagag    6780
cttcattctg tcctttgggt agttgctgag gtaattgtcc aggttgaaaa ataatgtgct    6840
gatgctagag tccctctctg tccatactct acttctaaat acatataggc atacatagca    6900
agttttattt gacttgtact ttaagagaaa atatgtccac catccacatg atgcacaaat    6960
gagctaacat tgagcttcaa gtagcttcta agtgtttgtt tcattaggca cagcacagat    7020
gtggcctttc cccccttctc tcccttgata tctggcaggg cataaaggcc caggccactt    7080
cctctgcccc ttcccagccc tgcaccaaag ctgcatttca ggagactctc tccagacagc    7140
ccagtaacta cccgagcatg gcccctgcat agccctggaa aaataagagg ctgactgtct    7200
acgaattatc ttgtgccagt tgcccaggtg agagggcact gggccaaggg agtggttttc    7260
atgtttgacc cactacaagg ggtcatggga atcaggaatg ccaaagcacc agatcaaatc    7320
```

```
caaaacttaa agtcaaaata agccattcag catgttcagt ttcttggaaa aggaagtttc    7380 taccectgat gcctttgtag gcagatctgt tctcaccatt aatcttttg aaaatctttt     7440 aaagcagttt ttaaaaagag agatgaaagc atcacattat ataaccaaag attacattgt    7500
acctgctaag ataccaaaat tcataagggc aggggggag caagcattag tgcctctttg     7560
ataagctgtc caaagacaga ctaaaggact ctgctggtga ctgacttata agagctttgt    7620
gggttttttt ttccctaata atatacatgt ttagaagaat tgaaataat ttcgggaaaa     7680 tgggattatg ggtccttcac taagtgattt tataagcaga actggctttc cttttctcta    7740
gtagttgctg agcaaattgt tgaagctcca tcattgcatg gttggaaatg gagctgttct    7800
tagccactgt gtttgctagt gcccatgtta gcttatctga agatgtgaaa cccttgctga    7860
taagggagca tttaaagtac tagattttgc actagaggga cagcaggcag aaatccttat    7920
ttctgcccac tttggatggc acaaaaagtt atctgcagtt gaaggcagaa agttgaaata    7980
cattgtaaat gaatatttgt atccatgttt caaaattgaa atatatatat atatatatat    8040
atatatatat atatatatat agtgtgtgtg tgtgttctga tagctttaac tttctctgca    8100 tcttatatt tggttccaga tcacacctga tgccatgtac ttgtgagaga ggatgcagtt     8160
ttgttttgga agctctctca gaacaaacaa gacacctgga ttgatcagtt aactaaaagt    8220
tttctcccct attgggtttg acccacaggt cctgtgaagg agcagaggga taaaagagt     8280 agaggacatg atacattgta ctttactagt tcaagacaga tgaatgtgga aagcataaaa    8340
actcaatgga actgactgag atttaccaca gggaaggccc aaacttgggg ccaaaagcct    8400
acccaagtga ttgaccagtg gccccctaat gggacctgag ctgttggaag aagagaactg    8460
ttccttggtc ttcaccatcc ttgtgagaga agggcagttt cctgcattgg aacctggagc    8520
aagcgctcta tctttcacac aaattccctc acctgagatt gaggtgctct tgttactggg    8580
tgtctgtgtg ctgtaattct ggttttggat atgttctgta aagatttga caatgaaaa     8640 tgtgttttc tctgttaaaa cttgtcagag tactagaagt tgtatctctg taggtgcagg    8700 tccattctg cccacaggta gggtgttttt ctttgattaa gagattgaca cttctgttgc     8760
ctaggacctc ccaactcaac catttctagg tgaaggcaga aaaatccaca ttagttactc    8820
ctcttcagac atttcagctg agataacaaa tcttttggaa ttttttcacc catagaaaga    8880
gtggtagata tttgaattta gcaggtggag tttcatagta aaaacagctt ttgactcagc    8940
tttgatttat cctcatttga tttggccaga aagtaggtaa tatgcattga ttggcttctg    9000
attccaattc agtatagcaa ggtgctaggt ttttccttt ccccacctgt ctcttagcct     9060
ggggaattaa atgagaagcc ttagaatggg tggcccttgt gacctgaaac acttcccaca    9120
taagctactt aacaagattg tcatggagct gcagattcca ttgcccacca aagactagaa    9180
cacacacata tccatacacc aaaggaaaga caattctgaa atgctgtttc tctggtggtt    9240
ccctctctgg ctgctgcctc acagtatggg aacctgtact ctgcagaggt gacaggccag    9300
atttgcatta tctcacaacc ttagcccttg gtgctaactg tcctacagtg aagtgcctgg    9360
ggggttgtcc tatcccataa gccacttgga tgctgacagc agccaccatc agaatgaccc    9420
acgcaaaaaa aagaaaaaaa aaattaaaaa gtcccctcac aacccagtga caccttctg     9480 cttccctcta gactggaaca ttgattaggg agtgcctcag acatgacatt cttgtgctgt    9540
ccttggaatt aatctggcag caggagggag cagactatgt aaacagagat aaaaattaat    9600
tttcaatatt gaaggaaaaa agaaataaga agagagagag aaagaaagca tcacacaaag    9660
```

```
atttcttaa aagaaacaat tttgcttgaa atctctttag atggggctca tttctcacgg    9720
tggcacttgg cctccactgg gcagcaggac cagctccaag cgctagtgtt ctgttctctt    9780
tttgtaatct tggaatcttt tgttgctcta aatacaatta aaaatggcag aaacttgttt    9840
gttggactac atgtgtgact ttgggtctgt ctctgcctct gctttcagaa atgtcatcca    9900
ttgtgtaaaa tattggctta ctggtctgcc agctaaaact tggccacatc ccctgttatg    9960
gctgcaggat cgagttattg ttaacaaaga gacccaagaa aagctgctaa tgtcctctta   10020
tcattgttgt taatttgtta aaacataaag aaatctaaaa tttcaaaaaa              10070

<210> SEQ ID NO 2
<211> LENGTH: 920
<212> TYPE: PRT
<213> ORGANISM: Homo sapiens

<400> SEQUENCE: 2

Met Glu Val Gln Leu Gly Leu Gly Arg Val Tyr Pro Arg Pro Pro
1               5                   10                  15

Lys Thr Tyr Arg Gly Ala Phe Gln Asn Leu Phe Gln Ser Val Arg Glu
                20                  25                  30

Val Ile Gln Asn Pro Gly Pro Arg His Pro Glu Ala Ala Ser Ala Ala
            35                  40                  45

Pro Pro Gly Ala Ser Leu Leu Leu Leu Gln Gln Gln Gln Gln Gln Gln
        50                  55                  60

Gln Gln Gln Gln Gln Gln Gln Gln Gln Gln Gln Gln Gln Gln Gln Gln
65                  70                  75                  80

Glu Thr Ser Pro Arg Gln Gln Gln Gln Gln Gly Glu Asp Gly Ser
                85                  90                  95

Pro Gln Ala His Arg Arg Gly Pro Thr Gly Tyr Leu Val Leu Asp Glu
            100                 105                 110

Glu Gln Gln Pro Ser Gln Pro Gln Ser Ala Leu Glu Cys His Pro Glu
        115                 120                 125

Arg Gly Cys Val Pro Glu Pro Gly Ala Ala Val Ala Ala Ser Lys Gly
    130                 135                 140

Leu Pro Gln Gln Leu Pro Ala Pro Pro Asp Glu Asp Asp Ser Ala Ala
145                 150                 155                 160

Pro Ser Thr Leu Ser Leu Leu Gly Pro Thr Phe Pro Gly Leu Ser Ser
                165                 170                 175

Cys Ser Ala Asp Leu Lys Asp Ile Leu Ser Glu Ala Ser Thr Met Gln
            180                 185                 190

Leu Leu Gln Gln Gln Gln Gln Glu Ala Val Ser Glu Gly Ser Ser Ser
        195                 200                 205

Gly Arg Ala Arg Glu Ala Ser Gly Ala Pro Thr Ser Ser Lys Asp Asn
    210                 215                 220

Tyr Leu Gly Gly Thr Ser Thr Ile Ser Asp Asn Ala Lys Glu Leu Cys
225                 230                 235                 240

Lys Ala Val Ser Val Ser Met Gly Leu Gly Val Glu Ala Leu Glu His
                245                 250                 255

Leu Ser Pro Gly Glu Gln Leu Arg Gly Asp Cys Met Tyr Ala Pro Leu
            260                 265                 270

Leu Gly Val Pro Pro Ala Val Arg Pro Thr Pro Cys Ala Pro Leu Ala
        275                 280                 285

Glu Cys Lys Gly Ser Leu Leu Asp Asp Ser Ala Gly Lys Ser Thr Glu
    290                 295                 300
```

-continued

Asp Thr Ala Glu Tyr Ser Pro Phe Lys Gly Tyr Thr Lys Gly Leu
305                 310                 315                 320

Glu Gly Glu Ser Leu Gly Cys Ser Gly Ser Ala Ala Gly Ser Ser
            325                 330                 335

Gly Thr Leu Glu Leu Pro Ser Thr Leu Ser Leu Tyr Lys Ser Gly Ala
                340                 345                 350

Leu Asp Glu Ala Ala Ala Tyr Gln Ser Arg Asp Tyr Asn Phe Pro
            355                 360                 365

Leu Ala Leu Ala Gly Pro Pro Pro Pro Pro Pro His Pro His
    370                 375                 380

Ala Arg Ile Lys Leu Glu Asn Pro Leu Asp Tyr Gly Ser Ala Trp Ala
385                 390                 395                 400

Ala Ala Ala Gln Cys Arg Tyr Gly Asp Leu Ala Ser Leu His Gly
            405                 410                 415

Ala Gly Ala Ala Gly Pro Gly Ser Gly Ser Pro Ser Ala Ala Ala Ser
            420                 425                 430

Ser Ser Trp His Thr Leu Phe Thr Ala Glu Glu Gly Gln Leu Tyr Gly
            435                 440                 445

Pro Cys Gly Gly Gly Gly Gly Gly Gly Gly Gly Gly Gly Gly
    450                 455                 460

Gly Gly Gly Gly Gly Gly Gly Gly Glu Ala Gly Ala Val Ala Pro
465                 470                 475                 480

Tyr Gly Tyr Thr Arg Pro Pro Gln Gly Leu Ala Gly Gln Glu Ser Asp
                485                 490                 495

Phe Thr Ala Pro Asp Val Trp Tyr Pro Gly Gly Met Val Ser Arg Val
            500                 505                 510

Pro Tyr Pro Ser Pro Thr Cys Val Lys Ser Glu Met Gly Pro Trp Met
            515                 520                 525

Asp Ser Tyr Ser Gly Pro Tyr Gly Asp Met Arg Leu Glu Thr Ala Arg
530                 535                 540

Asp His Val Leu Pro Ile Asp Tyr Tyr Phe Pro Pro Gln Lys Thr Cys
545                 550                 555                 560

Leu Ile Cys Gly Asp Glu Ala Ser Gly Cys His Tyr Gly Ala Leu Thr
            565                 570                 575

Cys Gly Ser Cys Lys Val Phe Phe Lys Arg Ala Ala Glu Gly Lys Gln
            580                 585                 590

Lys Tyr Leu Cys Ala Ser Arg Asn Asp Cys Thr Ile Asp Lys Phe Arg
            595                 600                 605

Arg Lys Asn Cys Pro Ser Cys Arg Leu Arg Lys Cys Tyr Glu Ala Gly
    610                 615                 620

Met Thr Leu Gly Ala Arg Lys Leu Lys Lys Leu Gly Asn Leu Lys Leu
625                 630                 635                 640

Gln Glu Glu Gly Glu Ala Ser Ser Thr Thr Ser Pro Thr Glu Glu Thr
            645                 650                 655

Thr Gln Lys Leu Thr Val Ser His Ile Glu Gly Tyr Glu Cys Gln Pro
            660                 665                 670

Ile Phe Leu Asn Val Leu Glu Ala Ile Glu Pro Gly Val Val Cys Ala
            675                 680                 685

Gly His Asp Asn Asn Gln Pro Asp Ser Phe Ala Ala Leu Leu Ser Ser
            690                 695                 700

Leu Asn Glu Leu Gly Glu Arg Gln Leu Val His Val Val Lys Trp Ala
705                 710                 715                 720

Lys Ala Leu Pro Gly Phe Arg Asn Leu His Val Asp Asp Gln Met Ala

```
                     725                 730                 735
        Val Ile Gln Tyr Ser Trp Met Gly Leu Met Val Phe Ala Met Gly Trp
            740                 745                 750

Arg Ser Phe Thr Asn Val Asn Ser Arg Met Leu Tyr Phe Ala Pro Asp
                755                 760                 765

Leu Val Phe Asn Glu Tyr Arg Met His Lys Ser Arg Met Tyr Ser Gln
            770                 775                 780

Cys Val Arg Met Arg His Leu Ser Gln Glu Phe Gly Trp Leu Gln Ile
        785                 790                 795                 800

Thr Pro Gln Glu Phe Leu Cys Met Lys Ala Leu Leu Leu Phe Ser Ile
                        805                 810                 815

Ile Pro Val Asp Gly Leu Lys Asn Gln Lys Phe Phe Asp Glu Leu Arg
                    820                 825                 830

Met Asn Tyr Ile Lys Glu Leu Asp Arg Ile Ile Ala Cys Lys Arg Lys
                        835                 840                 845

Asn Pro Thr Ser Cys Ser Arg Arg Phe Tyr Gln Leu Thr Lys Leu Leu
        850                 855                 860

Asp Ser Val Gln Pro Ile Ala Arg Glu Leu His Gln Phe Thr Phe Asp
        865                 870                 875                 880

Leu Leu Ile Lys Ser His Met Val Ser Val Asp Phe Pro Glu Met Met
                        885                 890                 895

Ala Glu Ile Ile Ser Val Gln Val Pro Lys Ile Leu Ser Gly Lys Val
                    900                 905                 910

Lys Pro Ile Tyr Phe His Thr Gln
                915                 920

<210> SEQ ID NO 3
<211> LENGTH: 10063
<212> TYPE: DNA
<213> ORGANISM: Mus musculus

<400> SEQUENCE: 3
cagcgccccc tcggagatcc ctaggagcca gcctgctggg agaaccagag ggtccggagc      60
aaacctggag gctgagaggg catcagaggg gaaaagactg agctagccac tccagtgcca     120
tacagaagct taagggacgc accacgccag ccccagccca gcgacagcca acgcctgttg     180
cagagcggcg gcttcgaagc cgccgcccag gagctgccct ttcctcttcg gtgaagtttc     240
taaaagctgc gggagactca gaggaagcaa ggaaagtgtc cggtaggact acggctgcct     300
ttgtcctctt cccctctacc cttacccct cctgggtccc ctctccagga gctgactagg      360
caggctttct ggccaaccct ctcccctaca ccccagctc tgccagccag tttgcacaga      420
ggtaaactcc ctttggctga gagtaggga gcttgttgca cattgcaagg aaggcttttg     480
ggagcccaga gactgaggag caacagcacg cccaggagag tccctggttc caggttctcg     540
cccctgcacc tcctcctgcc cgcccctcac cctgtgtgtg gtgttagaaa tgaaagatg      600 aaaaggcagc tagggtttca gtagtcgaaa gcaaacaaa agctaaaaga aaacaaaaag     660
aaaatagccc agttcttatt tgcacctgct tcagtggact ttgaatttgg aaggcagagg     720
atttcccctt ttccctcccg tcaaggtttg agcatctttt aatctgttct tcaagtattt    780
agagacaaac tgtgtaagta gcagggcaga tcctgtcttg cgcgtgcctt cctttactgg    840
agactttgag ttatctgggg cactccccccc acccacccccc cctcctgcaa gttttcttcc  900
ccggagcttc ccgcaggtgg gcagctagct gcagatacta catcatcagt caggagaact   960
cttcagagca agagacgagg aggcaggata agggaattcg gtggaagcta cagacaagct  1020
```

```
caaggatgga ggtgcagtta gggctgggaa gggtctaccc acggccccca tccaagacct   1080
atcgaggagc gttccagaat ctgttccaga gcgtgcgcga agcgatccag aacccgggcc   1140
ccaggcaccc tgaggccgct aacatagcac ctcccggcgc ctgtttacag cagaggcagg   1200
agactagccc ccggcggcgg cggcggcagc agcacactga ggatggttct cctcaagccc   1260
acatcagagg ccccacaggc tacctggccc tggaggagga acagcagcct tcacagcagc   1320
aggcagcctc cgagggccac cctgagagca gctgcctccc cgagcctggg gcggccaccg   1380
ctcctggcaa ggggctgccg cagcagccac cagctcctcc agatcaggat gactcagctg   1440
ccccatccac gttgtccctg ctgggcccca ctttcccagg cttaagcagc tgctccgccg   1500
acattaaaga cattttgaac gaggccggca ccatgcaact tcttcagcag cagcaacaac   1560
agcagcagca ccaacagcag caccaacagc accaacagca gcaggaggta atctccgaag   1620
gcagcagcgc aagagccagg gaggccacgg gggctccctc ttcctccaag gatagttacc   1680
tagggggcaa ttcaaccata tctgacagtg ccaaggagtt gtgtaaagca gtgtctgtgt   1740
ccatgggatt gggtgtggaa gcattggaac atctgagtcc aggggaacag cttcggggag   1800
actgcatgta cgcgtcgctc ctgggaggtc caccccgcgt gcgtcccact ccttgtgcgc   1860
cgctgcccga atgcaaaggt cttccctgg acgaaggccc aggcaaaagc actgaagaga   1920
ctgctgagta ttcctctttc aagggaggtt acgccaaagg attggaaggt gagagcttgg   1980
ggtgctctgg cagcagtgaa gcaggtagct ctgggacact tgagatcccg tcctctctgt   2040
ctctgtataa atctggagca ctagacgagg cagcagcata ccagaatcgc gactactaca   2100
actttccgct ggctctgtcc gggccgccgc accccccgcc ccctacccat ccacacgccc   2160
gtatcaagct ggagaaccca ttggactacg gcagcgcctg ggctgcggcg gcagcgcaat   2220
gccgctatgg ggacttgggt agtctacatg gagggagtgt agccgggccc agcactggat   2280
cgcccccagc caccacctct tcttcctggc atactctctt cacagctgaa gaaggccaat   2340
tatatgggcc aggaggcggg ggcggcagca gcagcccaag cgatgccggg cctgtagccc   2400
cctatggcta cactcggccc cctcaggggc tgacaagcca ggagagtgac tactctgcct   2460
ccgaagtgtg gtatcctggt ggagttgtga acagagtacc ctatcccagt cccaattgtg   2520
tcaaaagtga atgggaccct tggatggaga actactccgg acctatggg gacatgcgtt   2580 tggacagtac cagggaccat gttttaccca tcgactatta ctttccaccc cagaagacct   2640
gcctgatctg tggagatgaa gcttctggct gtcactacgg agctctcact tgtggcagct   2700
gcaaggtctt cttcaaaaga gccgctgaag ggaaacagaa gtatctatgt gccagcagaa   2760
acgattgtac cattgataaa tttcggagga aaaattgccc atcttgtcgt ctccggaaat   2820
gttatgaagc agggatgact ctgggagctc gtaagctgaa gaaacttgga aatctaaaac   2880
tacaggagga aggagaaaac tccaatgctg gcagccccac tgaggaccca tcccagaaga   2940
tgactgtatc acacattgaa ggctatgaat gtcagcctat ctttcttaac gtcctggaag   3000
ccattgagcc aggagtggtg tgtgccggac atgacaacaa ccaaccagat tcctttgctg   3060
ccttgttatc tagcctcaat gagcttggag agaggcagct tgtgcatgtg gtcaagtggg   3120
ccaaggcctt gcctggcttc cgcaacttgc atgtggatga ccagatggcg gtcattcagt   3180
attcctggat gggactgatg gtatttgcca tgggttggcg gtccttcact aatgtcaact   3240
ccaggatgct ctactttgca cctgacttgg ttttcaatga gtaccgcatg cacaagtctc   3300
ggatgtacag ccagtgtgtg aggatgaggc acctgtctca agagtttgga tggctccaaa   3360
```

```
taacccccca ggaattcctg tgcatgaaag cactgctgct cttcagcatt attccagtgg    3420
atgggctgaa aaatcaaaaa ttctttgatg aacttcgaat gaactacatc aaggaactcg    3480
atcgcatcat tgcatgcaaa agaaagaatc ccacatcctg ctcaaggcgc ttctaccagc    3540
tcaccaagct cctggattct gtgcagccta ttgcaagaga gctgcatcag ttcacttttg    3600
acctgctaat caagtcccat atggtgagcg tggactttcc tgaaatgatg gcagagatca    3660
tctctgtgca agtgcccaag atcctttctg ggaaagtcaa gcccatctat ttccacacac    3720
agtgaagatt tggaaaccct aatacccaaa acccaccttg ttcccttttcc agatgtcttc    3780 tgcctgttat ataactctgc actacttctc tgcagtgcct tgggggaaat tcctctactg    3840
atgtacagtc tgtcgtgaac aggttcctca gttctatttc ctgggcttct ccttcttttt    3900 tttcttctt ccctccctct ttcacctcc catggcacat tttgaatctg ctgcgtattg    3960
tggctcctgc ctttgttttg atttctgttg tatttctttg aatctgtgat gatcctcttg    4020
tggcccagtg tcaattgtgc ttgttttatag cactgtgctg tgtgccaacc aagcaaatgt    4080
ttactcacct tatgccatgg caaatttaga gagctataag tatctgggaga agaaacaaac    4140 agagagaata aaaagcaaaa acaaaaccaa aaaataaaaa aaacacaaac aaaaaacaaa    4200
accaacaaac aaaacatgct aggtttgttt cttcgtggta tacaaataaa cacataggat    4260
tcccaaagaa gccgacagtg actagaagaa agtaaaaaat tacaaatcca cgaggagtca    4320 ctgttttttgt tcatcctgtt tctctgtggg aaacttcagt tgttgttaat ggctattgcc    4380
attaaagagc aggttgaccc caaagcttta ctgatagggt agagagaaaa gaggacaagg    4440
agggcagatg gataaccatt acctccccac agcctttgtc cctgagtcct agagtgctca    4500
gttgcagtgt agttccttgt actgaaatgt gcttcttgtt tgaaaacttg tctgcatgtg    4560
aatgcctctt ccttccaatc ctttttctctc ttaacctctg cttccaccct caattgactt    4620
tcaatagctt ttctcagagc tttgtactat atgctctctt tagccaaaac ttggccactt    4680
tcactgaagt tatgtcagtg agaagaaagt ggaaaggtct gactctttgg aaggctctat    4740
tcagatttat gttcatattt ccatgtgtga gccatagcgg agctttgtga ctggagtcag    4800
aggaaaagga agtgatggct tagccattct cccattagag atagtgaatg atgatgccat    4860
agtgcaatca tccttttcctc tgcttttaaa ggacctagag accccatgca gccacattct    4920
ccctgcacaa gtcttcagtg ttcagtggcc ctgaacttca ccaaaatgca tttaagccaa    4980
ggtggtaaag cttgtacact tctttggacg tgtttgtaga cactgctaag atctccctct    5040
caccaccacc acaaaggcta gcaggccagc agccacagca tctatgttta gatgttaata    5100
gcataaaaga catctcactc aatgtctttc atcaacagta aatttctgga gcccttagaa    5160
aaattggaaa gaaagcatca aagggaccag acaaaatggg catcttgccc ttgtcctcca    5220
gagacaatat attcctccca agtggagaaa tgtcaatttc ctcctcagaa caattaaagg    5280
ggctacccag accatggtgg aagagaaaac taagtaaccc agctgagaaa atgaagaca    5340 ctagaaccag aaagcacagg acttttttcct ttccatccag catacccatt ggcagaaata    5400
atggaaggaa aagagaaggc cagaagaaaa tacagactgc tgaagtcttc agaggcaaag    5460
tctaaagcca gatgaatacc atctggctag atgggcatca gtttgctcat cctcctctat    5520
tgccattgct gggctgactt tggccaaagt tacttcgaat ctccaccata gttgtcccct    5580
ctcagtcaga gggtgcagga ccactgaaac attctatcca ccgtgactct cattggacag    5640
atctggccgg tgtggctaca aatagactgc acccataaac tcagggcaag ccctgggtca    5700
ctggtttcat gtagtctgtt gacagccttc tttactgtgg actctgttcc tcaaccttga    5760
```

```
gtgcaggagg aatgcacatc tacttttgcc tttgtatcat tcctcctcac tcagctcttc    5820
acctccctgc agaccttaag aaatcaggggg ccagctgcca agctgactct tttggttggt    5880
actatgttaa ctgaaaaggt gatttccgaa ggacaggttt tcttccctga tttctttgtt    5940
gctattaata gcaaaaacaa acttgcaaaa caacttcttt aacaaggaag ggaggatata    6000
tacaatgggt gatatggtaa tccaaccctg cttgacaaaa actgaagctg acaggttaca    6060
tttaaaaaca aaacaaaaca aaacgggaca gtttctgatt tgctttgtga caacaccatc    6120
tggcttatgt acaggagctc tcttagctgt tccttaaaca gaaaaaaaat cattactcct    6180
tttagttaaa tttggttaca ttttaatagt ttctttacat ctattctgaa gcaattttg     6240 tcttctgtgg tacatggatt ttattataac attctaatat ttgtctttgt aaatactaga    6300
gactctttga tccatttctc taggaagttt ttcatcttat ggagttctga atcatgactt    6360
ttatctttat gaatgtatat gcttttttact tgcaaaagcc aaaaagagtg aaacagcagt    6420
gcaattaaag caacaccaac taaactccaa atttccaagt gacaatatta gagaaaaaca    6480
gcatacacat ggctttatgc ctactgcttc tgcggtgggg tttgggtgcg caatggaaac    6540
tgtagcttgg ctgtgttctc ccacacaagt gaagaagaga ttggttttg cttttttgga     6600 ttttgtgttt cttttctgtt ttgttttgtt ttgttttgtt ttgctttgct ttctttggcc    6660
atcaatgttc caactaatat gattggcgga gcacgtgctc tgctcagtag agtgaatgtt    6720
gctggtgcac tatgctcacc tgtgaacggc tggccatttc tccattcata tggttaagat    6780
ggaagatgag gatcacttac cagagaagtc aaggtgatca tctccaaaga ggtttacagt    6840
gcttggtagg aatggaaaat gaggacaaga aaaagaggag aaccatggag aaggcccaac    6900
tgggcaggac agcagccagc tgccaaagtc acgaactctg ggattcaaga agagtcgtgt    6960
agtgctttca actctcatcc gcaggcagct cactgtgtgt ggactctgag ctgacacggg    7020
agttggcttc tttgttccat agattttcta tgccacaggc aatattattg ttcttggaaa    7080
gttcattatt ttttttaaatt accttactct cagaaaggga ttttttttgaa ggattctgtc    7140 atatatctttt ggaaaacaga aaatcagtaa tatgtatatt tttatgtatg ttcactggca    7200
ctaaaaaaaa aaaaaaaaag aaaagaaaaa aaagagaaaa aaaaagctt cactctgtcc    7260 tttgggtagt tgctgaggtt aattgtccag gttgagaaat gtgcttctgc taacatcctt    7320
ctctgtccac actctatttc taagtacata taggcatata taggaagata tattcaacac    7380
actttaagaa aaaagtatgt ccaccatcca catgataacc acaatgatac tccacaaatt    7440
acatgacttt aagcttcaag caacttctaa ctgattcatt catttatagc cttgccctct    7500
tctttccctt aaatttggcc cagcacaaag acccaagcca cccttatacc tccctaagac    7560
ttaagccagc accagacttc agaaggtttt ctgaagacaa ctgacttgct atccctgcat    7620
gaccctagca tggtcctgca aacacaagag actaattata attctcctcc actaattgcc    7680
tgggtcacag gtcattgggc caaggccatg attcttatgc ttacgaacca ctaatgctaa    7740
cctactagat taaatcctga actgaaagtt aaaagaagcc atttagcatg tgaaacttct    7800
tggagtaaga agtttctgtc ccggctgcct ttgcaaacag gtttgctttc accacttatc    7860
tccttgaaaa tctttgaagg cctttttttt ttaagtagaa aaggagatga aagcattata    7920
ttatgtaacc aaagattata ttgtatctaa gataccaaat ttttaagggg cagggaagga    7980
gcaagcatta gtgcctcttt ggtaaattat ccaaagacag actgaaggac ttttctgatg    8040
attgacttag aagactttgt ggggaggggt tgtctcacaa tatacatatt tagaagtgtt    8100
```

-continued

```
gagaataatt tgggggggaaa tgggattata gtgtccttca ctaactgatt ttataagcag      8160
aactagcttt cctttttttt tttttttaaag tagttacaaa gcaaattctt aaagctccat      8220
ctttgcatgg ttagaaatgg agctggtctt ggccactgtg tttactagtg cccatgttag      8280
cttatttgaa gatgtgaagc ccttgataag aaggggtaca tttaaaggat tagattttttg     8340 cactagaagg agggcaggca gaaaccctca tttctgccca gtttggacag cacaaaaagt     8400
tctctgcagt ttaaggcaga aagttgaaat atattgtaaa tgagtatttg tatccatgtt     8460
tcaaaactga attctatata tagatgtaat gtgttctgat agctttacct ttctctgcac     8520
ctttatattt ggttccaggt catatctgat gccatgtact tgtaagagag gttgcagtta     8580 cattttttgga tgctctctca gaatggataa gacacctgga ttgatcagat aactgagatc     8640
tcttcccttc ttgggcctgg tgttgaggcc ttgcaaaggg gtggaagagg aaagggtagg     8700
gtacatgatg tattgcactt tactagctta agacggatga atgtggaaag ggtggtgaaa     8760
tttcattgaa aatgcctagg aattgcaata gggagaaatc cagatgtggg gccaggtgcc     8820
cacccaaagg actggccagc agcctcttca tgggatctga ggcattggga aaaggaaggc     8880
tatttccttg gttttcacca tccttgttag agaagggcag ttgcctggtc ttgggaacct     8940
ggagcaaacg ctccttctgt cacatcaatt cttttcccctg caattgaggt gctcttgcta     9000
ctgggtgtcc gtgtgctcta attcggttc tggatatgtt ctgtaaagat tttgataatt     9060
gctaatgtat ttttctctgt taaaaatttg ttagtgtgtt agaagtcata tctctgtagg     9120
tacagatcct ttgctaccca tgagtagagg gattttttttt cttcaattaa gagtttgacc     9180
ctggggtctg ttgcccagag cccatccaga aaaaaaaatc cacatttgtc acaattttttc    9240 tgaaatttca gtcaaggtaa cagatcgctg ggagttctct ttaccccccc aaaaaagcag     9300
ataattgaat ttagcaggtg gtgttttaga gcaaaaaaca aaacagcctt tgacccagct      9360
ttaatatgac ccaatttaat ctggccagga agcaggtaat gtgtattaat tggcttccaa     9420
tcctggttga gtgtagcaag gttctacttt gtttcctagt tccttttgtt acatggcctt     9480
tcacagaaag gattgactgg gtttgcagta tatcttatgg ccttagcacc tattgctaac     9540
tgtcctgaag ggaattgcct atggggttgt cctataagcc acttctatca ttaaaagcag     9600
ccaccaatgg aatctcccag gtttgaaaaa aaaaaaaaaa aacagatggt cctttaccat     9660
tcattgacac acatccctgc tttcctgtag acagattgac tggacattga ttagggaata     9720
catggcaaat gacatgctta cactaccctg gagattaatt tggcagtagg agggaataga     9780
caatgtaacc aagaatgtaa tgtaattctt atagagataa gaattaaatc tggatgtgga     9840
gagagcaaag agagaaagca ttcaatttttt ttttcaaaag aaaccaattt attttgcttg     9900
aaacttcttt cgctggggct tcagttctca cagcggctct tggtctccac tgggcagcag     9960
gaccagcccc aagcgctagt gttctgttct ctttttgtaa tcttggaatc ttttgttgct    10020
ctaaatacaa ttaaaaatgg cagaaacttg tttgttggaa tac                      10063
```

<210> SEQ ID NO 4
<211> LENGTH: 899
<212> TYPE: PRT
<213> ORGANISM: Mus musculus

<400> SEQUENCE: 4

```
Met Glu Val Gln Leu Gly Leu Gly Arg Val Tyr Pro Arg Pro Pro Ser
1               5                   10                  15

Lys Thr Tyr Arg Gly Ala Phe Gln Asn Leu Phe Gln Ser Val Arg Glu
            20                  25                  30
```

```
Ala Ile Gln Asn Pro Gly Pro Arg His Pro Glu Ala Ala Asn Ile Ala
         35                  40                  45

Pro Pro Gly Ala Cys Leu Gln Gln Arg Gln Glu Thr Ser Pro Arg Arg
 50                  55                  60

Arg Arg Arg Gln Gln His Thr Glu Asp Gly Ser Pro Gln Ala His Ile
 65                  70                  75                  80

Arg Gly Pro Thr Gly Tyr Leu Ala Leu Glu Glu Gln Gln Pro Ser
                 85                  90                  95

Gln Gln Gln Ala Ala Ser Glu Gly His Pro Glu Ser Ser Cys Leu Pro
            100                 105                 110

Glu Pro Gly Ala Ala Thr Ala Pro Gly Lys Gly Leu Pro Gln Gln Pro
            115                 120                 125

Pro Ala Pro Pro Asp Gln Asp Asp Ser Ala Ala Pro Ser Thr Leu Ser
130                 135                 140

Leu Leu Gly Pro Thr Phe Pro Gly Leu Ser Ser Cys Ser Ala Asp Ile
145                 150                 155                 160

Lys Asp Ile Leu Asn Glu Ala Gly Thr Met Gln Leu Leu Gln Gln Gln
                165                 170                 175

Gln Gln Gln Gln Gln His Gln Gln Gln His Gln Gln Gln Gln Gln
            180                 185                 190

Gln Glu Val Ile Ser Glu Gly Ser Ser Ala Arg Ala Arg Glu Ala Thr
            195                 200                 205

Gly Ala Pro Ser Ser Ser Lys Asp Ser Tyr Leu Gly Gly Asn Ser Thr
            210                 215                 220

Ile Ser Asp Ser Ala Lys Glu Leu Cys Lys Ala Val Ser Val Ser Met
225                 230                 235                 240

Gly Leu Gly Val Glu Ala Leu Glu His Leu Ser Pro Gly Glu Gln Leu
                245                 250                 255

Arg Gly Asp Cys Met Tyr Ala Ser Leu Leu Gly Gly Pro Pro Ala Val
            260                 265                 270

Arg Pro Thr Pro Cys Ala Pro Leu Pro Glu Cys Lys Gly Leu Pro Leu
            275                 280                 285

Asp Glu Gly Pro Gly Lys Ser Thr Glu Glu Thr Ala Glu Tyr Ser Ser
            290                 295                 300

Phe Lys Gly Gly Tyr Ala Lys Gly Leu Glu Gly Glu Ser Leu Gly Cys
305                 310                 315                 320

Ser Gly Ser Ser Glu Ala Gly Ser Ser Gly Thr Leu Glu Ile Pro Ser
                325                 330                 335

Ser Leu Ser Leu Tyr Lys Ser Gly Ala Leu Asp Glu Ala Ala Ala Tyr
            340                 345                 350

Gln Asn Arg Asp Tyr Tyr Asn Phe Pro Leu Ala Leu Ser Gly Pro Pro
            355                 360                 365

His Pro Pro Pro Thr His Pro His Ala Arg Ile Lys Leu Glu Asn
370                 375                 380

Pro Leu Asp Tyr Gly Ser Ala Trp Ala Ala Ala Ala Gln Cys Arg
385                 390                 395                 400

Tyr Gly Asp Leu Gly Ser Leu His Gly Gly Ser Val Ala Gly Pro Ser
                405                 410                 415

Thr Gly Ser Pro Pro Ala Thr Thr Ser Ser Ser Trp His Thr Leu Phe
            420                 425                 430

Thr Ala Glu Glu Gly Gln Leu Tyr Gly Pro Gly Gly Gly Gly Ser
            435                 440                 445
```

-continued

```
Ser Ser Pro Ser Asp Ala Gly Pro Val Ala Pro Tyr Gly Tyr Thr Arg
    450                 455                 460
Pro Pro Gln Gly Leu Thr Ser Gln Glu Ser Asp Tyr Ser Ala Ser Glu
465                 470                 475                 480
Val Trp Tyr Pro Gly Gly Val Val Asn Arg Val Pro Tyr Pro Ser Pro
                485                 490                 495
Asn Cys Val Lys Ser Glu Met Gly Pro Trp Met Glu Asn Tyr Ser Gly
            500                 505                 510
Pro Tyr Gly Asp Met Arg Leu Asp Ser Thr Arg Asp His Val Leu Pro
        515                 520                 525
Ile Asp Tyr Tyr Phe Pro Pro Gln Lys Thr Cys Leu Ile Cys Gly Asp
530                 535                 540
Glu Ala Ser Gly Cys His Tyr Gly Ala Leu Thr Cys Gly Ser Cys Lys
545                 550                 555                 560
Val Phe Phe Lys Arg Ala Ala Glu Gly Lys Gln Lys Tyr Leu Cys Ala
                565                 570                 575
Ser Arg Asn Asp Cys Thr Ile Asp Lys Phe Arg Arg Lys Asn Cys Pro
            580                 585                 590
Ser Cys Arg Leu Arg Lys Cys Tyr Glu Ala Gly Met Thr Leu Gly Ala
        595                 600                 605
Arg Lys Leu Lys Lys Leu Gly Asn Leu Lys Leu Gln Glu Glu Gly Glu
610                 615                 620
Asn Ser Asn Ala Gly Ser Pro Thr Glu Asp Pro Ser Gln Lys Met Thr
625                 630                 635                 640
Val Ser His Ile Glu Gly Tyr Glu Cys Gln Pro Ile Phe Leu Asn Val
                645                 650                 655
Leu Glu Ala Ile Glu Pro Gly Val Val Cys Ala Gly His Asp Asn Asn
            660                 665                 670
Gln Pro Asp Ser Phe Ala Ala Leu Leu Ser Ser Leu Asn Glu Leu Gly
        675                 680                 685
Glu Arg Gln Leu Val His Val Val Lys Trp Ala Lys Ala Leu Pro Gly
690                 695                 700
Phe Arg Asn Leu His Val Asp Asp Gln Met Ala Val Ile Gln Tyr Ser
705                 710                 715                 720
Trp Met Gly Leu Met Val Phe Ala Met Gly Trp Arg Ser Phe Thr Asn
                725                 730                 735
Val Asn Ser Arg Met Leu Tyr Phe Ala Pro Asp Leu Val Phe Asn Glu
            740                 745                 750
Tyr Arg Met His Lys Ser Arg Met Tyr Ser Gln Cys Val Arg Met Arg
        755                 760                 765
His Leu Ser Gln Glu Phe Gly Trp Leu Gln Ile Thr Pro Gln Glu Phe
770                 775                 780
Leu Cys Met Lys Ala Leu Leu Leu Phe Ser Ile Ile Pro Val Asp Gly
785                 790                 795                 800
Leu Lys Asn Gln Lys Phe Phe Asp Glu Leu Arg Met Asn Tyr Ile Lys
                805                 810                 815
Glu Leu Asp Arg Ile Ile Ala Cys Lys Arg Lys Asn Pro Thr Ser Cys
            820                 825                 830
Ser Arg Arg Phe Tyr Gln Leu Thr Lys Leu Leu Asp Ser Val Gln Pro
        835                 840                 845
Ile Ala Arg Glu Leu His Gln Phe Thr Phe Asp Leu Leu Ile Lys Ser
850                 855                 860
His Met Val Ser Val Asp Phe Pro Glu Met Met Ala Glu Ile Ile Ser
```

Val Gln Val Pro Lys Ile Leu Ser Gly Lys Val Lys Pro Ile Tyr Phe
865                 870                 875                 880
                    885                 890                 895

His Thr Gln

<210> SEQ ID NO 5
<211> LENGTH: 4137
<212> TYPE: DNA
<213> ORGANISM: Rattus norvegicus

<400> SEQUENCE: 5

```
atccctagga gccagcctgc tgggagaacc agagggtccg gagcaaacct ggaggctgag    60
agggcatcag aggggaaaag actgagttag ccactccagt gccatacaga agcttaaggg   120
acataccacg ccagcccag cccagcgaca gccaacgcct gttgcagagc ggcggcttcg    180
aagccgccgc ccagaagctg cccttcctc ttcggtgaag tttctaaaag ctgcgggaga    240
ctcggaggaa gcgaagaaag tgtccggtag gactacgact gcctttgtcc tcctccctcc   300
taccccctacc cctcctgggt cccctctccc tgagcggact aggcaggctt cctggccagc   360
cctctcccct acaccaccag ctctgccagc cagtttgcac agaggtaact ccctttggct    420
gaaagcagac gagcttgttg cccattggaa gggaggcttt tgggagccca gagactgagg    480
agcaacagca cgctggagag tccctgattc caggttctcc ccctgcacc tcctactgcc      540
cgccccctcac cctgtgtgtg cagctagaat tgaaaagatg aaaagacagt gggggcttca   600
gtagtcgaaa gcaaacaaa agcaaaaaga aacaaaaag aaaatagccc agttcttatt      660
tgcacctgct tcagtggaca ttgactttgg aaggcagaga atttttccttc cccccagtca    720
agctttgagc atctttttaat ctgttcttca agtatttagg acaaactgt gaaactagca    780
gggcagatcc tgtctagcgc gtgccttcct ttacaggaga ctttgaggct atctgggcgc   840
tccccccct ccctgcaagt tttcttccct ggagcttccc gcaggtgggc agctagctgc      900
agatactaca tcatcagtca gtagaactct tcagagcaag agacgaggag gcaggataag    960
ggaattcggt ggaagctaga gacaagctaa aggatggagg tgcagttagg gctgggaagg   1020
gtctacccac ggccccgtc caagacctat cgaggagcgt tccagaatct gttccagagc    1080
gtgcgcgaag cgatccagaa cccgggccc aggcaccctg aggccgctag catagcacct   1140
cccggtgcct gtttacagca gcggcaggag actagccccc ggcggcggcg gcggcagcag   1200
cacctgagg atggctctcc tcaagcccac atcagaggca ccacaggcta cctggccctg    1260
gaggaggaac agcagccttc acagcagcag tcagcctccg agggccaccc tgagagcggc   1320
tgcctcccgg agcctggagc tgccacggct cctggcaagg gctgccgca gcagccacca    1380
gctcctccag atcaggatga ctcagctgcc ccatccacgt tgtccctact gggcccact    1440
ttcccaggct taagcagctg ctccgcagac attaaagaca tcctgagcga ggccggcacc   1500
atgcaacttc ttcagcagca gcagcaacag caacagcagc agcagcagca gcagcagcag   1560
cagcagcaac agcagcagga ggtaatatcc gaaggcagca gcagcgtgag agcaagggag   1620
gccactgggg ctcctctctc ctccaaggat agttacctag gggcaattc gaccatatct     1680
gacagtgcca aggagttgtg taagcagtg tctgtgtcca tggggttggg tgtggaagca    1740
ctggaacatc tgagtccagg ggagcagctt cggggcgact gcatgtacgc gtcgctcctg   1800
ggaggtccac ccgccgtgcg tcccactcct tgtgcgcctc tggccgaatg caaaggtctt   1860
tccctggacg aaggcccggg caaggcact gaagagactc ctgagtattc ctctttcaag   1920
```

| | | |
|---|---|---|
| ggaggttacg ccaaagggtt ggaaggtgag agtctgggct gctctggcag cagtgaagca | 1980 |
| ggtagctctg ggacacttga gatcccgtcc tcactgtctc tgtataagtc tggagcagta | 2040 |
| gacgaggcag cagcatacca gaatcgcgac tactacaact ttccgctcgc tctgtccggg | 2100 |
| ccgccgcacc ccccgccccc tacccatcca cacgccgca tcaagctgga aacccgtcg | 2160 |
| gactacggca gcgcctgggc tgcggcggca gcgcaatgcc gctatgggga cttggctagc | 2220 |
| ctacatggag ggagtgtagc cggacccagc actggatcgc cccagccac cgcctcttct | 2280 |
| tcctggcata ctctcttcac agctgaagaa ggccaattat atgggccagg aggcggggc | 2340 |
| ggcagcagta gcccaagcga tgctgggcct gtagccccct atggctacac tcggcccct | 2400 |
| caggggctgg caagccagga gggtgacttc tctgcctctg aagtgtggta tcctggtgga | 2460 |
| gttgtgaaca gagtccccta tcccagtccc agttgtgtta aagtgaaat gggaccttgg | 2520 |
| atggagaact actccggacc ttatggggac atgcgtttgg acagtaccag ggaccacgtt | 2580 |
| ttacccatcg actattactt cccaccccag aagacctgcc tgatctgtgg agatgaagct | 2640 |
| tctggttgtc actacggagc tctcacttgt ggcagctgca aggtcttctt caaaagagct | 2700 |
| gcggaaggga acagaagta tctatgtgcc agcagaaatg attgcaccat tgataaattt | 2760 |
| cggaggaaaa attgtccatc gtgtcgtctc cggaaatgtt atgaagcagg gatgactctg | 2820 |
| ggagctcgta agctgaagaa acttggaaat ctcaaactac aggaagaagg agaaaactcc | 2880 |
| agtgctggta gccccactga ggacccatcc agaagatga ctgtatcaca cattgaaggc | 2940 |
| tatgaatgtc aacctatctt tcttaatgtc ctggaagcca ttgagccagg agtggtgtgt | 3000 |
| gccggacatg acaacaacca gcctgattcc tttgctgcct tgttatctag tctcaacgag | 3060 |
| cttggcgaga acagcttgt acatgtggtc aagtgggcca aggccttgcc tggcttccgc | 3120 |
| aacttgcatg tggatgacca gatggcagtc attcagtatt cctggatggg actgatggta | 3180 |
| tttgccatgg gttggcggtc cttcactaat gtcaactcta ggatgctcta ctttgcacct | 3240 |
| gacctggttt tcaatgagta tcgcatgcac aagtctcgaa tgtacagcca gtgcgtgagg | 3300 |
| atgaggcacc tttctcaaga gtttggatgg ctccagataa ccccccagga attcctgtgc | 3360 |
| atgaaagcac tgctactctt cagcattatt ccagtggatg ggctgaaaaa tcaaaaattc | 3420 |
| tttgatgaac ttcgaatgaa ctacatcaag gaacttgatc gcatcattgc atgcaaaaga | 3480 |
| aaaaatccca catcctgctc aaggcgcttc taccagctca ccaagctcct ggattctgtg | 3540 |
| cagcctattg caagagagct gcatcaattc acttttgacc tgctaatcaa gtcccatatg | 3600 |
| gtgagcgtgg actttcctga aatgatggca gagatcatct ctgtgcaagt gcccaagatc | 3660 |
| ctttctggga agtcaagcc catctatttc cacacacagt gaagatttgg aaaccctaat | 3720 |
| acccaaaccc accttgttcc cttttcagat gtcttctgcc tgtttatataa ctctgcacta | 3780 |
| cttctctggc atgggccttg ggggaaattc ctctactgat gtacagtctg tcatgaacat | 3840 |
| gttccccaag ttctatttcc tgggcttttc cttctttctt tttcttcttc tctgcctctt | 3900 |
| ttaccctccc atggcacatt ttgaatccgc tgcgtgttgt ggctcctgcc tgtgttttga | 3960 |
| gttttgttgt atttcttcaa gtctgtgatg atcttcttgt ggcccagtgt caactgtgct | 4020 |
| tgtttatagc actgtgctgt gtgccaacca agcaaatgtt tactcacctt atgccatggc | 4080 |
| aagtttagag agctataagt atcttgggaa gaaacaaaca gagagagtaa aaaaacc | 4137 |

<210> SEQ ID NO 6
<211> LENGTH: 902
<212> TYPE: PRT
<213> ORGANISM: Rattus norvegicus

<400> SEQUENCE: 6

```
Met Glu Val Gln Leu Gly Leu Gly Arg Val Tyr Pro Arg Pro Pro Ser
1               5                   10                  15

Lys Thr Tyr Arg Gly Ala Phe Gln Asn Leu Phe Gln Ser Val Arg Glu
            20                  25                  30

Ala Ile Gln Asn Pro Gly Pro Arg His Pro Glu Ala Ala Ser Ile Ala
        35                  40                  45

Pro Pro Gly Ala Cys Leu Gln Arg Gln Glu Thr Ser Pro Arg Arg
    50                  55                  60

Arg Arg Arg Gln Gln His Pro Glu Asp Gly Ser Pro Gln Ala His Ile
65              70                  75                  80

Arg Gly Thr Thr Gly Tyr Leu Ala Leu Glu Glu Gln Gln Pro Ser
                85                  90                  95

Gln Gln Gln Ser Ala Ser Glu Gly His Pro Glu Ser Gly Cys Leu Pro
                100                 105                 110

Glu Pro Gly Ala Ala Thr Ala Pro Gly Lys Gly Leu Pro Gln Gln Pro
            115                 120                 125

Pro Ala Pro Pro Asp Gln Asp Asp Ser Ala Ala Pro Ser Thr Leu Ser
    130                 135                 140

Leu Leu Gly Pro Thr Phe Pro Gly Leu Ser Ser Cys Ser Ala Asp Ile
145                 150                 155                 160

Lys Asp Ile Leu Ser Glu Ala Gly Thr Met Gln Leu Leu Gln Gln Gln
                165                 170                 175

Gln Gln Gln Gln Gln Gln Gln Gln Gln Gln Gln Gln Gln Gln Gln Gln
                180                 185                 190

Gln Gln Gln Glu Val Ile Ser Glu Gly Ser Ser Ser Val Arg Ala Arg
                195                 200                 205

Glu Ala Thr Gly Ala Pro Ser Ser Ser Lys Asp Ser Tyr Leu Gly Gly
    210                 215                 220

Asn Ser Thr Ile Ser Asp Ser Ala Lys Glu Leu Cys Lys Ala Val Ser
225                 230                 235                 240

Val Ser Met Gly Leu Gly Val Glu Ala Leu Glu His Leu Ser Pro Gly
                245                 250                 255

Glu Gln Leu Arg Gly Asp Cys Met Tyr Ala Ser Leu Leu Gly Gly Pro
                260                 265                 270

Pro Ala Val Arg Pro Thr Pro Cys Ala Pro Leu Ala Glu Cys Lys Gly
                275                 280                 285

Leu Ser Leu Asp Glu Gly Pro Gly Lys Gly Thr Glu Glu Thr Ala Glu
    290                 295                 300

Tyr Ser Ser Phe Lys Gly Gly Tyr Ala Lys Gly Leu Glu Gly Glu Ser
305                 310                 315                 320

Leu Gly Cys Ser Gly Ser Ser Glu Ala Gly Ser Ser Gly Thr Leu Glu
                325                 330                 335

Ile Pro Ser Ser Leu Ser Leu Tyr Lys Ser Gly Ala Val Asp Glu Ala
                340                 345                 350

Ala Ala Tyr Gln Asn Arg Asp Tyr Tyr Asn Phe Pro Leu Ala Leu Ser
            355                 360                 365

Gly Pro Pro His Pro Pro Pro Thr His Pro His Ala Arg Ile Lys
    370                 375                 380

Leu Glu Asn Pro Ser Asp Tyr Gly Ser Ala Trp Ala Ala Ala Ala
385                 390                 395                 400

Gln Cys Arg Tyr Gly Asp Leu Ala Ser Leu His Gly Gly Ser Val Ala
```

```
            405                 410                 415
Gly Pro Ser Thr Gly Ser Pro Ala Thr Ala Ser Ser Trp His
            420                 425                 430
Thr Leu Phe Thr Ala Glu Glu Gly Gln Leu Tyr Gly Pro Gly Gly Gly
            435                 440                 445
Gly Gly Ser Ser Ser Pro Ser Asp Ala Gly Pro Val Ala Pro Tyr Gly
            450                 455                 460
Tyr Thr Arg Pro Pro Gln Gly Leu Ala Ser Gln Glu Gly Asp Phe Ser
465                 470                 475                 480
Ala Ser Glu Val Trp Tyr Pro Gly Gly Val Val Asn Arg Val Pro Tyr
            485                 490                 495
Pro Ser Pro Ser Cys Val Lys Ser Glu Met Gly Pro Trp Met Glu Asn
            500                 505                 510
Tyr Ser Gly Pro Tyr Gly Asp Met Arg Leu Asp Ser Thr Arg Asp His
            515                 520                 525
Val Leu Pro Ile Asp Tyr Tyr Phe Pro Pro Gln Lys Thr Cys Leu Ile
            530                 535                 540
Cys Gly Asp Glu Ala Ser Gly Cys His Tyr Gly Ala Leu Thr Cys Gly
545                 550                 555                 560
Ser Cys Lys Val Phe Phe Lys Arg Ala Ala Glu Gly Lys Gln Lys Tyr
            565                 570                 575
Leu Cys Ala Ser Arg Asn Asp Cys Thr Ile Asp Lys Phe Arg Arg Lys
            580                 585                 590
Asn Cys Pro Ser Cys Arg Leu Arg Lys Cys Tyr Glu Ala Gly Met Thr
            595                 600                 605
Leu Gly Ala Arg Lys Leu Lys Lys Leu Gly Asn Leu Lys Leu Gln Glu
            610                 615                 620
Glu Gly Glu Asn Ser Ser Ala Gly Ser Pro Thr Glu Asp Pro Ser Gln
625                 630                 635                 640
Lys Met Thr Val Ser His Ile Glu Gly Tyr Glu Cys Gln Pro Ile Phe
            645                 650                 655
Leu Asn Val Leu Glu Ala Ile Glu Pro Gly Val Val Cys Ala Gly His
            660                 665                 670
Asp Asn Asn Gln Pro Asp Ser Phe Ala Ala Leu Leu Ser Ser Leu Asn
            675                 680                 685
Glu Leu Gly Glu Arg Gln Leu Val His Val Val Lys Trp Ala Lys Ala
            690                 695                 700
Leu Pro Gly Phe Arg Asn Leu His Val Asp Asp Gln Met Ala Val Ile
705                 710                 715                 720
Gln Tyr Ser Trp Met Gly Leu Met Val Phe Ala Met Gly Trp Arg Ser
            725                 730                 735
Phe Thr Asn Val Asn Ser Arg Met Leu Tyr Phe Ala Pro Asp Leu Val
            740                 745                 750
Phe Asn Glu Tyr Arg Met His Lys Ser Arg Met Tyr Ser Gln Cys Val
            755                 760                 765
Arg Met Arg His Leu Ser Gln Glu Phe Gly Trp Leu Gln Ile Thr Pro
            770                 775                 780
Gln Glu Phe Leu Cys Met Lys Ala Leu Leu Leu Phe Ser Ile Ile Pro
785                 790                 795                 800
Val Asp Gly Leu Lys Asn Gln Lys Phe Phe Asp Glu Leu Arg Met Asn
            805                 810                 815
Tyr Ile Lys Glu Leu Asp Arg Ile Ile Ala Cys Lys Arg Lys Asn Pro
            820                 825                 830
```

```
Thr Ser Cys Ser Arg Arg Phe Tyr Gln Leu Thr Lys Leu Leu Asp Ser
        835                 840                 845

Val Gln Pro Ile Ala Arg Glu Leu His Gln Phe Thr Phe Asp Leu Leu
    850                 855                 860

Ile Lys Ser His Met Val Ser Val Asp Phe Pro Glu Met Met Ala Glu
865                 870                 875                 880

Ile Ile Ser Val Gln Val Pro Lys Ile Leu Ser Gly Lys Val Lys Pro
                885                 890                 895

Ile Tyr Phe His Thr Gln
            900

<210> SEQ ID NO 7
<211> LENGTH: 28
<212> TYPE: DNA
<213> ORGANISM: Artificial Sequence
<220> FEATURE:
<223> OTHER INFORMATION: synthetic

<400> SEQUENCE: 7
acatcaagga actcgatcgt atcattgc                                          28

<210> SEQ ID NO 8
<211> LENGTH: 20
<212> TYPE: DNA
<213> ORGANISM: Artificial Sequence
<220> FEATURE:
<223> OTHER INFORMATION: synthetic

<400> SEQUENCE: 8
ttgggcactt gcacagagat                                                   20

<210> SEQ ID NO 9
<211> LENGTH: 9
<212> TYPE: PRT
<213> ORGANISM: Homo sapiens

<400> SEQUENCE: 9

Leu Leu Leu Phe Ser Ile Ile Pro Val
1               5

<210> SEQ ID NO 10
<211> LENGTH: 10
<212> TYPE: PRT
<213> ORGANISM: Homo sapiens

<400> SEQUENCE: 10

Arg Met Leu Tyr Phe Ala Pro Asp Leu Val
1               5                   10

<210> SEQ ID NO 11
<211> LENGTH: 9
<212> TYPE: PRT
<213> ORGANISM: Homo sapiens

<400> SEQUENCE: 11

Phe Leu Cys Met Lys Ala Leu Leu Leu
1               5

<210> SEQ ID NO 12
<211> LENGTH: 9
<212> TYPE: PRT
<213> ORGANISM: Homo sapiens
```

<400> SEQUENCE: 12

Gln Leu Thr Lys Leu Leu Asp Ser Val
1               5

<210> SEQ ID NO 13
<211> LENGTH: 32
<212> TYPE: DNA
<213> ORGANISM: Artificial Sequence
<220> FEATURE:
<223> OTHER INFORMATION: synthetic

<400> SEQUENCE: 13
ccatcttgtc gtcttcggaa atgttatgaa gc                                    32

<210> SEQ ID NO 14
<211> LENGTH: 26
<212> TYPE: DNA
<213> ORGANISM: Artificial Sequence
<220> FEATURE:
<223> OTHER INFORMATION: synthetic

<400> SEQUENCE: 14
tttgaatgag gcaagtcagc ctttct                                           26

<210> SEQ ID NO 15
<211> LENGTH: 26
<212> TYPE: DNA
<213> ORGANISM: Artificial Sequence
<220> FEATURE:
<223> OTHER INFORMATION: synthetic

<400> SEQUENCE: 15
tcatgaagtg tgacgttgac atccgt                                           26

<210> SEQ ID NO 16
<211> LENGTH: 26
<212> TYPE: DNA
<213> ORGANISM: Artificial Sequence
<220> FEATURE:
<223> OTHER INFORMATION: synthetic

<400> SEQUENCE: 16
cttagaagca tttgcggtgc acgatg                                           26

<210> SEQ ID NO 17
<211> LENGTH: 20
<212> TYPE: DNA
<213> ORGANISM: Artificial Sequence
<220> FEATURE:
<223> OTHER INFORMATION: synthetic

<400> SEQUENCE: 17
ggaccatgtt ttacccatcg                                                  20

<210> SEQ ID NO 18
<211> LENGTH: 20
<212> TYPE: DNA
<213> ORGANISM: Artificial Sequence
<220> FEATURE:
<223> OTHER INFORMATION: synthetic

<400> SEQUENCE: 18
atctggtcat ccacatgcaa                                                  20

<210> SEQ ID NO 19

```
<211> LENGTH: 20
<212> TYPE: DNA
<213> ORGANISM: Artificial Sequence
<220> FEATURE:
<223> OTHER INFORMATION: synthetic

<400> SEQUENCE: 19
ttgttgtggc agcagagttc                                                    20

<210> SEQ ID NO 20
<211> LENGTH: 19
<212> TYPE: DNA
<213> ORGANISM: Artificial Sequence
<220> FEATURE:
<223> OTHER INFORMATION: synthetic

<400> SEQUENCE: 20
aagtggggaa ccacagcat                                                     19
```

COMBINATORIAL ANDROGEN DEPRIVATION WITH AN ANDROGEN RECEPTOR VACCINE

CROSS-REFERENCE TO RELATED APPLICATIONS

This application claims priority to U.S. Provisional Application No. 62/347,646 filed on Jun. 9, 2016, the contents of which is incorporated by reference in its entirety.

STATEMENT REGARDING FEDERALLY SPONSORED RESEARCH OR DEVELOPMENT

This invention was made with government support under CA142608 awarded by the National Institutes of Health. The government has certain rights in the invention.

BACKGROUND OF THE INVENTION

Prostate cancer is a significant health risk for men over the age of 50, with about 200,000 newly diagnosed cases each year in the United States (Jemal A. et al., Cancer Statistics, 2005 (2005) CA Cancer J Clin, 55:10-30). It is the most common tumor diagnosed among men and the second leading cause of male cancer-related death in the United States (Jemal et al., Cancer Statistics, 2003 (2003) CA Cancer J Clin, 53:5-26). Despite advances in screening and early detection, approximately 30% of patients undergoing definitive prostatectomy or ablative radiation therapy will have recurrent disease at 10 years (Oefelein et al., 1997, J Urol, 158:1460-1465).

The androgen receptor (AR) is a steroid hormone receptor that plays a crucial role in the development of normal prostate tissue, as well as in the progression of prostate cancer. Patients with metastatic disease are initially treated with androgen deprivation therapy, and androgen deprivation typically is continued indefinitely once a patient has metastatic prostate cancer. Given its use in this context for over 60 years, androgen deprivation (AD) represents one of the first truly "targeted" therapies for a solid tumor, and there are few examples in the current armamentarium of novel cancer-targeting agents with as high a response rate. However, despite the initial response to this treatment in over 80% of patients, castration resistance usually emerges, with a median time of 2-3 years. Other groups have identified that amplification of the AR is a common, and perhaps the most common, mechanism of resistance to androgen deprivation therapy, with AR-activating mutations, overexpression and/or gene amplification occurring in over 50% of patients with castration-resistant disease. These findings underscore the importance of the AR to prostate cancer, and suggest that AR antigen-loss (a major means of resistance to immunotherapy) is less likely in human prostate cancer. Recent findings have demonstrated that AR-mediated signaling remains active in the majority of castrate-resistant tumors, and hence the preferred nomenclature is now "castrate resistant" rather than "androgen independent" as was formerly used. Because one of the central means of resistance to androgen deprivation is increased AR expression, in some cases through gene amplification, the pharmacological targeting of the AR can paradoxically cause the AR to remain a target in patients with advanced, castrate-resistant disease. Metastatic prostate cancer that is castration-resistant (mCRPC) is the lethal form of this disease. With a median life expectancy of less than 3 years for patients with mCRPC, treatments that can delay the establishment of castration resistance, or treat this stage of disease more effectively, are urgently needed.

DNA vaccines have recently been added to the arsenal of treatments against prostate cancer. Relative to other vaccine approaches, DNA vaccines are advantageous in being relatively easy and inexpensive to manufacture, and are "off-the-shelf" rather than individualized. Animal studies have demonstrated that DNA vaccines lead to antigen presentation through naturally processed MEW class I and II epitopes. Several DNA vaccines are being explored by academic and industry groups as novel treatments for different cancer types, and early stage clinical trials have shown DNA vaccines can augment immune responses and show evidence of clinical responses. Our laboratory has focused recent efforts on the ligand-binding domain of the androgen receptor (AR LBD) as a biologically relevant target protein, critical for the development and progression of prostate cancer. Our laboratory has demonstrated that many patients with prostate cancer have existing humoral and cellular immune responses specific for the AR LBD, and that cytolytic CD8+ T cells specific for the AR LBD can lyse human prostate cancer cells in an MHC class I-restricted fashion. We further demonstrated that a DNA vaccine encoding the AR LBD can elicit epitope-specific cytolytic CD8+ T cells in HLA-A2 transgenic mice, and used these mice as a tumor model system to assess DNA vaccines targeting AR LBD and other antigens. Immunizing tumor-bearing mice with AR LBD DNA vaccine elicited anti-tumor responses and significantly prolonged overall survival of mice.

There is a need for new and more effective treatment for prostate cancer, especially in treatment or prevention of castrate-resistant disease.

BRIEF SUMMARY

This disclosure is based on the surprising findings that the addition to androgen deprivation therapy of a vaccine directed toward the androgen receptor represses prostate tumor growth and delay onset or progression of metastatic disease.

Accordingly, in a first aspect, the disclosure encompasses a method for eliciting an anti-tumor response in a subject having prostate cancer comprising: a) administering to the subject androgen deprivation therapy (ADT or androgen suppression therapy); and b) administering to the subject a vaccine directed toward the androgen receptor, wherein the vaccine are administered in an amount effective to elicit an increased anti-tumor response to the prostate cancer. This results in an inhibition, delay or reduction in growth of prostate cancer or metastatic disease. The Examples demonstrate a significant delay in tumor growth when the vaccine was combined with standard ADT therapy. In one embodiment, the vaccine is a DNA vaccine comprising a polynucleotide that encodes for an androgen receptor or a fragment of the androgen receptor. In another embodiment, the vaccine is a polypeptide vaccine comprising the androgen receptor or fragments thereof.

Accordingly, in a second aspect, the disclosure encompasses a method for eliciting an anti-tumor response in a subject having prostate cancer comprising: a) administering to the subject ADT; and b) administering to the subject a recombinant DNA vaccine comprising a polynucleotide operably linked to a transcriptional regulatory element wherein the polynucleotide encodes a androgen receptor or a fragment of the androgen receptor, wherein the ADT and the recombinant DNA vaccine are administered in an amount effective to elicit an increased anti-tumor response to the prostate cancer, and wherein the combination delays, reduced or inhibits prostate cancer cell growth or metastasis.

In a third aspect, the disclosure encompasses a method of increasing the efficacy of androgen deprivation therapy in a subject with prostate cancer comprising administering to the subject an effective amount of a recombinant DNA vaccine comprising a polynucleotide operably linked to a transcriptional regulatory element wherein the polynucleotide encodes an androgen receptor or a fragment of the androgen receptor, wherein the method inhibits, delays or reduces the growth of the prostate cancer.

In a fourth aspect, the disclosure encompasses a method of increasing the efficacy of ADT and/or augmenting or increasing the anti-tumor response of ADT treatment by administering an effective amount of a recombinant DNA vaccine and a PD-1 pathway inhibitor in an effective amount to increase the anti-tumor efficacy of ADT and/or increase or augment the anti-tumor response to ADT treatment. This triple combination therapy results in a significant delay in prostate tumor growth and metastasis.

In a fifth aspect, the disclosure encompasses a kit for treating prostate cancer comprising androgen deprivation therapy and a vaccine that elicits an anti-androgen receptor immune response.

In yet another aspect, the disclosure encompasses a kit for treating prostate cancer comprising androgen deprivation therapy, a vaccine that elicits an anti-androgen receptor immune response and a PD-1 pathway inhibitor.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

FIG. 5E shows frequency of CD8+ T cells expressing the surface degranulation marker CD107a. FIG. 5F shows cytotoxicity of T-cells cultured with 22Rv1/CSS (blue) or 22Rv1/FCS (red) cells.

FIG. 12G demonstrates AR-specific T cells obtained following peptide-immunization have increased recognition and lysis of androgen-deprived prostate tumor cells. Splenocytes from AR811 peptide-immunized HLA-A2 transgenic (HHDII-DR1) mice were co-cultured with HLA-A2-expressing 22Rv1/FCS or 22Rv1/CSS cells, and measured for intracellular cytokine expression of IFNg and TNFα.

FIG. 12H demonstrates AR-specific T-cells of FIG. 12G express CD69 on their surface.

FIG. 12I demonstrates AR-specific T cells of FIG. 12G are cytotoxic.

DETAILED DESCRIPTION

Figure 1:
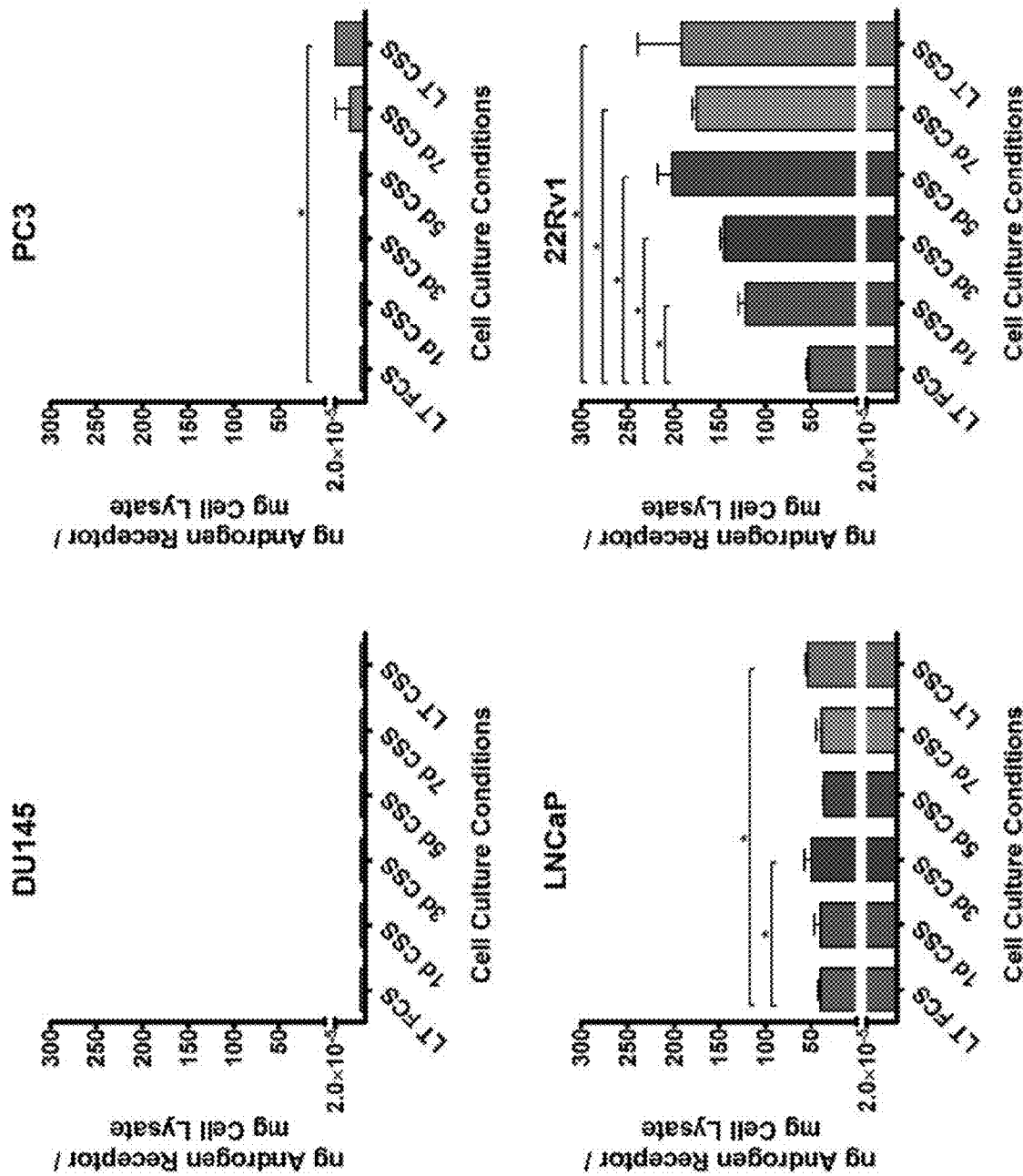
FIG. 1 shows that short- or long-term androgen withdrawal increases AR protein expression in 22Rv1 prostate cancer cells.

This disclosure provides compositions and methods related to combination therapies for treating prostate cancer. The specific combination of androgen therapy and vaccine against the androgen receptor (for example a DNA vaccine) unexpectedly and synergistically improves the efficacy ADT for treatment of prostate cancer, including metastatic or castrate-resistant disease. The combination therapy results in a significant decrease in tumor growth as compared to ADT alone.

In one embodiment, the method for eliciting an anti-tumor response in a subject having prostate cancer comprising: administering to the subject ADT and administering to the subject a vaccine directed toward the androgen receptor, wherein the vaccine is administered in an amount effective to elicit an increased anti-tumor response to the prostate cancer compared to ADT treatment alone. This increased anti-tumor response to prostate cancer results in the reduction, inhibition or delay of prostate cancer cell growth and/or metastasis, prolonging subject survival. In one embodiment, the anti-tumor response of the combination treatment results in a significant delay in tumor cell growth as compared to ADT treatment alone. In one embodiment, the vaccine is a DNA vaccine comprising a polynucleotide that encodes for an androgen receptor or a fragment of the androgen receptor. In another embodiment, the vaccine is a polypeptide vaccine comprising the androgen receptor or fragment thereof.

In one embodiment, the disclosure provides a method of eliciting an anti-tumor response in a subject having prostate cancer comprising: a. administering to the subject androgen deprivation therapy (ADT); and b. administering to the subject a recombinant DNA vaccine comprising a polynucleotide operably linked to a transcriptional regulatory element wherein the polynucleotide encodes a androgen receptor or a fragment of the androgen receptor, wherein the ADT and the recombinant DNA vaccine are administered in an amount effective to elicit an anti-tumor response to the prostate cancer.

Anti-tumor response in a subject includes the reducing, repressing, delaying or preventing tumor growth, reduction of tumor volume, and/or preventing, repressing, delaying or reducing metastasis of the tumor. Anti-tumor response includes the reduction of the number of tumor cells within the subject. In some embodiments, anti-tumor response includes an immune response to tumor cells expressing the androgen receptor, for example, a cytotoxic immune reaction against cells expressing androgen receptor. For example, an anti-tumor response may include lysis of tumor cells by AR-specific CD8+ T cells. Preferably, cellular immune reactions against androgen receptor are induced, with or without humoral immune reactions.

Androgen deprivation therapies (ADT) are therapies that reduce the levels of androgen hormones, or interfere with androgen receptor function/signaling, for example by use of androgen receptor-pathway targeting (e.g. antiandrogens) or chemical castration. Androgen deprivation therapy includes administering an effective amount of at least one androgen receptor pathway-targeting drug. Suitable drugs are known to one skilled in the art and include, but are not limited to, LHRH (or GnRH) analogues (agonists), LHRH (or GnRH) antagonists, AR antagonists, androgen synthesis inhibitors, other AR degrading or blocking agents, and combinations thereof. Suitable ADT include treatment with one or more of the following drugs:

(a) AR antagonists, including, but not limited to, flutamide, nilutamide, bicalutamide, enzalutamide, apalutamide, cyproterone acetate, megestrol acetate, chlormadinone acetate, spironolactone, canrenone, drospirenone, topilutamide (fluridil), cimetidine;

(b) androgen synthesis inhibitors, including, but not limited to, (i) 5α-reductase inhibitors, which include the non-limiting examples of finasteride, dutasteride, alfatradiol, and saw palmetto extract, (ii) CYP17A1 (17α-hydroxylase, 17,20-lyase) inhibitors, which include the non-limiting examples cyproterone acetate, spironolactone, danazol, gestrinone, ketoconazole, abiraterone acetate; (iii) 3β-Hydroxysteroid dehydrogenase inhibitors, which include the non-limiting examples danazol, gestrinone, abiraterone acetate; (iv) 17β-Hydroxysteroid dehydrogenase inhibitors, which include the non-limiting examples danazol, simvastatin; (v) CYP11A1 (cholesterol side-chain cleavage enzyme) inhibitors, which include the non-limiting examples aminoglutethimide, danazol; and (vi) HMG-CoA reductase inhibitors, which include the non-limiting example statins (e.g., atorvastatin, simvastatin);

(c) antigonadotropins including (i) progestogens, such as the non-limiting examples including progesterone, cyproterone acetate, medroxyprogesterone acetate, megestrol acetate, chlormadinone acetate, spironolactone, drospirenone; (ii) estrogens including the non-limiting examples of estradiol, ethinyl estradiol, diethylstilbestrol, conjugated equine estrogens; (iii) GnRH analogues, for example, GnRH agonists, including non-limiting examples buserelin, deslorelin, gonadorelin, goserelin, histrelin, leuprorelin, nafarelin, triptorelin; GnRH antagonists, including non-limiting examples abarelix, cetrorelix, degarelix, ganirelix; and combinations thereof. For example, suitable ADT treatment include, but are not limited to, AR antagonists bicalutamide (Casodex, AstraZeneca®), apalutamide (ARN-509, Janssen), or enzalutamide (Xtandi, Astellas®), GnRH antagonist degarelix (Firmagon, Ferring Pharmaceuticals®), AR degrading agents such as galeterone (Tokai) and the like. In some embodiments, one or more suitable ADT drugs can be used, such as LHRH agonists or antagonists in combination with AR antagonists or degrading agents.

In some embodiments, androgen deprivation therapy (ADT) results in overexpression of the androgen receptor (AR) in the majority of prostate cancer patients' tumors. While this overexpression can promote the development of tumor escape variants, as the present disclosure discusses, it also causes prostate tumor cells to be more susceptible to lysis by AR-specific CD8+ T cells. The Examples demonstrate in vitro that increased AR expression in prostate tumor cells can occur following standard androgen deprivation, or following treatment with commercially available AR antagonists bicalutamide (Casodex, AstraZeneca®) or enzalutamide (Xtandi, Astellas®). Additionally, the Examples demonstrate in vivo that treatment with degarelix (Firmagon, Ferring Pharmaceuticals®), a GnRH antagonist used clinically for androgen deprivation therapy, results in increased AR expression in the MycCaP prostate tumor model. Significantly, while treatment with degarelix alone resulted in a delay in tumor growth, combining this treatment with a vaccine targeting the androgen receptor (pTVG-AR) resulted in a significant delay in tumor growth compared with degarelix treatment alone. Additionally, in animals that develop recurrent disease following combination degarelix and pTVG-AR treatment, tumors have a significant decrease in AR expression, suggesting this may be a biomarker of treatment failure.

Patients undergoing androgen deprivation using a variety of AR-targeting pharmaceutical agents may be immunized with DNA vaccine against the androgen receptor, for example, pTVG-AR, improving the response to these standard therapies. Improved response includes the inhibition or reduction in tumor cell growth or metastasis and/or delay in tumor cell growth or metastasis.

The ADT may be delivered by any suitable dosages and schedule known by one skilled in the art. For example, a non-limiting example includes an LHRH agonist alone or in combination with an antiandrogen (e.g., bicalutamide or enzalutamide). Another non-limiting example is the combination of LHRH agonist and abiraterone and apalutamide.

Non-limiting examples of suitable dosages for LHRH agonists include, for example, Leuprolide 20-25 mg (e.g. 22.5 mg) IM every three months; and/or Goserelin LHRH agonists are typically about 9-12 mg (e.g. 10.8 mg) sc every three months. Non-limiting examples of dosages for LHRH antagonist include Degarelix 240 mg sc once as first dose, and the 80 mg sc every 28 days subsequently; Abiraterone: 1000 mg by mouth daily; Apalutamide: 240 mg by mouth daily; Bicalutamide: 50 mg by mouth daily; and/or Enzalutamide: 160 mg by mouth daily.

In some embodiments, it is contemplated that the dosage or regimen of ADT which is known and understood in the art could possibly be varied from conventional parameters (e.g. reduced amount or frequency of dosage) when combined with the vaccine as described in the present invention.

The vaccine used in the methods of this disclosure may be a recombinant DNA vaccine that encodes the androgen receptor or fragments thereof or a peptide vaccine comprising a polypeptide androgen receptor or fragments thereof. The recombinant DNA vaccine used in the methods of this disclosure may comprise a polynucleotide that encodes a mammalian androgen receptor, the ligand binding domain of the androgen receptor, or a fragment of the androgen receptor. Suitable recombinant DNA vaccine for use is disclosed in U.S. Pat. Nos. 7,910,565 and 8,962,590, entitled "Prostate cancer vaccine," which are incorporated by reference in their entireties. In some embodiments, the recombinant DNA vaccine comprises a polynucleotide that encodes a mammalian androgen receptor, a fragment of the mammalian androgen receptor that comprises the ligand-binding domain, or certain fragments of the ligand-binding domain. The plasmid DNA vaccines, when directly introduced into subjects such as humans in vivo, induce the expression of encoded polypeptides within the subject, and cause the subjects' immune system to become reactive against the polypeptides. The vaccines may be any polynucleotides that are capable of eliciting immune responses to an encoded polypeptide.

In some embodiments, the DNA vaccine comprises pTVG-AR (pTVG-AR or pTVG-ARLBD are the same vector and used herein interchangeably). pTVG-AR is a vector comprising the coding sequence for the ligand-binding domain of the human androgen receptor gene inserted into the pTVG4 vector to create the immunization vector pTVG-AR, as disclosed in U.S. Pat. No. 7,910,565, incorporated by reference in its entirety.

The vaccine can be administered into a subject to elicit an immune response against androgen receptor in the subject. An "effective amount" or an "immunologically effective amount" means that the administration of that amount to a subject, either in a single dose or as part of a series, is effective for inducing an immune reaction against the androgen receptor (and, therefore, against cells expressing the androgen receptor). Further, an "effective amount" as contemplated in the present invention is an amount of vaccine that augments or increases the anti-tumor efficacy of ADT, resulting a delay or inhibitor of prostate tumor growth and metastasis.

Androgen receptor genes are known and have been cloned from many species. For example, the human, mouse, rat, dog, chimpanzee, macaque, and lemur androgen receptor mRNA that correspond to cDNA along with amino acid sequences can be found at GenBank Accession Nos. NM_000044 (cDNA-SEQ ID NO:1 and amino acid sequence-SEQ ID NO:2), NM_013476 (cDNA-SEQ ID NO:3 and amino acid sequence-SEQ ID NO:4), NM_012502 (cDNA-SEQ ID NO:5 and amino acid sequence-SEQ ID NO:6), NM_001003053, NM_001009012, U94179, and U94178, respectively. Androgen receptor genes from other species are also known. These species include but are not limited to Sus scrofa, Astatotilapia burtoni, Gallus gallus, Kryptolebias marmoratus, Alligator mississippiensis, Leucoraja erinacea, Haplochromis burtoni, Pimephales promelas, Dicentrarchus labrax, Gambusia affinis, Micropogonias undulates, Oryzias latipes, Acanthopagrus schlegelii, Rana catesbeiana, Crocuta crocuta, Eulemur fulvus collaris, and Anguilla japonica (see GenBank Accession Nos. NM_214314 (or AF161717), AY082342, NM_001040090, DQ339105, AB186356, DQ382340, AF121257, AY727529, AY647256, AB099303, AY701761, AB076399, AY219702, AY324231, AY128705, U94178, and AB023960, respectively). The ligand-binding domains of androgen receptors are well known in the art. For the purpose of the present invention, the ligand-binding domain of the human androgen receptor refers to a polypeptide that starts at any amino acid from amino acid positions 651 to 681 and ends at any amino acid from amino acid positions 900 to 920. For example, human androgen receptor or a fragment of the human androgen receptor that comprises amino acids 681-900 as well as DNA vaccines containing a polynucleotide encoding the above are suitable vaccines. As will be readily recognized by one of ordinary skill in the art, any DNA sequence that encodes a ligand-binding domain or a larger fragment of an androgen receptor including the full-length receptor from one of the above species as well as other animals is suitable for the present invention.

Pharmaceutically acceptable carriers are well known to those of ordinary skill in the art (Amon, R. (Ed.) Synthetic Vaccines 1:83-92, CRC Press, Inc., Boca Raton, Fla., 1987). They include liquid media suitable for use as vehicles to introduce the peptide or polynucleotide into a patient but should not in themselves induce the production of antibodies harmful to the individual receiving the composition. An example of such liquid media is saline solution.

Moreover, the vaccine may also contain an adjuvant for stimulating the immune response and thereby enhancing the effect of the vaccine. Suitable adjuvants are known in the art and include, but are not limited to, GM-CSF, Montanide, or saponin-derivative adjuvants.

According to another embodiment, the DNA vaccine comprises a polynucleotide operatively linked to a transcriptional regulatory element (e.g., a promoter such as a heterologous promoter) wherein the polynucleotide encodes a member selected from (i) a mammalian androgen receptor (e.g., a human androgen receptor), (ii) a fragment of the androgen receptor that comprises the ligand-binding domain, (iii) a fragment of the ligand-binding domain defined by SEQ ID NO:9 (LLLFSIIPV, amino acids 811-819 of SEQ ID NO:2); (iv) a fragment of the ligand-binding domain defined by SEQ ID NO:10 (RMLYFAPDLV, amino acids 761-770 of SEQ ID NO:2), (v) a fragment of the ligand-binding domain defined by SEQ ID NO:11 (FLCMKALLL, amino acids 805-813 of SEQ ID NO:2), and (vi) a fragment of the ligand-binding domain defined by SEQ ID NO:12 (QLTKLLDSV, amino acids 859-867 of SEQ ID NO:2), wherein administration of said vaccine to a subject induces a cytotoxic immune reaction against cells expressing androgen receptor.

The DNA vaccine may comprise the polynucleotide directly linked to a transcriptional regulatory element that promotes the expression of the protein (e.g., androgen receptor or fragment thereof) within cells of the subject. Suitable transcriptional regulatory element (e.g., a promoter such as a heterologous promoter) are known in the art and include, but are not limited to, CMV promoter, Rous sarcoma virus (RSV) promoter, the simian virus 40 (SV40) promoter, the human elongation factor-1α (EF-1α) promoter, and the human ubiquitin C (UbC) promoter, among others.

The vaccine is suitably administered by intradermal, intramuscular, subcutaneous, or intravascular (including intravenous and intraarterial) administration to a mammal such as a human. In another aspect, the DNA vaccine is suitable for administration by muscle or skin electroporation to increase uptake of the DNA at the site of immunization.

The vaccines can be used in a prime-boost strategy in connection with the ADT therapy to induce robust and long-lasting immune response to androgen receptor. Priming and boosting vaccination protocols based on repeated injections of the same antigenic construct are well known and result in strong CTL responses. In general, the first dose may not produce protective immunity, but only "primes" the immune system. A protective immune response develops after the second or third dose.

The vaccine described herein may be provided in an effective amount to augment or increase the efficacy of ADT treatment, which can be seen by a delay, reduction or inhibition of prostate tumor cell growth or metastasis.

In one embodiment, the vaccines may be used in a conventional prime-boost strategy, in which the same antigen is administered to the animal in multiple doses. In a preferred embodiment, the DNA or peptide vaccine is used in one or more inoculations. These boosts are performed according to conventional techniques, and can be further optimized empirically in terms of schedule of administration, route of administration, choice of adjuvant, dose, and potential sequence when administered with another vaccine, therapy or homologous vaccine.

In one embodiment, the vaccine is administered every two weeks to every three months. In some embodiments, the vaccine is administered for at least 6 weeks, alternatively for at least 10 weeks, alternatively for at least 15 weeks, alternatively for at least 20 weeks, alternatively for at least 25 weeks, alternatively for at least 30 weeks, alternatively for at least 35 weeks, alternatively for at least 40 weeks, alternatively for at least 45 weeks, alternatively at least 48 weeks, alternatively for at least 50 weeks, alternatively for at least a year, alternatively for at least 18 months, alternatively for at least 20 months and can include any time in between (for example, 16 weeks 17 weeks, 18 weeks, 19 weeks, 24 weeks, etc). In some embodiments, the vaccine is administered biweekly for about 6 to about 14 weeks and subsequently administered quarterly for at least a year. In some embodiments, the vaccine is administered biweekly for about 6 to about 14 weeks and subsequently administered quarterly (i.e. every three months) for at least 18 months.

Suitable dosages of the DNA vaccine are known in the art, and include, but are not limited to, about 10 mcg to about 1 mg of DNA per dosage.

In some embodiments, the ADT and recombinant vaccine are administered concurrently. In other embodiments, the subject is treated with ADT and subsequently treated with the recombinant vaccine. The time period between the ADT and recombinant vaccine administration may be a short duration (e.g., hours or days) or may be of a longer duration (e.g. weeks or months). In some embodiments, the term concurrently means that the two components are administered in close timing to each other (e.g. within hours or on the same day), but may be administered by different routes of administration (e.g. ADT orally and vaccine by injection). In some embodiments, the administration are separate, e.g. separated by hours or days in between the vaccine and the ADT. In some embodiments, the vaccine and the ADT are administered over the same time period but using different regimens that require administration on different days. Suitable regimens are discussed more herein, for example, a regimen where the vaccine is administered for a period of time before beginning dose regimen for ADT.

In some embodiments, the recombinant DNA vaccine is administered prior to androgen deprivation therapy. In some embodiments, the DNA vaccine is administered every other week for 2-24 weeks before start of administration of ADT, and in some embodiments, the DNA vaccine administration is continued every 2-16 weeks during ADT therapy. Not to be bound by any theory, but the administration of the DNA vaccine prior to administration of androgen deprivation therapy may lead to preferred immune and anti-tumor responses as it has been shown that giving ADT prior to immunization may directly interfere with the priming of T cell responses. One skilled in the art will be able to determine a preferred regimen of ADT and vaccine administration.

In some embodiments, the subject is a mammal, preferably a human.

In some embodiments, the methods of the disclosure further comprise administering to the subject an effective amount of a checkpoint pathway inhibitor in addition to the vaccine against androgen receptor to augment ADT treatment. In one example, the checkpoint pathway inhibitor is a PD-pathway inhibitor. Suitable PD-pathway inhibitors are known in the art. In some embodiments, the PD-pathway inhibitor is an anti-PD-1 blocking antibody or an anti-PD-L1 antibody.

Using different tumor antigen systems we have found that DNA vaccination can elicit PD-L1 expression in tumors as a result of tumor-specific T cells elicited that secrete IFNγ. Specifically, tumors expressing a model antigen had an increase in PD-L1 expression following immunization with a DNA vaccine encoding that antigen (Rekoske, B. T., H. A. Smith, B. M. Olson, B. B. Maricque, and D. G. McNeel. (2015). "PD-1 or PD-L1 Blockade Restores Antitumor Efficacy Following SSX2 Epitope-Modified DNA Vaccine Immunization." *Cancer Immunol Res.* 3:946-55). If the immunization was modified to elicit CD8+ T cells with higher PD-1 expression, this resulted in an inferior anti-tumor response.

Figures 10A, 10B:
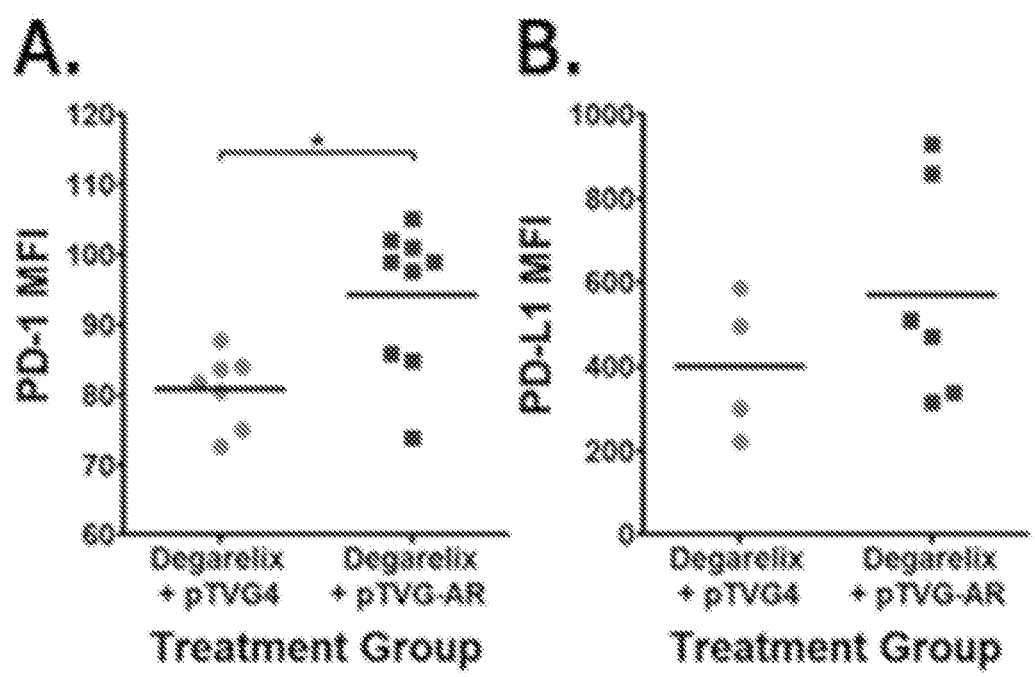
FIG. 10A shows that CD8+ T cells from MycCaP tumor-bearing animals treated with ADT and immunized with pTVG-AR have elevated PD-1 expression.
FIG. 10B shows that recurrent tumors had elevated PD-L1 expression.
Figures 10C, 10D:
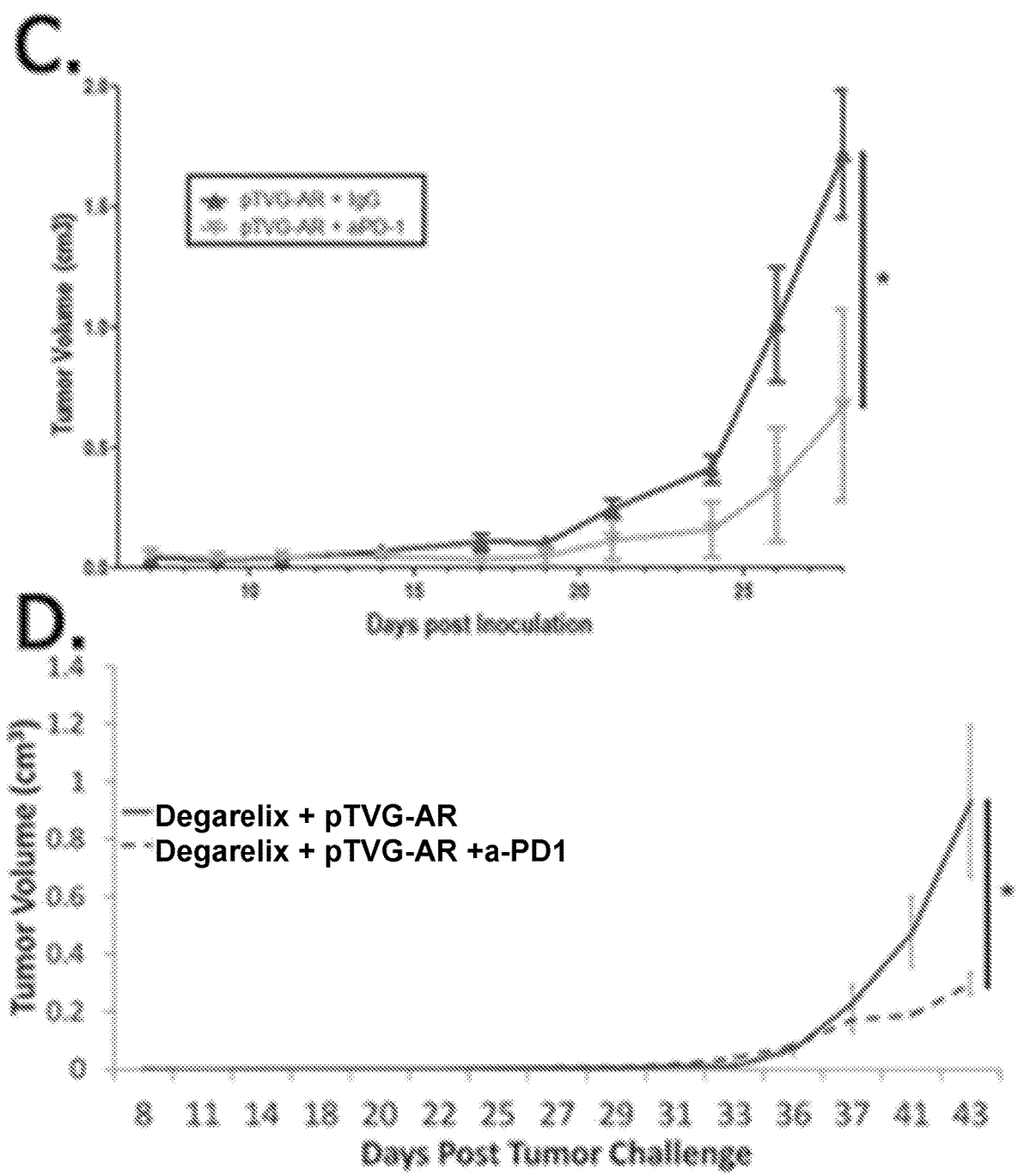
FIG. 10C depicts delay in tumor growth in mice with AR-targeted immunization combined along with a PD-1 blocking antibody compared to immunization with pTVG-AR alone.
FIG. 10D shows that combining AD with AR-directed immunization and PD-1 blockade further delayed tumor growth.

The Examples below demonstrate that targeting the PD-1/PD-L1 pathway in combination with an AR-targeting vaccine may reduce or prevent tumor-mediated immune suppression. In MycCaP tumor-bearing animals treated with AD and immunized with pTVG-AR, CD8+ T cells were found to have elevated PD-1 expression (FIG. 10A). Additionally, some recurrent tumors had elevated PD-L1 expression (FIG. 10B). When AR-targeted immunization was combined along with a PD-1 blocking antibody, this treatment significantly delayed tumor growth compared to immunization with pTVG-AR alone (FIG. 10C). Furthermore, combining ADT with AR-directed immunization and PD-1 blockade further delayed tumor growth (FIG. 10D). Thus, the combination of vaccination and ADT with anti-PD-1 or anti-PD-L1 antibody treatment results in a greater anti-tumor response and may lead to the eradication of tumors. The addition of anti-PD-1 or anti-PD-L1 antibody treatment augments or increases the immune response to androgen receptor. For example, one non-limiting example of a method of treatment includes combination ADT comprising LHRH, abiraterone, apalutamide or a combination thereof with the AR vaccine and anti-PD-1 antibody.

Many different possible scenarios are envisioned for the methods of the present invention including treatment regimens using the double combination (DNA vaccine and ADT) and triple combination therapy (DNA Vaccine, PD-1 pathway inhibitor and ADT) contemplated in this invention. In these scenarios the double and triple combinations do not have to be co-administered and may just be administered over the same period of time in suitable dosage regimens. In other embodiments, the start of each therapy is staggered to provide the most efficacious treatment regimen (e.g. administration of at least 2 or more vaccine doses before the start of ADT therapy). In some embodiments, the method of treating includes administering the triple combination for a period of time followed by administration of the double combination for a second period of time. In other embodiments, the method of treating includes a period of time administering the double combination followed by a period of time administering the triple combination therapy. In other embodiments, the method of treating includes a period of time administering the double or triple combination which includes within that time a period in which one or more of the treatments is not administered while the other therapies are maintained. For example, in the DNA vaccine and PD-1 pathway inhibitor may be administered weekly or biweekly for 2-12 weeks before ADT is administered, whereby DNA vaccine, PD-1 pathway inhibitor and ADT are all administered for at least 12-48 additional weeks, after which time ADT therapy may be stopped for a period of time during with booster administration of the vaccine may continue with or without the PD-1 pathway inhibitor. In some instances, ADT therapy may be re-initiated weeks to months later. Other suitable combinations of the therapies, treatment times and dosing regimens are contemplated to be determined by one skilled in the art.

In some embodiments, the double combination therapy of DNA vaccine and ADT are contemplated. In some embodiments, the DNA vaccine is administered at least once (i.e. from 1-12 times) weekly or bi-weekly before the beginning of ADT. Starting the vaccine before ADT treatment may have some advantages in priming the immune system to be activated against cells expressing androgen receptor, which we have found is overexpressed in tumor cells after ADT treatment. This allows for a more robust and increased immune response to tumor cells resulting in a delay or decreased tumor growth. In some embodiments, ADT therapy is started before the administration of the DNA vaccine, e.g. for at least one month or more before DNA vaccine is administered.

In some embodiments, the ADT administration can also be intermittent. During intermittent ADT administration, the PSA number in a subject may be monitored to determine if ADT therapy should be stopped and/or started again. For example, ADT is stopped once the PSA number is lowered to a suitable level and stabilized; and ADT is restarted when the PSA number increases again (sometimes months, maybe years later). Further, the use of the DNA vaccine may include dosages where the vaccine is given periodically (e.g. every 2 week to every 3 months) over the first year to elicit an anti-tumor response and then administered occasionally (e.g. 3 months or more) as maintenance boosters to maintain an anti-tumor immune response in combination with continuous or intermittent ADT administration.

In some embodiments, the DNA vaccine, PD-1 pathway inhibitor, and ADT are each administered separately and each are administered over different overlapping time periods. In some instances, all three are administered over the same time period. In some embodiments, all three treatments are administered over the same time period constantly but at different timing intervals. In some embodiments, all three treatments are not constantly administered (e.g. there is period of time in which one or more of the treatments are not administered). In some embodiments, each of the treatments is provided in different dosages that are spaced out at different times after the start of treatment. For example, the DNA vaccine may be administered before the start of treatment with the PD-1 pathway inhibitor and before the start of ADT treatment. In some examples, the DNA vaccine may be administered once every 1-12 weeks, for at least 6 weeks or more, for example once every week or once every other week for 1-24 weeks followed by once every 3-8 weeks for at least an additional 24 weeks or more. In another example, the DNA vaccine and PD-1 pathway inhibitor may be administered on the same schedule of administration before the beginning of ADT treatment (e.g. every 2 weeks for 6-36 week, followed by every 4-6 weeks for at least an additional 6-36 weeks, followed by booster administration every 12-24 weeks for at least an additional year). Other suitable combinations of dosing schedules is contemplated.

In some embodiments, the length of each treatment (DNA vaccine, PD-1 pathway inhibitor and ADT) and period over which treatment is provided for at least a portion of time. In some embodiments, one or more of the treatments are administered over the same time period. For example, the DNA vaccine, PD-1 pathway inhibitor may be administered at different dosages and at different times over the course of months to years, while the ADT can be administered by known protocols over some or all of the same time period of months or years.

In some embodiments, the DNA vaccine and the PD-1 pathway inhibitor are administered in multiple dosages prior to the start of the ADT and continue during ADT administration. In some embodiments, the combination of treatment is administered as follows:

vaccine and PD-1 pathway inhibitor administered every 2-4 weeks (e.g. 2 weeks) for at least 8 to 16 weeks, followed by administration of the vaccine and PD-1 pathway inhibitor every 4 weeks for at least 8 to 16 additional weeks, followed by administration of the vaccine and PD-1 pathway inhibitor every 12 weeks (or alternatively every 3 months) for at least an additional 24 weeks; and ADT is administered beginning between week 10 and week 14 after start of the vaccine and PD-1 pathway inhibitor initial administration, and is administered every 12 weeks for at least 4 additional treatment times (i.e. for at least 48 weeks).

In a preferred embodiment, the vaccine is a DNA vaccine against an androgen receptor and the PD-1 pathway inhibitor is an anti-PD-1 antibody, and the ADT is leuprolide depot 22.5 mg intramuscular administration or goserelin 10.8 mg subcutaneous administration. A suitable dosage regimen is found in FIG. 16, wherein the DNA vaccine and PD-1 pathway inhibitor is administered every 2 weeks for the first 12 weeks, followed by administration every 4 weeks for an additional 12 weeks, and subsequently followed by administration every 12 weeks for at least an additional 24-48 weeks. In this dosage regimen, the ADT is administered at 12 weeks, 24 weeks, 36 weeks and 48 weeks after the initial vaccine/PD-1 inhibitor treatment. This regimen can be extended to at least a year or more in order to treat the tumor.

In some embodiments, the disclosure provides a method of increasing the efficacy of androgen deprivation therapy in a subject with prostate cancer comprising administering to the subject an effective amount of a recombinant DNA vaccine comprising a polynucleotide operably linked to a transcriptional regulatory element wherein the polynucleotide encodes an androgen receptor or a fragment of the androgen receptor, wherein the method inhibits, delays or reduces the growth of the prostate cancer. In some embodiments, the method further comprises administering to the subject an effective amount of a PD-pathway inhibitor.

The subject may have previously been diagnosed as having prostate cancer. In some embodiments, the prostate cancer may be in any stage, for example, early stage prostate cancer or newly diagnosed prostate cancer. In some embodiments, the prostate cancer may be metastatic prostate cancer. In another embodiment, the prostate cancer is castration resistant prostate cancer (mCRPC).

Some embodiments provide a kit for treating prostate cancer. The kit comprises androgen deprivation therapy and a vaccine (for example a DNA vaccine) that elicits an anti-androgen receptor immune response. A set of instructions on the dosages and regiments for administering the ADT and recombinant DNA vaccine may also be provided. In some embodiments, the androgen receptor therapy consists of one or more drugs that target the AR pathway by interfering with AR expression or signaling. Suitable vaccines and drugs are discussed above.

In another embodiment the kit comprises androgen deprivation therapy, a vaccine (for example a DNA vaccine) that elicits an anti-androgen receptor immune response and a PD-1 pathway inhibitor (such as a PD-1 antibody). A set of instructions on the dosages and regimen for each treatment may be provided.

The invention will be more fully understood upon consideration of the following non-limiting examples. Each publication, patent, and patent publication cited in this disclosure is incorporated in reference herein in its entirety.

Example 1

Androgen Deprivation Increases Androgen Receptor (AR) Expression and Enhances Tumor Cell Susceptibility to AR-Specific T-Cell Responses This Example demonstrates that Androgen deprivation results in increased full length AR expression in tumor cells (22Rv1 cells), whether deprivation was for a short or extended period of time. Co-culture of AR peptide-specific CD8+ T cells with HLA-A2-expressing tumor cells resulted in increased T-cell activation, cytokine expression, and cytotoxicity assays.

Materials and Methods

Cell Culture

22Rv1, LNCaP, PC3, and DU145 cells were obtained from ATCC, and their identity and lack of *mycoplasma* contamination was confirmed by DDC Medical. Cells were cultured in RPMI-1640 medium with 200 U/mL penicillin/streptomycin, 1 mM sodium pyruvate, and 0.1 mM β-mercaptoethanol. This base medium was supplemented with either 10% complete FCS (RPMI/FCS), or 10% charcoal-stripped serum (RPMI/CSS) to generate androgen-deprived culture medium. Charcoal-stripped serum was generated by incubating dextran-coated charcoal with heat-inactivated FCS and incubating overnight at 4° C., followed by centrifugation and sterile filtration, followed by analysis for testosterone by Testosterone AccuBind ELISA (Monobind).

Androgen Receptor Enzyme-Linked Immunosorbent Assay (ELISA)

Cultured prostate cancer cells were collected, cell lysates prepared, and analyzed for protein expression using the PathScan androgen receptor (AR) ELISA per manufacturer's instructions (Cell Signaling Technology). Briefly, microwell strips (pre-coated with anti-AR antibody) were coated with 2 mg/mL protein lysates in triplicate, and incubated overnight at 4° C. The following day, AR was detected using a detection antibody followed by HRP-linked secondary antibody and TMB substrate development. A standard curve using purified AR LBD protein (Invitrogen) was generated, and used to obtain relative AR concentration per mg cell lysate.

Androgen Receptor Quantitative Real-Time PCR

Cultured prostate cancer cells were collected, RNA was prepared using Qiagen RNeasy RNA purification system, common concentrations of RNA was used to synthesize cDNA using iScript cDNA synthesis kid (BioRad) and used as a template for qPCR reactions using SsoFast qPCR supermix (BioRad). Reactions were run a Bio-Rad MyiQ thermocycler, using an annealing temperature of 60° C. and 40 cycles. Primer sets:

```
AR-FL_Fwd
                                     (SEQ ID NO: 7)
(ACATCAAGGAACTCGATCGTATCATTGC);

AR-FL_Rev
                                     (SEQ ID NO: 8)
(TTGGGCACTTGCACAGAGAT);

AR-V7_Fwd
                                    (SEQ ID NO: 13)
(CCATCTTGTCGTCTTCGGAAATGTTATGAAGC);

AR-V7_Rev
                                    (SEQ ID NO: 14)
(TTTGAATGAGGCAAGTCAGCCTTTCT);

β-actin_Fwd
                                    (SEQ ID NO: 15)
(TCATGAAGTGTGACGTTGACATCCGT);

β-actin_Rev
                                    (SEQ ID NO: 16)
(CTTAGAAGCATTTGCGGTGCACGATG).
```

Results were analyzed by the $2^{-\Delta Ct}$ method relative to β-actin as a control gene, and fold induction over FCS-treated cells was calculated using the $2^{-\Delta\Delta Ct}$ method, as published [6].

Generation and Validation of HLA-A2-Expressing 22Rv1 Cells

22Rv1 cells cultured greater than six months in RPMI/FCS or RPMI/CSS were diluted into 96-well flat bottom plates at a concentration of 50 cells/well, and transfected with a lentivirus encoding the human HLA-A2 complex. Cells were expanded, stained with HLA-A2-FITC (Biolegend), and sorted for HLA-A2+ events (FACSAria Cell Sorter, BD Biosciences). HLA-A2+22Rv1/FCS and 22Rv1/CSS cells were expanded, and AR protein and mRNA expression was validated as above, and HLA-A2 and PD-L1 expression was evaluated by flow cytometry.

Mouse Immunology Assays

For mouse immunology studies, HHDII-DR1 heterozygous mice were immunized subcutaneously on the right hind flank with 100 μg of the AR811 peptide given with 200 μl Complete Freund's Adjuvant (Sigma), as published (Olson et al., *Cancer Immunol, Immunother.* (2011), 33: 639-647). Seven days later, splenocytes were collected, restimulated for six days with AR811 peptide, and used for intracellular cytokine staining assays and cytotoxicity assays. For intracellular cytokine staining, 200,000 splenocytes were stimulated for 18 hours with media alone, 2000 22Rv1/FCS cells, 2000 22Rv1/CSS cells, or a PMA/Ionomycin positive control. Cells were treated with monensin (GolgiStop, 2 μM, BD Biosciences) for four hours at 37° C./5% $CO_2$. Cells were then stained with fluorescently-labeled CD3, CD4, CD8, and CD69 antibodies, and after fixation and permeabilization, intracellular staining was conducted using fluorescently-labeled antibodies for IFNγ and TNFα (BD Biosciences), or the corresponding isotype controls. Cells were subsequently analyzed using an LSR II flow cytometer (BD Biosciences), and events were analyzed by gating CD3+CD8+ splenocytes and analyzing this population for expression of IFNγ and/or TNFα, as well as surface CD69 expression. Cytotoxicity assays were performed as has been previously described (Smith et al., Canc. Res. (2011), 71: 6785-6795). Briefly, restimulated splenocytes were cultured with 22Rv1/FCS or 22Rv1/CSS target cell lines for 4-6 hours, after which LDH release was calculated using a variation of the Cytotox 96 Assay kid (Promega). The optical density (OD) signal contributed by the media alone was subtracted from all values. All sample conditions were evaluated in triplicate, with the standard error shown.

Human Immunology Assays

For human immunology studies, human T-cell cultures were generated as has been previously described (Olson et al., *Cancer Immunol, Immunother.* (2011), 33: 639-647). Briefly, PBMC samples from HLA-A2+ prostate cancer patients were cultured with irradiated peptide-pulsed antigen-presenting cells (either autologous DCs, PBMC, or lymphoblastoid B-cell lines). After 24 hours, cells were treated with 10 U/mL IL-2, and restimulated weekly with irradiated peptide-pulsed APCs, and after 2-8 in vitro stimulations, cultures were tested for cytolytic activity using cytotoxicity assays. AR805 peptide-specific T cells were subsequently used for intracellular cytokine staining assays and cytotoxicity assays. For intracellular cytokine staining, assays were conducted as above, but using fluorescently-labeled antibodies for intracellular IFNγ, TNFα, IL-2, and granzyme B (GrB), or the corresponding isotype controls. Cells were subsequently analyzed using an LSR II flow cytometer, and events were analyzed by gating CD3+CD8+ T-cells and analyzing this population for expression of IFNγ, TNFα, IL-2, and/or GrB, as well as surface CD69 and CD107a expression. Cytotoxicity assays were performed as above and has been previously described (Smith et al., Canc. Res. (2011), 71: 6785-6795).

Results

Androgen Deprivation Increases AR Protein Expression in Some Prostate Cancer Cell Lines In Vitro.

DU145, PC3, LNCaP, and 22Rv1 cells were cultured under androgen-replete (FCS; media supplemented with complete FCS) or androgen-deprived (CSS; charcoal-stripped serum) conditions for 1, 3, 5, or 7 days or for at least three months (LT; long-term). Protein lysates were collected and analyzed for AR protein expression by ELISA as shown in FIG. 1A-D. * indicates $p<0.05$ by Student's t-test.

Androgen Deprivation Induces a Transient Increase in AR-V7 mRNA Expression and Sustained Overexpression of Full-Length AR mRNA.

Figure 2:
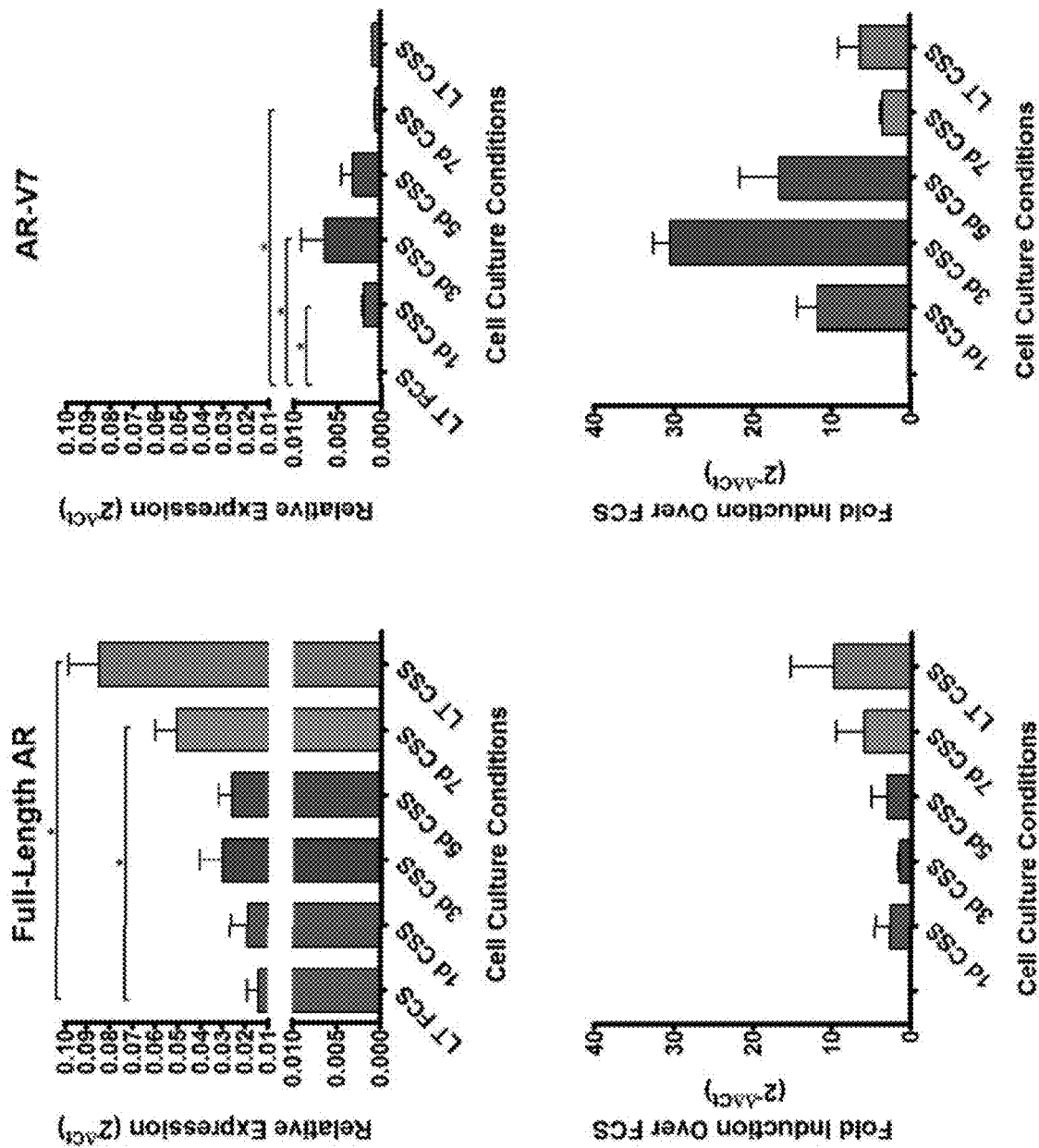
FIG. 2 shows that long-term androgen deprivation increases full-length AR expression, and short-term androgen deprivation induces a transient increase in AR-V7 expression. Top Panels: relative expression (normalized to β-actin control). Bottom panels: fold induction of expression over long-term FCS-cultured 22rv1 cells. * indicates $p<0.05$ by Student's t-test.

22Rv1 cells were cultured under androgen-replete or androgen-deprived conditions for 1, 3, 5, or 7 days or for at least three months. RNA was isolated and used to synthesize cDNA, and cDNA was used as the template for qRT-PCR reactions for either full-length AR (FIGS. 2A and 2C, left panels) or AR-V7 (FIGS. 2B and 2D, right panels) expression. Top Panels: relative expression (normalized to β-actin control). Bottom panels: fold induction of expression over long-term FCS-cultured 22rv1 cells. * indicates $p<0.05$ by Student's t-test.

ARLBD Peptide-Specific T-Cells have Increased Levels of T-Cell Activation, Th1 Polyfunctional Cytokine Expression, and Cytotoxicity Against Androgen-Deprived Prostate Cancer Cells than Cells Cultured in Androgen-Replete Conditions.

Figures 3A, 3B:
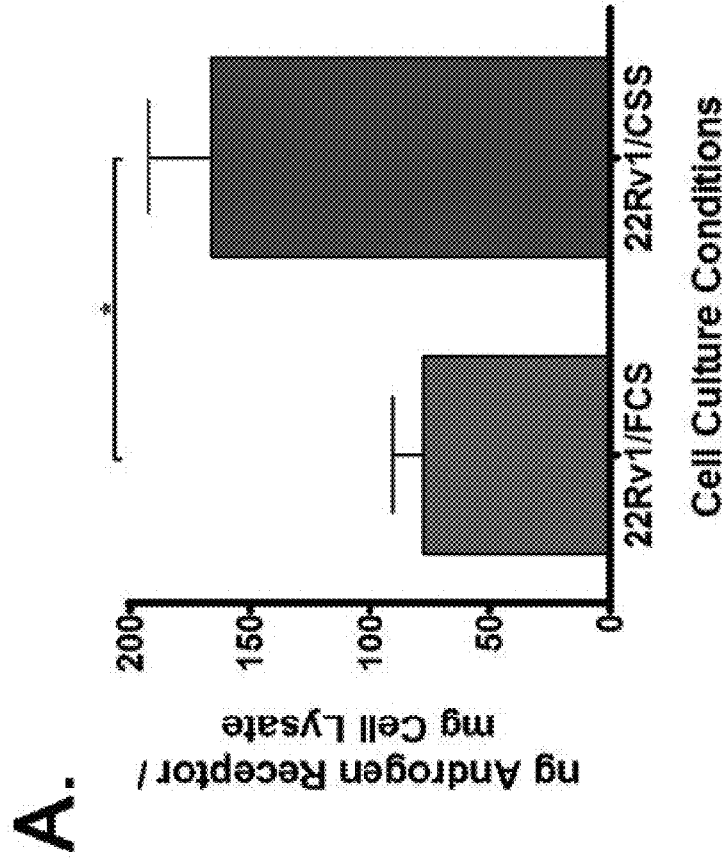
FIG. 3A-D shows that HLA-A2-expressing, long-term androgen-deprived 22Rv1 cells have increased androgen receptor expression. 22Rv1/FCS (fetal calf serum-containing medium, containing androgen) and 22Rv1/CSS (charcoal stripped serum-containing medium, androgen depleted) cell lines (or non-HLA-A2-transfected 22 Rv1 controls) were evaluated for AR protein expression by ELISA (FIG. 3A), RNA expression by qRT-PCR FIG. 3B), HLA-A2 expression FIG. 3C), and PD-L1 expression (FIG. 3D) by flow cytometry (blue: 22 Rv1/FCS; red: 22Rv1/CSS; black: wild-type 22Rv1; grey: IgG-stained 22Rv1). * indicates $p<0.05$ by Student's t-test.
Figure 3C:
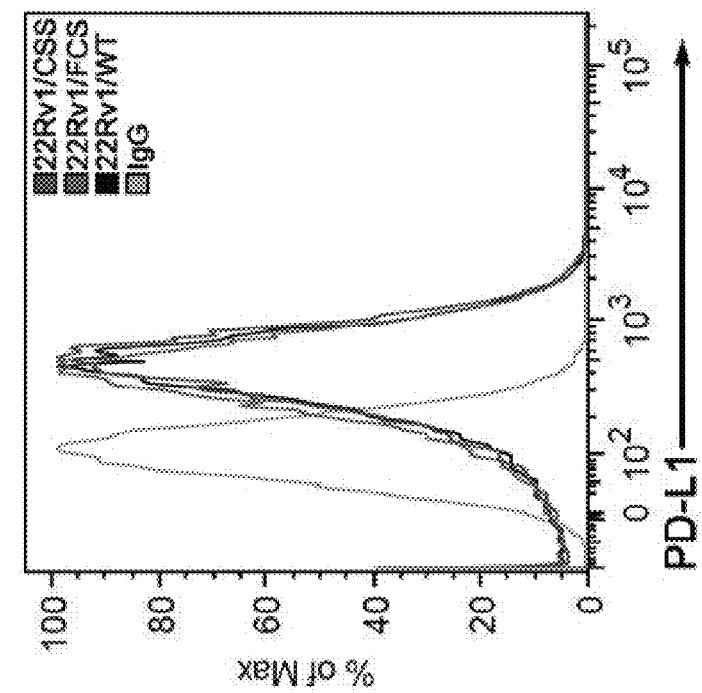
Figure 3D:
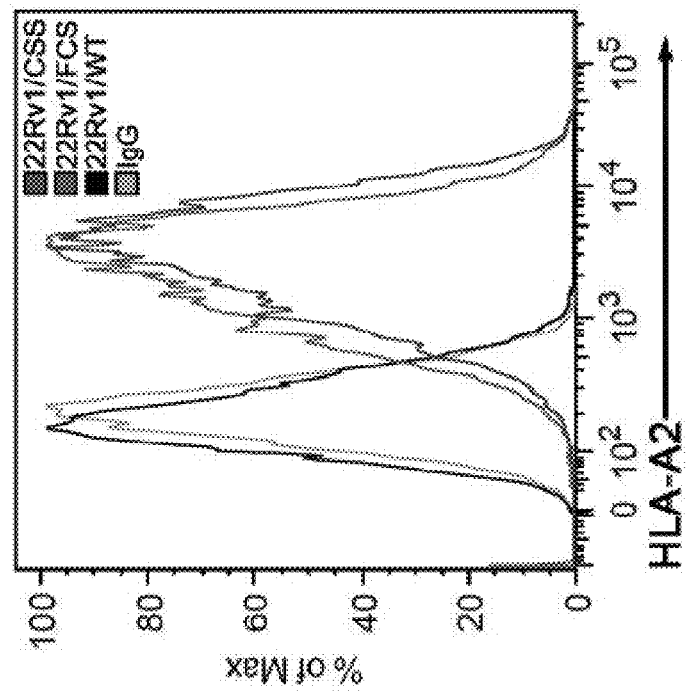

22Rv1 cells were cultured greater than six months in androgen-replete (FCS) or androgen-deprived (CSS) conditions, transfected with a lentivirus encoding HLA-A2, and sorted for HLA-A2-expressing cells by flow cytometry. Subsequent 22Rv1/FCS and 22Rv1/CSS cell lines (or non-HLA-A2-transfected 22 Rv1 controls) were evaluated for AR protein expression by ELISA (FIG. 3A), RNA expression by qRT-PCR (FIG. 3B), HLA-A2 expression (FIG. 3C), and PD-L1 expression (FIG. 3D) by flow cytometry (blue: 22 Rv1/FCS; red: 22Rv1/CSS; black: wild-type 22Rv1; grey: IgG-stained 22Rv1). * indicates $p<0.05$ by Student's t-test.

AR811 Peptide-Immunized Mice have Increased Cytokine Expression, T-Cell Activation, and Cytotoxicity when Exposed to Androgen-Deprived 22Rv1 Cells.

Figure 4A:
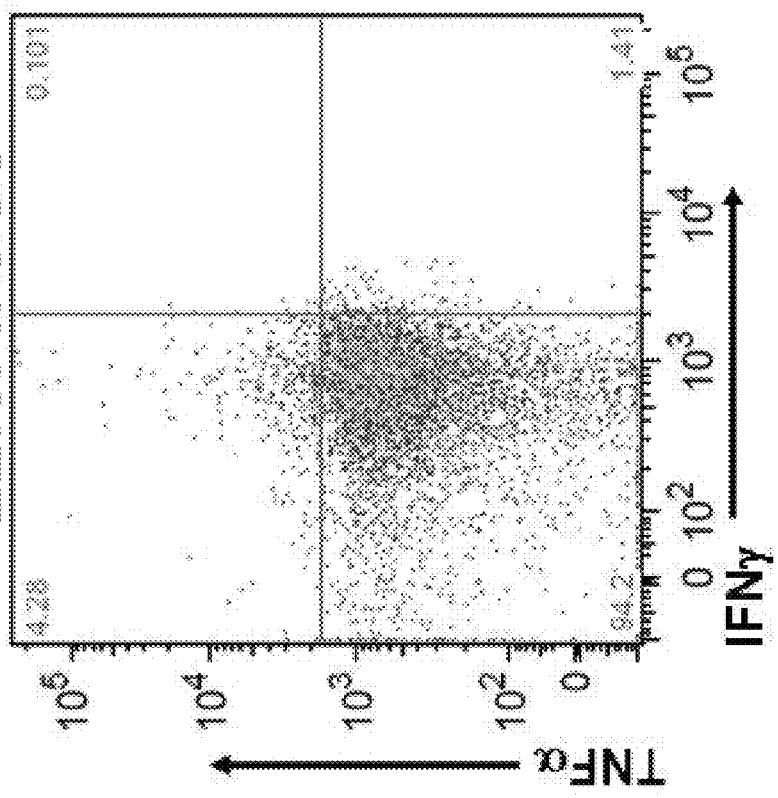
FIG. 4A-B depict intracellular cytokine staining of splenocytes cultured with 22Rv1/FCS (4A) or 22Rv1/CSS (blue) or 22Rv1/FCS (red) cells (mean fluorescent intensity quantified in inset—* indicates $p<0.05$ by Student's t-test).
Figure 4B:
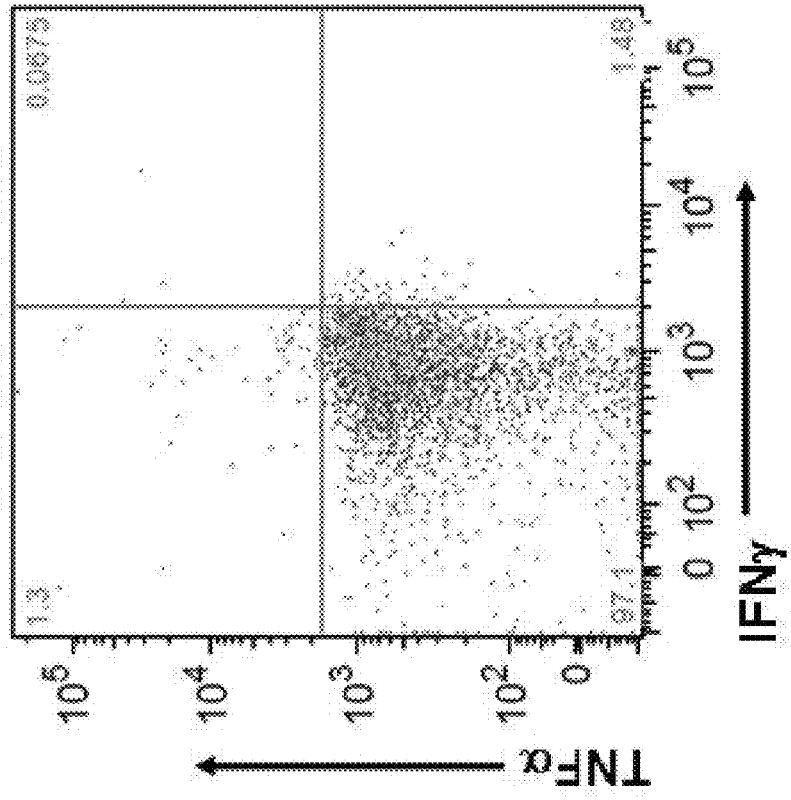
Figure 4C:
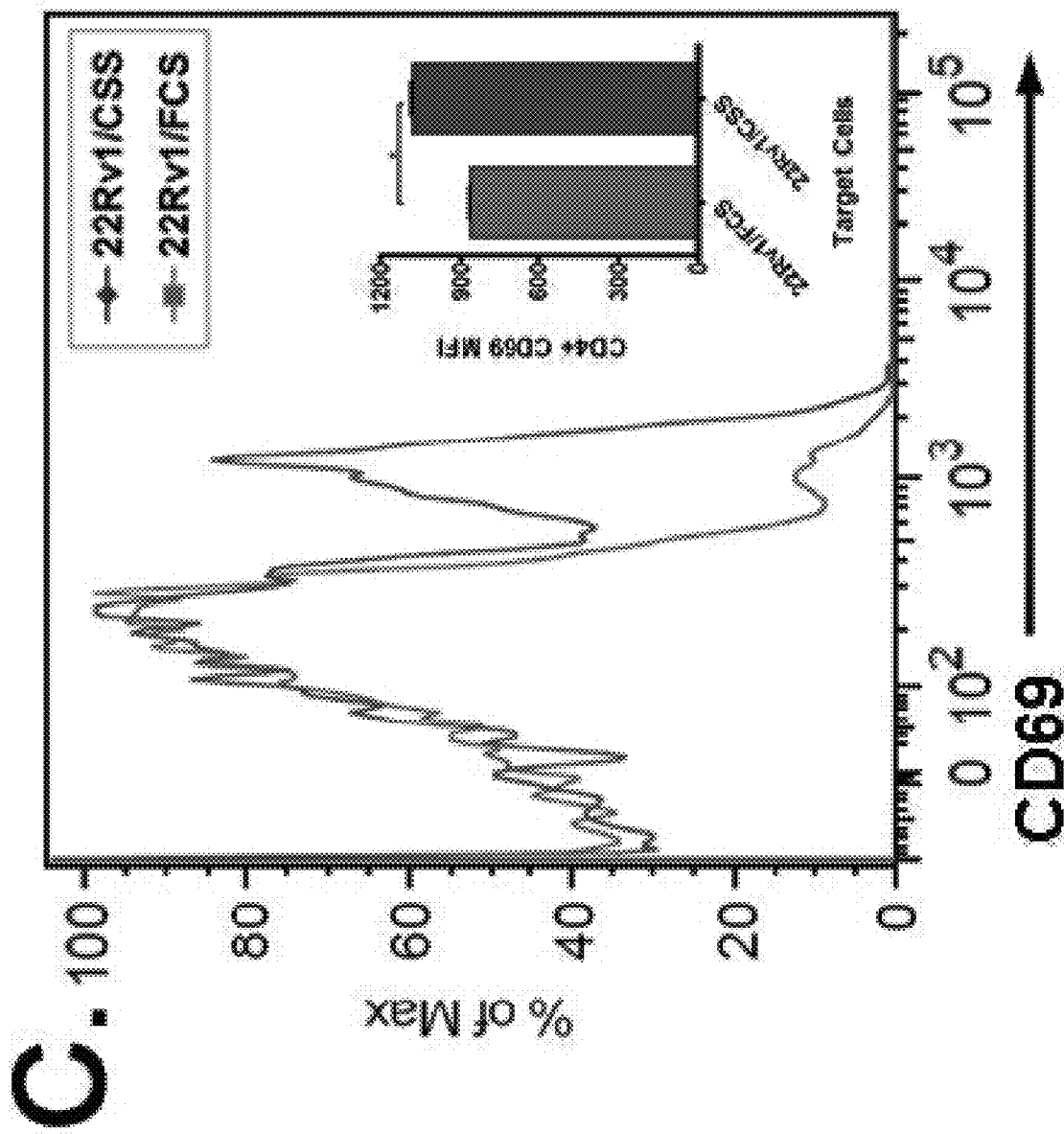
FIG. 4C depicts CD69 expression of splenocytes cultured with 22Rv1/CSS (blue) or 22Rv1/FCS (red) cells (mean fluorescent intensity quantified in inset—* indicates p, 0.05 by Student's t-test).
Figure 4D:
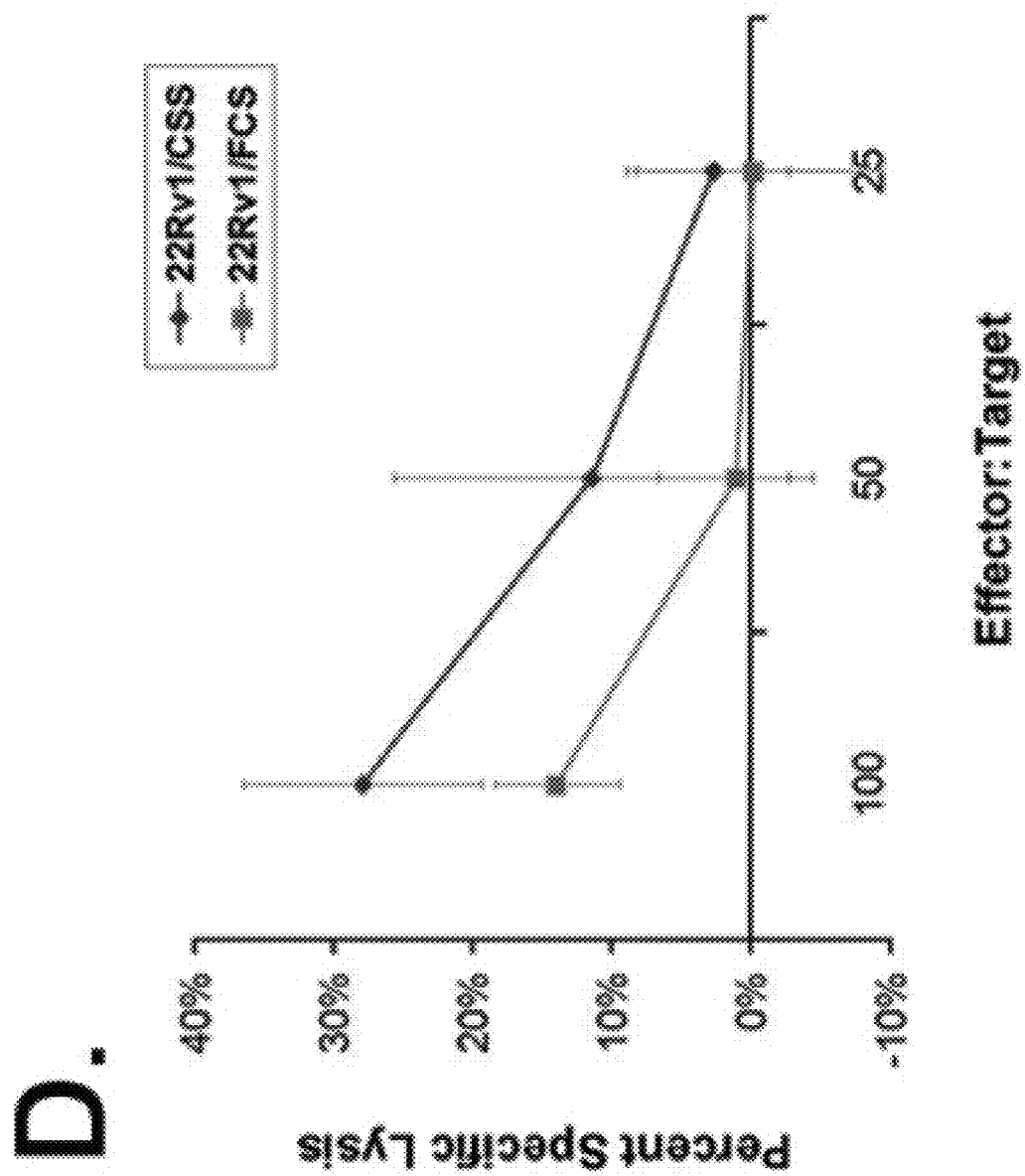
FIG. 4D depicts cytotoxicity of splenocytes cultured with 22Rv1/CSS (blue) or 22Rv1/FCS (red) cells.

Splenocytes from AR811 peptide-immunized HHDII-DR1 heterozygous mice were evaluated for immune responses against HLA-A2-expressing 22Rv1/FCS or 22Rv1/CSS cells. FIG. 4A-B shows intracellular cytokine staining of splenocytes cultured with 22Rv1/FCS (FIG. 4A) or 22Rv1/CSS (FIG. 4B). FIG. 4C depicts CD69 expression of splenocytes cultured with 22Rv1/CSS (blue) or 22Rv1/FCS (red) cells (mean fluorescent intensity quantified in inset—* indicates p<0.05 by Student's t-test). FIG. 4D shows cytotoxicity of splenocytes cultured with 22Rv1/CSS (blue) or 22Rv1/FCS (red) cells.

Figure 5A:
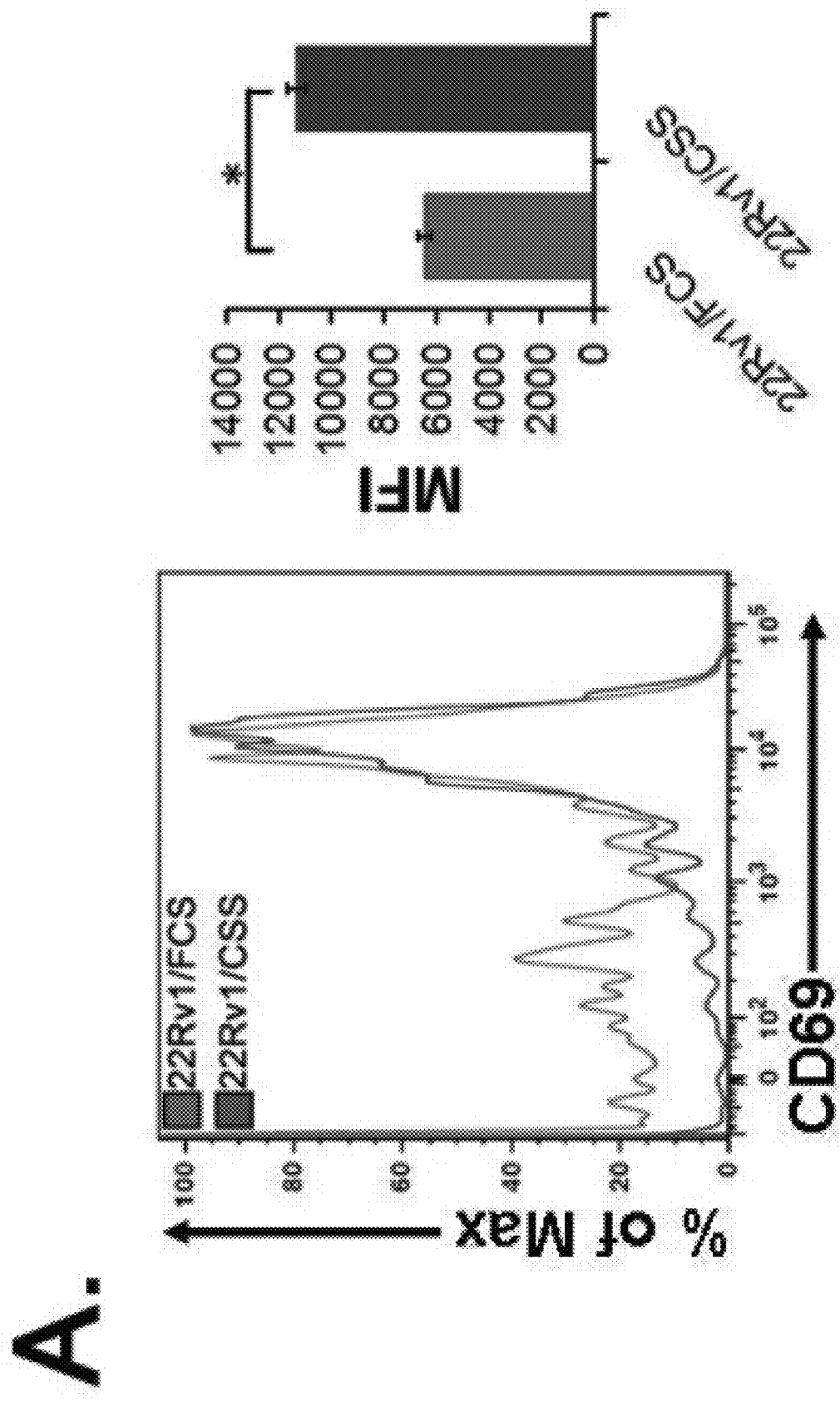
FIG. 5A shows CD69 expression of splenocytes cultured with 22Rv1/CSS (blue) or 22Rv1/FCS (red) cells (quantified in adjacent bar graph—* indicates $p<0.05$ by Student's t-test).
Figure 5B:
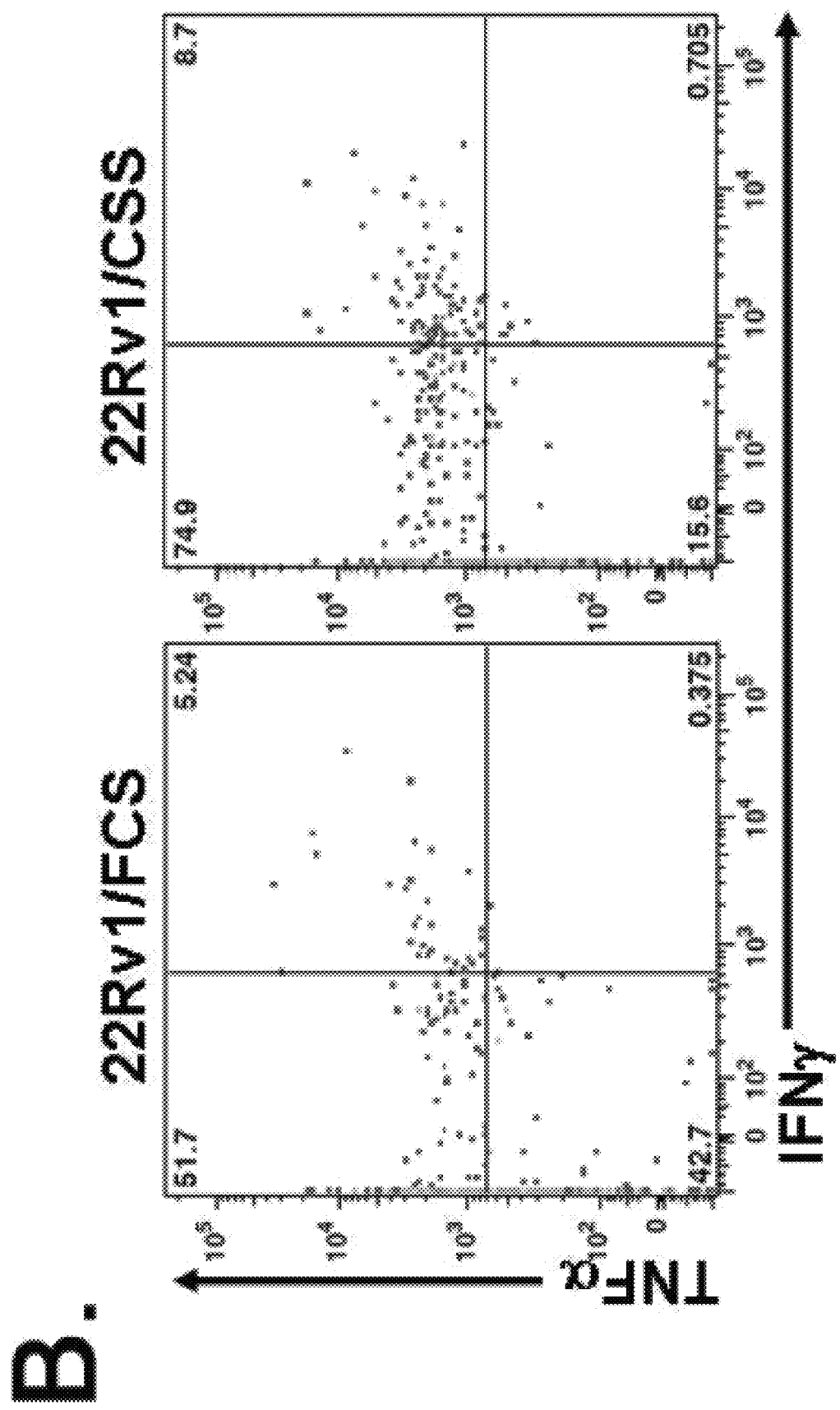
FIG. 5B shows intracellular cytokine staining (IFNγ by TNFα) of T-cells cultured with 22Rv1/CSS (right panel) or 22Rv1/FCS (left panel) cells.
Figure 5C:
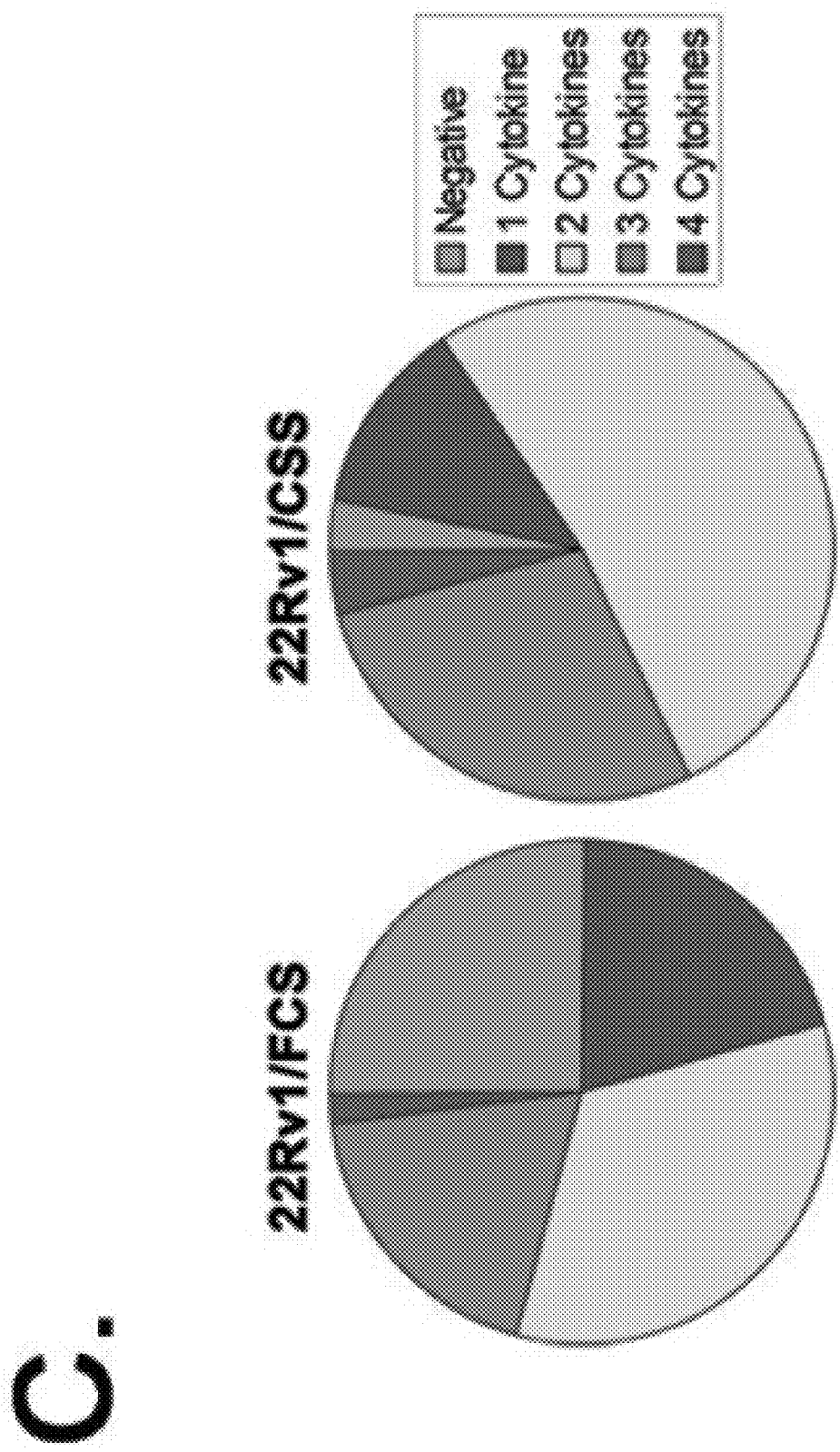
FIG. 5C shows frequency of CD8+ T cells that express zero (blue), one (green), two (yellow), three (orange), or four (red) Th1 related molecules (IFNγ, TNFα, IL-2, and/or granzyme B).
Figure 5D:
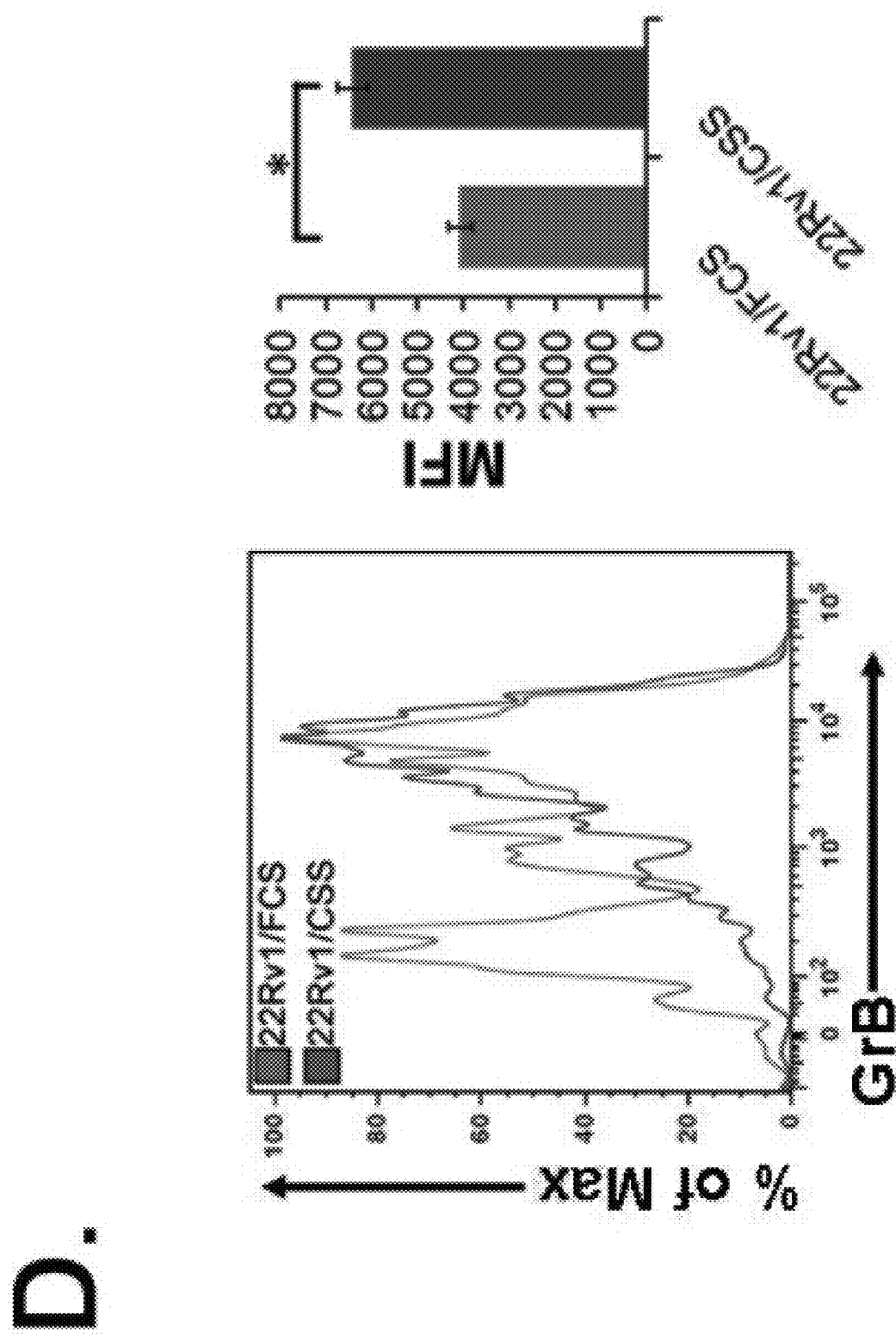
FIG. 5D shows granzyme B expression by CD8+ T cells following culturing with 22Rv1/FCS (red) or 22Rv1/CSS (blue) cells (quantified in adjacent bar graph—* indicates $p<0.05$ by Student's t-test).
Figures 5E, 5F:
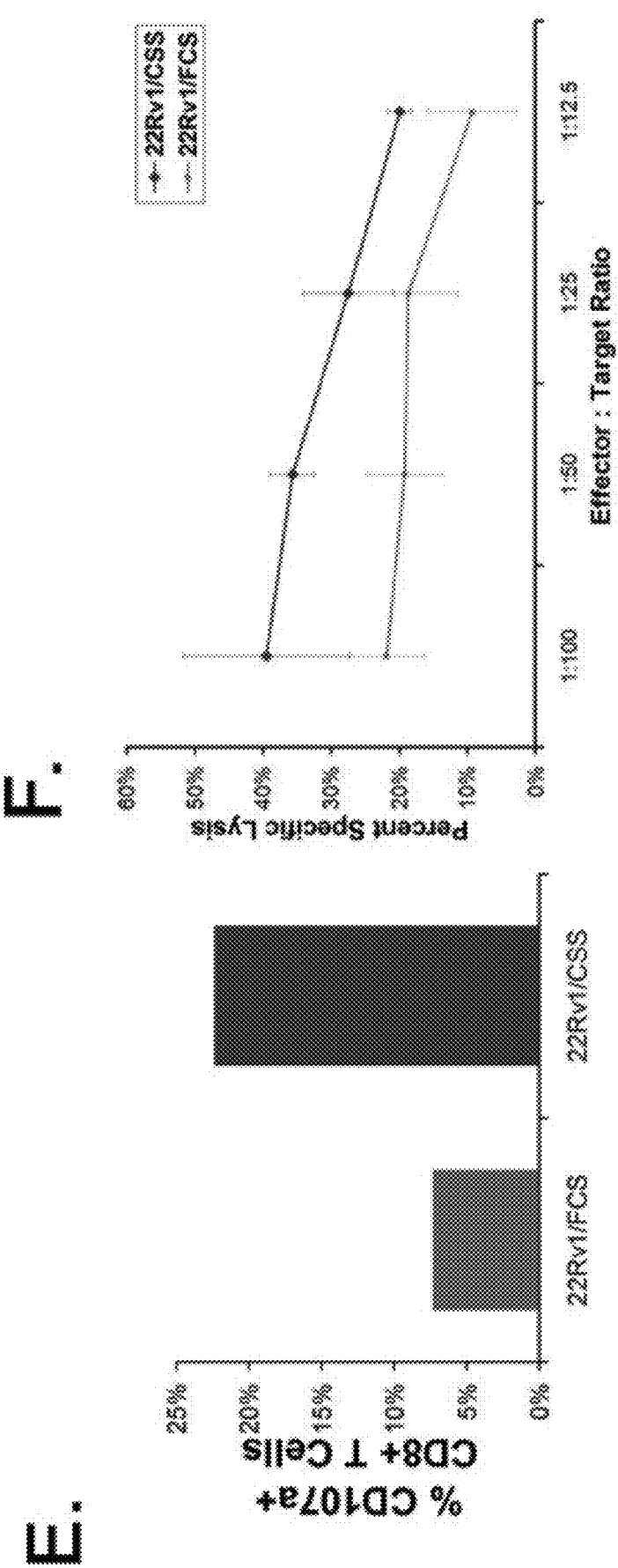

Human AR805 peptide-specific T-cells are shown to have increased levels of T-cell activation, Th1 polyfunctional cytokine expression, and cytotoxicity when exposed to androgen-deprived 22Rv1 prostate cancer cells. AR805 peptide-specific T-cells (previously cultured from the peripheral blood of HLA-A2+ prostate cancer patients (Smith et al., Canc. Res. (2011), 71: 6785-6795) were evaluated for immune responses against HLA-A2-expressing 22Rv1/FCS or 22Rv1/CSS cells. FIG. 5A shows CD69 expression of splenocytes cultured with 22Rv1/CSS (blue) or 22Rv1/FCS (red) cells (quantified in adjacent bar graph—* indicates p<0.05 by Student's t-test). FIG. 5B shows intracellular cytokine staining (IFNγ by TNFα) of T-cells cultured with 22Rv1/CSS (right panel) or 22Rv1/FCS (left panel) cells. FIG. 5C shows frequency of CD8+ T cells that were found to express zero (blue), one (green), two (yellow), three (orange), or four (red) Th1 related molecules (IFNγ, TNFα, IL-2, and/or granzyme B). FIG. 5D shows granzyme B expression by CD8+ T cells following culturing with 22Rv1/FCS (red) or 22Rv1/CSS (blue) cells (quantified in adjacent bar graph—* indicates p<0.05 by Student's t-test). FIG. 5E shows frequency of CD8+ T cells expressing the surface degranulation marker CD107a. FIG. 5F shows cytotoxicity of T-cells cultured with 22Rv1/CSS (blue) or 22Rv1/FCS (red) cells.

Thus, androgen deprivation increases androgen receptor expression and causes prostate tumor cells to have increased susceptibility to AR-specific T-cells.

Example 2

Figures 6A, 6B:
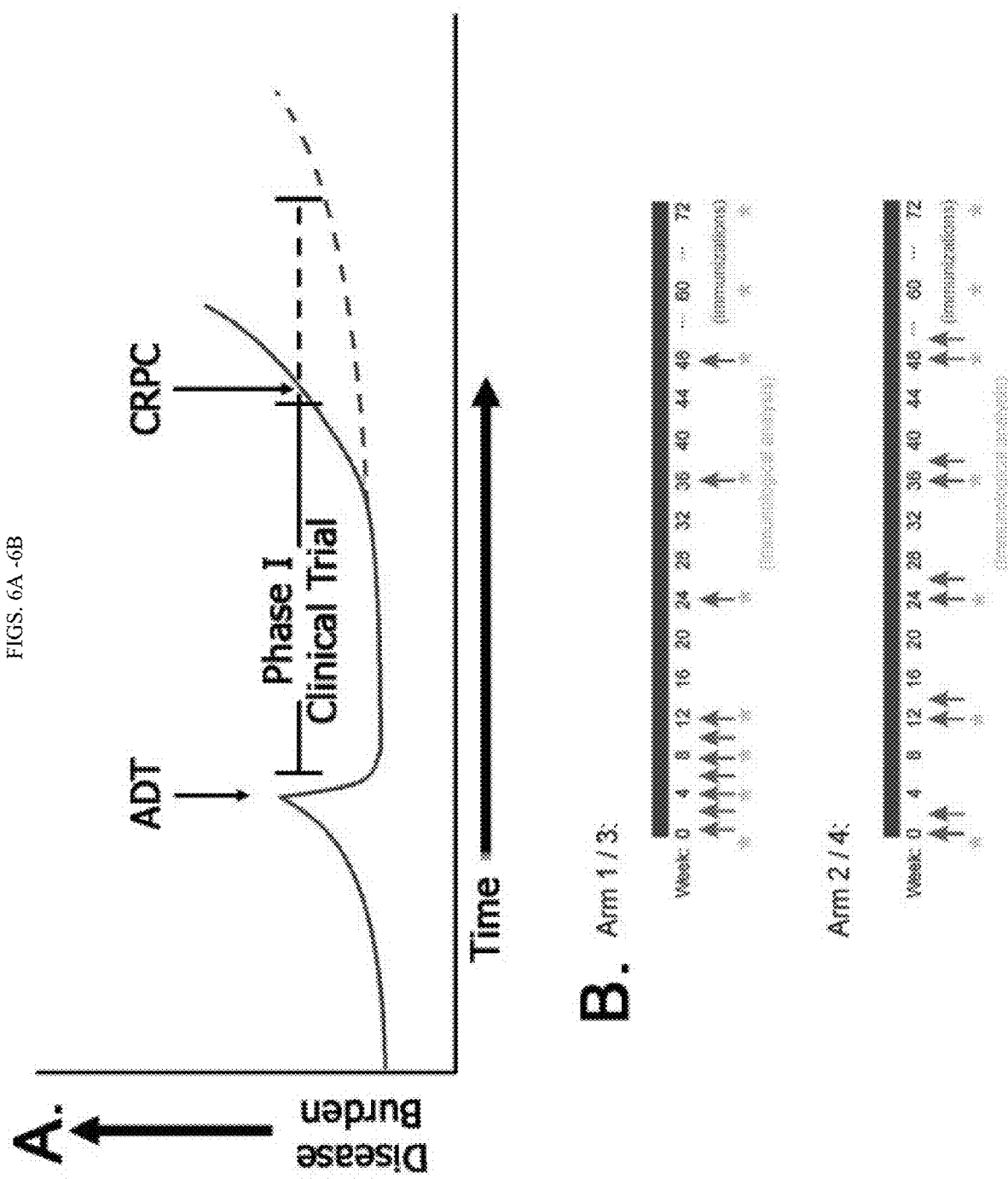
FIG. 6A depicts a schematic of the timing of a clinical trial.
FIG. 6B depicts the proposed dosage regimen of the vaccine in a clinical trial.

Phase I Clinical Trial Evaluating a DNA Vaccine Encoding the AR-LBD in Combination with Androgen Deprivation Therapy FIG. 6A depicts a clinical trial. Men with metastatic prostate cancer who have recently (within 1-6 months) initiated androgen deprivation therapy (ADT) are enrolled in a clinical trial evaluating the safety and immunogenicity of a DNA vaccine encoding the AR LBD (pTVG-AR). This trial seeks to capitalize on targeting one of the most common mechanisms of resistance to ADT (overexpression of the AR) by combining ADT with pTVG-AR, ideally resulting in delayed time to progression (dashed blue line) to castrate-resistant disease (CRPC). FIG. 6B depicts the different ARMS of the study. Patients receive either six biweekly immunizations followed by quarterly boosters, or two biweekly immunizations every ten weeks, either alone or in combination with GM-CSF. Immunizations are continued 18 months or to disease progression. Primary endpoints are safety and ARLBD-specific immunity. Secondary objectives of this trial include evaluating which schedule of immunization is best able to elicit long-lived ARLBD-specific T-cell responses, the effect of GM-CSF in generating immune responses, and to determine the median time to PSA progression and 18-month PSA progression-free survival.

Example 3

Figures 7A, 7B:
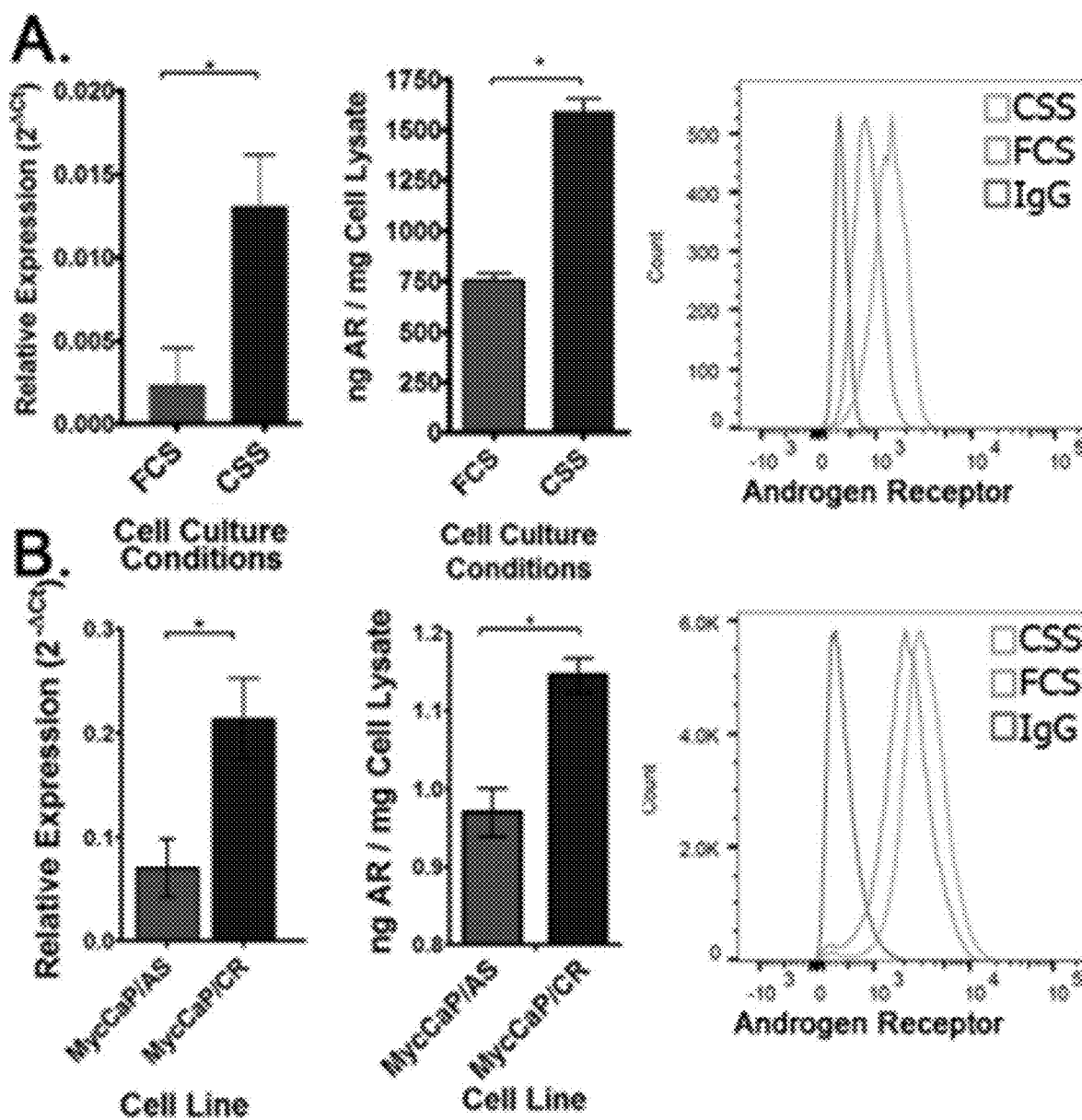
FIGS. 7A and 7B depict androgen-deprived 22Rv1 human prostate cancer cells and castrate-resistant MycCaP mouse prostate cancer cells have increased AR expression after ADT treatment.
Figure 7C:
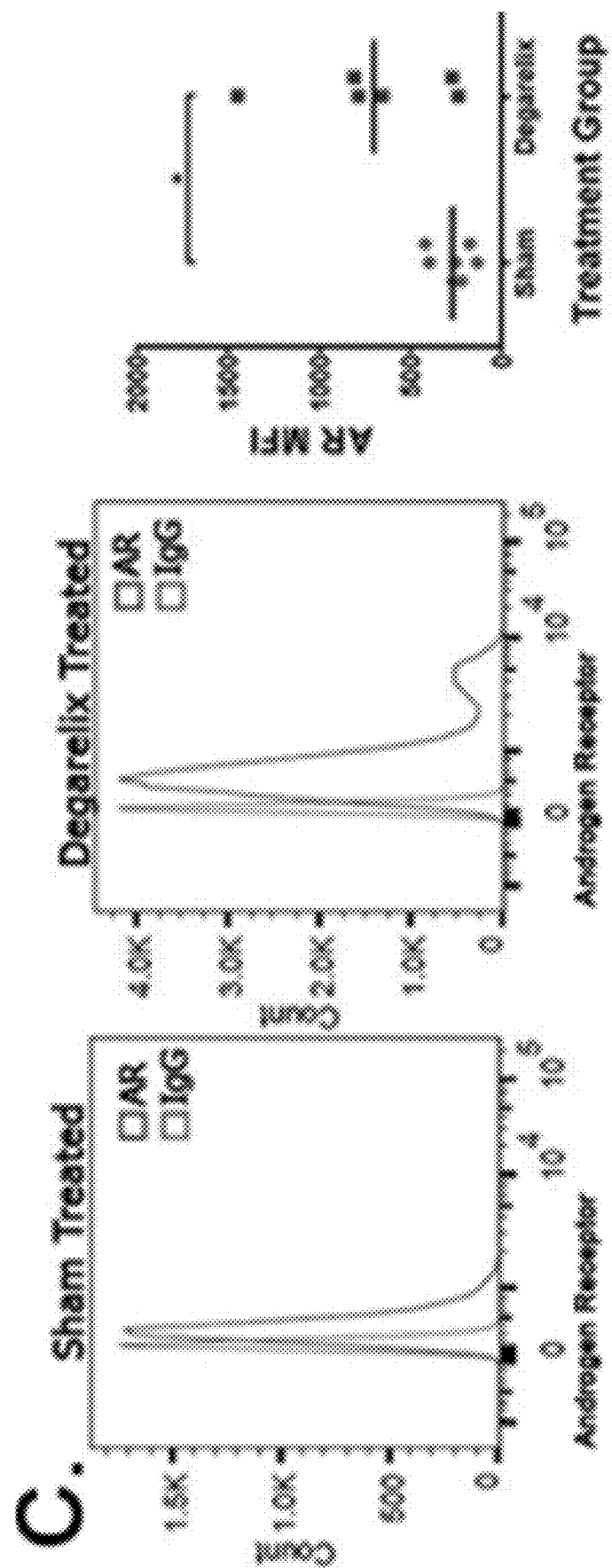
FIG. 7C depicts increased AR expression in tumors in the MycCaP prostate cancer model in vivo after chemical castration using the GnRH antagonist degarelix.
Figure 7D:
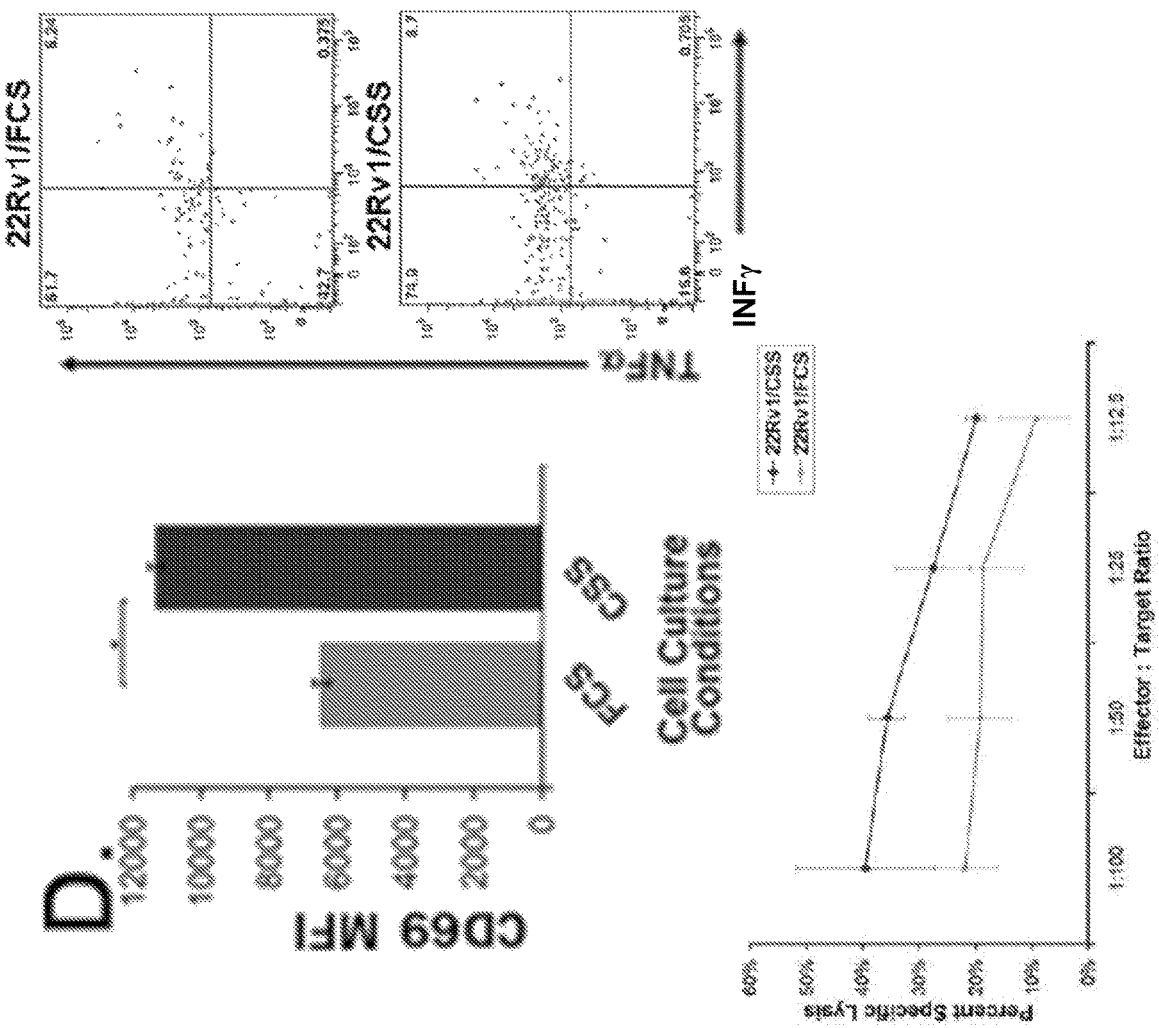
FIG. 7D depicts T-cell activation by CD69 expression (left panel), IFNγ and TNFα cytokine expression (center panel), and cytotoxicity (right panel) that results from AR-specific CD8+ T-cell activation. In all panels, * indicates $p<0.05$ by Student's t-test.

AR Overexpression Occurs in Human and Mouse Prostate Tissue Following AD Therapies and Enhances their Recognition by AR-Specific T-Cells Androgen-deprived 22Rv1 human prostate cancer cells and castrate-resistant MycCaP mouse prostate cancer cells have increased AR expression (FIGS. 7A and 7B) after ADT treatment. We also showed this occurs in the MycCaP prostate cancer model in vivo, as chemical castration using the GnRH antagonist degarelix resulted in increased AR expression in tumors (FIG. 7C). This increased AR expression also caused these tumor cells to be better recognized by AR-specific CD8+ T-cells, as T-cells have higher levels of activation, cytokine expression, and cytotoxicity when cultured with androgen-deprived tumor cells (FIG. 7D).

Briefly, Human 22Rv1 prostate cancer cells cultured in androgen replete (FCS) or—deprived (CSS) conditions (FIG. 7A), or mouse MycCaP cells serially passaged in untreated (MycCaP/AS) or castrate (MycCaP/CR) mice (FIG. 7B) were collected and analyzed for AR expression by qPCR (left panels), ELISA (center panels), and intracellular staining (ICS, right panels). FIG. 7C, FVB mice were challenged with MycCaP/AS tumor cells, and given degarelix or a sham treatment. At the time of outgrowth, tumors were collected and analyzed for AR expression by intracellular flow cytometry (example histogram with samples stained with IgG or AR-intracellular antibodies; quantified in right panels). FIG. 7D, AR-specific CD8+ T cells were cultured with 22Rv1/FCS or 22Rv1/CSS cells, and evaluated for T-cell activation by CD69 expression (left panel), IFNγ and TNFα cytokine expression (center panel), and cytotoxicity (right panel). In all panels, * indicates p<0.05 by Student's t-test.

Example 4

Figures 8A, 8B, 8C:
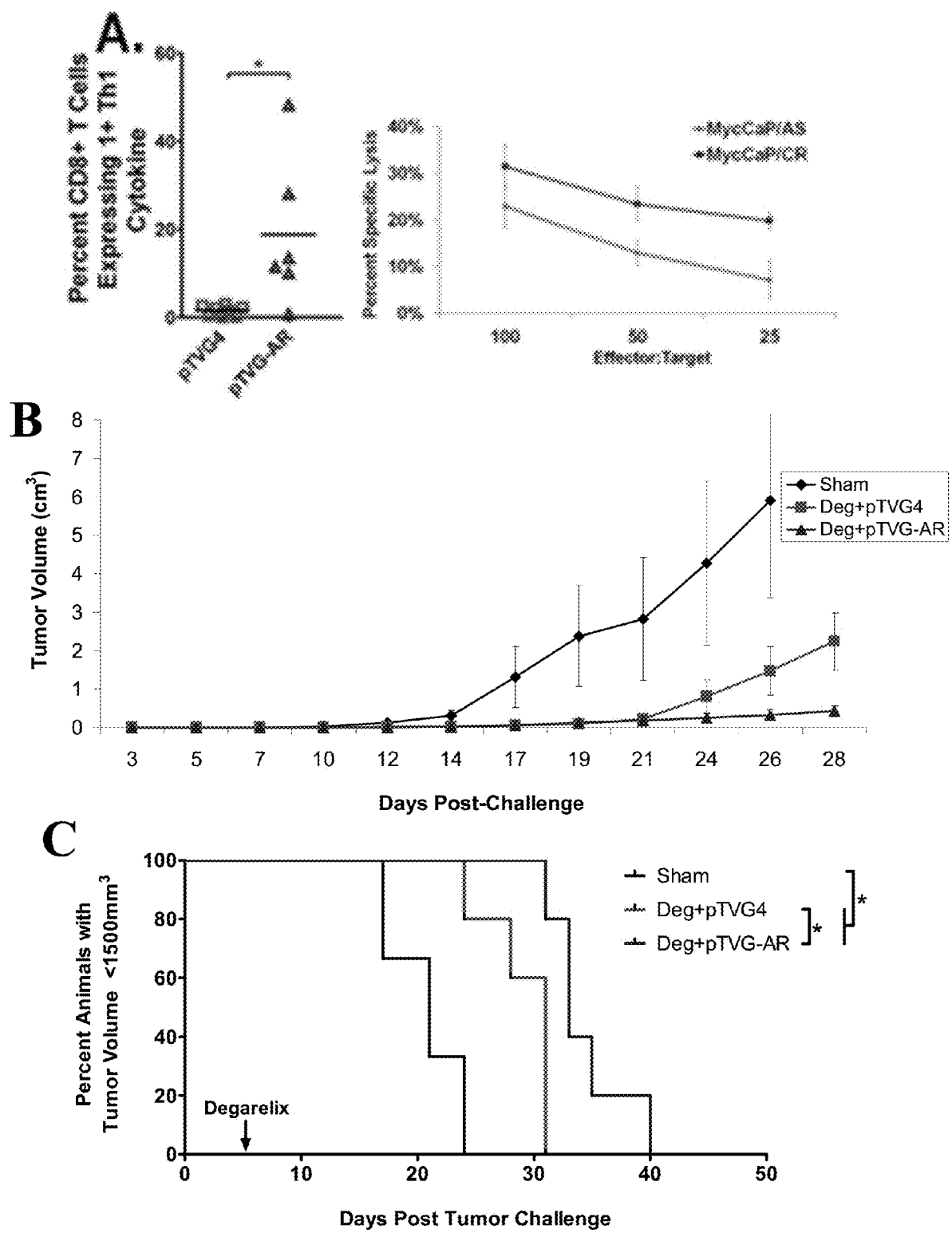
FIG. 8A depicts splenocytes collected and analyzed for immune responses against MycCaP/CR tumor cells by intracellular cytokine staining (left panel) and AR peptide-stimulated splenocytes from pTVG-AR-immunized mice were measured for ability to lyse MycCap/AS vs. MycCap/CR tumor cells (right panel).
FIG. 8B depicts mice followed for tumor volume. In all panels, * indicates $p<0.05$ by Student's t-test.
FIG. 8C depicts tumor volume post-challenge of control (sham), degarelix+pTVG4 and degarelix+pTVG-AR.

AD with AR-Directed Immunization Increases Anti-Tumor Immune Responses and Delays Tumor Recurrence This Experiment demonstrates that the combination of AD with AR-directed immunization increases anti-tumor immune response. MycCaP tumor-bearing FVB mice treated with degarelix (ADT treatment) followed by immunization at weekly intervals with the pTVG-AR DNA vaccine had enhanced immune responses against androgen-deprived tumor cells and a delay in prostate cancer regrowth compared to controls (FIG. 8). Briefly, male FVB mice (n=8) were implanted with MycCaP tumors, treated with degarelix (or sham), and immunized weekly with pTVG-AR or control pTVG4. FIG. 8A, splenocytes were collected and analyzed for immune responses against MycCaP/CR tumor cells by intracellular cytokine staining (left panel) and AR peptide-stimulated splenocytes from pTVG-AR-immunized mice were measured for ability to lyse MycCap/AS vs. MycCap/CR tumor cells (right panel). FIG. 8B depicts mice followed for tumor volume. In all panels, * indicates p<0.05 by Student's t-test. FIG. 8C depicts tumor volume post-challenge of control (sham), degarelix+pTVG4 and degarelix+pTVG-AR.

Example 5

Increased Androgen Receptor Expression in Prostate Cancer Cells Following Androgen Deprivation Increases Recognition by Androgen Receptor-Specific T Cells This example again demonstrates that androgen deprivation increases AR expression in human and murine prostate tumor cells in vivo and in vitro that persisted over time. Increased AR expression was associated with increased recognition and cytolytic activity by AR-specific T cells. Further, ADT combined with vaccination, using a DNA vaccine encoding the ligand-binding domain of the AR, led to improved anti-tumor responses as measured by tumor volumes and delays in the emergence of castrate-resistant prostate tumors in two murine prostate cancer models (Myc-CaP and prostate-specific PTEN-deficient mice). This data supports the benefits of combining ADT with AR-directed immunotherapy over ADT combined with other immunotherapeutic approaches by specifically targeting a major mechanism of resistance, overexpression of AR.

Materials and Methods of Example 5

Mice and Cell Lines

Human prostate cancer cells were obtained from ATCC, and cultured in RPMI-1640 medium with 200 U/mL penicillin/streptomycin, 1 mM sodium pyruvate, and 0.1 mM β-mercaptoethanol. Cell identity and *mycoplasma* testing was confirmed by DDC Medical (Fairfield, Ohio). Myc-CaP/AS or Myc-CaP/CR cells (androgen-sensitive and castrate-resistant variants of the Myc-CaP parental line originally generated by Charles Sawyers) and culture conditions have been previously described (22). Both human and mouse cell lines were maintained in either 10% complete fetal calf serum (FCS) or charcoal-stripped serum (CSS) for androgen-replete or androgen-deprived conditions.

Tumor studies using Myc-CaP tumor cells were conducted in wild-type male FVB mice (Jackson Laboratory, Bar Harbor, Me.). PTEN knock-out mice were generated by crossing Pten foxed (loxp/loxp) animals with Probasin-Cre (PB-Cre4+) as has been described (23). Mice were screened by PCR for the floxed or wild-type PTEN alleles (forward primer: CAA GCA CTC TGC GAA CTG AG; reverse primer: AAG TTT TTG AAG GCA AGA TGC) and PB-Cre transgene (forward primer: CTG AAG AAT GGG ACA GGC ATT G; reverse primer: CAT CAC TCG TTG CAT CGA CC). Mice were maintained under aseptic conditions and all experiments were conducted under an IACUC-approved protocol.

Tumor Studies

FVB mice were inoculated subcutaneously with 106 Myc-CaP/AS tumor cells, and followed daily for the presence of palpable tumors. Once tumors were palpable, mice were treated subcutaneously with either degarelix (25 mg/kg) or a vehicle sham treatment every four weeks. For immunization studies, degarelix-treated animals were randomized to weekly immunization with 100 μg pTVG4 or pTVG-AR beginning one day after receiving degarelix. Tumor growth was measured at least three times weekly, and tumor volumes calculated as we've published (19). At the time of euthanasia, tumors and spleens were collected. For studies using PTEN-deficient mice, animals began receiving degarelix (25 mg/kg) at 20 weeks (+/−two weeks) of age, followed by biweekly immunization with 100 μg pTVG4 or pTVG-AR beginning one day after ADT. Animals were treated until 40 weeks of age (+/−two weeks) before tissue collection.

Androgen Receptor Enzyme-Linked Immunosorbent Assay (ELISA)

Cultured prostate cancer cells were collected, cell lysates prepared, and analyzed for protein expression using the PathScan androgen receptor ELISA per manufacturer's instructions (Cell Signaling Technology, Danvers, Mass.). Briefly, microwell strips (pre-coated with anti-AR antibody) were coated with 2 mg/mL protein lysates in triplicate, and incubated overnight. AR was detected using a detection antibody followed by HRP-linked secondary antibody and TMB substrate development. A standard curve using purified AR LBD protein (Invitrogen, Carlsbad, Calif.) was generated, and used to determine relative AR concentration per mg cell lysate.

Flow Cytometry

For androgen receptor intracellular staining, cells were stained with a Live/Dead GhostDye 780 Live/Dead Stain (Tonbo Biosciences, San Diego, Calif.) and CD45 (clone 30-F11, Tonbo Biosciences) for dissociated tumor samples, and intracellularly stained with antibodies directed against the androgen receptor ligand-binding domain (clone EP670Y, Abcam, Cambridge, United Kingdom) and amino terminal domain (clone D6F11, Cell Signaling Technologies), or isotype controls. For HLA-A2 and PD-L1 expression, cells were stained with HLA-ABC (clone W6/32, eBioscience, San Diego, Calif.) and PD-L1 (clone MIH-5, eBioscience) antibodies.

Androgen Receptor Quantitative Real-Time PCR

Prostate tumor cells (cell lines or dissociated tumors) were collected, RNA was prepared (RNeasy RNA purification system; Qiagen, Hilden, Germany), used to synthesize cDNA (iScript cDNA synthesis kit; BioRad, Hercules, Calif.), and used as a template for qPCR reactions using SsoFast qPCR supermix (BioRad). Reactions were performed using a Bio-Rad MyiQ thermocycler, using an annealing temperature of 60° C. and 40 cycles. Primer sets:

full-length human androgen receptor

```
forward:
                                      SEQ ID NO 7
ACATCAAGGAACTCGATCGTATCATTGC,;

reverse:
                                      SEQ ID NO: 8
TTGGGCACTTGCACAGAGAT,,
```

AR-V7

```
forward:
                                      SEQ ID NO: 13
CCATCTTGTCGTCTTCGGAAATGTTATGAAGC,;

reverse:
                                      SEQ ID NO: 14
TTTGAATGAGGCAAGTCAGCCTTTCT,,
``` full length mouse AR

```
forward:
                                      SEQ ID NO: 17
GGACCATGTTTTACCCATCG,;

reverse:
                                      SEQ ID NO: 18
ATCTGGTCATCCACATGCAA,,
``` mouse AR-V2 forward:
GGACCATGTTTTACCCATCG,; SEQ ID NO: 17 reverse:
TTGTTGTGGCAGCAGAGTTC,, SEQ ID NO: 19 mouse AR-V4 forward:
GGACCATGTTTTACCCATCG,; SEQ ID NO: 17 reverse:
AAGTGGGGAACCACAGCAT,, SEQ ID NO: 20
and

β-actin forward:
TCATGAAGTGTGACGTTGACATCCGT,; SEQ ID NO: 15 reverse:
CTTAGAAGCATTTGCGGTGCACGATG, SEQ ID NO: 16)
(24-26).

Results were analyzed by the 2-ΔCt method relative to β-actin as a control gene, as published (26).

Immunology Assays

To study immune responses, human T-cell lines or splenocytes were collected as previously described (20), and used for intracellular cytokine staining assays and cytotoxicity assays. For intracellular cytokine staining, cells were stimulated for 18 hours with media alone, an ARLBD peptide pool (a pool of 15-mer peptides, overlapping by 11 residues, and covering the entire sequence of the AR LBD; LifeTein, Somerset, N.J.), tumor cells, or a PMA/Ionomycin positive control. Cells were stained using a fixable live/dead marker (Tonbo Bioscience) and extracellular and intracellular antibodies. Human antibodies: CD3 (clone UCHT1, BD Biosciences), CD4 (clone RPA-T4, BD Biosciences), CD8 (clone RPA-T8, eBioscience), CD69 (clone FN50, BD Biosciences), CD107a (clone H4-A3, BD Biosciences), IL2 (clone MQ1-17H12, eBioscience), IFNγ(clone 4S.B3, BioLegend, San Diego, Calif.), TNFα (clone MAb11, BD Biosciences), GrB (clone GB11, BD Biosciences). Mouse antibodies: CD3 (clone 17A2, BD Biosciences), CD4 (clone GK1.5, BD Biosciences), CD8 (clone 53-6.7, BD Biosciences), CD45 (clone 30-F11, BD Biosciences), CD69 (clone H1.2F3, eBioscience), IFNγ(clone XMG1.2, BD Biosciences), TNFα (clone MP6-XT22, BD Biosciences). Cells were subsequently analyzed using an LSR II or Fortessa flow cytometer (BD Biosciences), and events were analyzed by gating CD3+CD4+ or CD3+CD8+ cells and analyzing this population for expression of CD69, CD107a, IFNγ, TNFα, IL2, and/or GrB. Cytotoxicity assays were performed as has been previously described (20). Briefly, splenocytes were restimulated for five days with an ARLBD peptide pool, and were cultured with tumor cell lines, after which LDH release was calculated using the Cytotox 96 Assay kit (Promega, Madison, Wis.), as previously published (19).

Immunohistochemistry

Paraffin-embedded MycCaP tumors were stained for CD3 expression by immunohistochemistry as has been described (20). Sections were stained with primary antibodies (CD3: clone SP7, Abcam), developed using the LSAB+ System-HRP (Agilent Technologies, Santa Clara, Calif.) and Metal Enhanced DAB Substrate Kit DAB metal concentration (Thermo Fisher Scientific, Waltham, Mass.), imaged using an Olympus BX51 fluorescent microscope (Olympus, Lombard, Ill.) in combination with SPOT RT analysis software (SPOT Imaging Solutions, Sterling Heights, Mich.), and quantified by the frequency of CD3+ cells per 10× field, counting at least five fields per tumor section per animal by a blinded investigator.

Positron Emission Tomography/Computed Tomography Imaging

All mice were intravenously administered between 5-8 MBq of 124I-CLR1404 and then micro positron emission tomography/computed tomography (PET/CT) scanned 96 hrs post-injection. During scanning, mice were anesthetized with 2% isoflurane inhalation gas mixed with 1 L/min of pure oxygen (27). Mice were scanned with the Siemens Inveon Hybrid microPET/CT (Siemens Medical Solutions, Knoxville, Tenn.) in the prone position. Forty-million counts per mouse were collected for the PET scan to obtain adequate signal-to-noise. PET data were histogrammed into one static frame and subsequently reconstructed using ordered-subset expectation maximization (OSEM) of three dimensions followed by the maximum a posteriori algorithm, and CT attenuation and scatter correction were applied based on the NEMA NU 4 image-quality parameters (28).

All PET and CT images were co-registered. Image data were analyzed using the General Analysis tools provided by Siemens Inveon Research Workplace (Siemens Medical Solutions). Data were identically window/leveled and scaled according to each animal's decay corrected injection activity. Based on the PET and CT images, a reference volume of interest (VOI) was drawn around each tumor and a separate background tissue VOI was drawn on muscle and liver. VOI thresholding within the reference tumor VOI was adjusted to include all signal greater than sixty percent of the maximum signal. Data were reported as percent injected dose normalized by the mass of the tissue VOI (% ID/g tissue), with the assumption that all tissue density is akin to water (1 g/mL). Data were then averaged within pre- and post-treatment groups and normalized to background tissue values.

Results

Figure 11A:
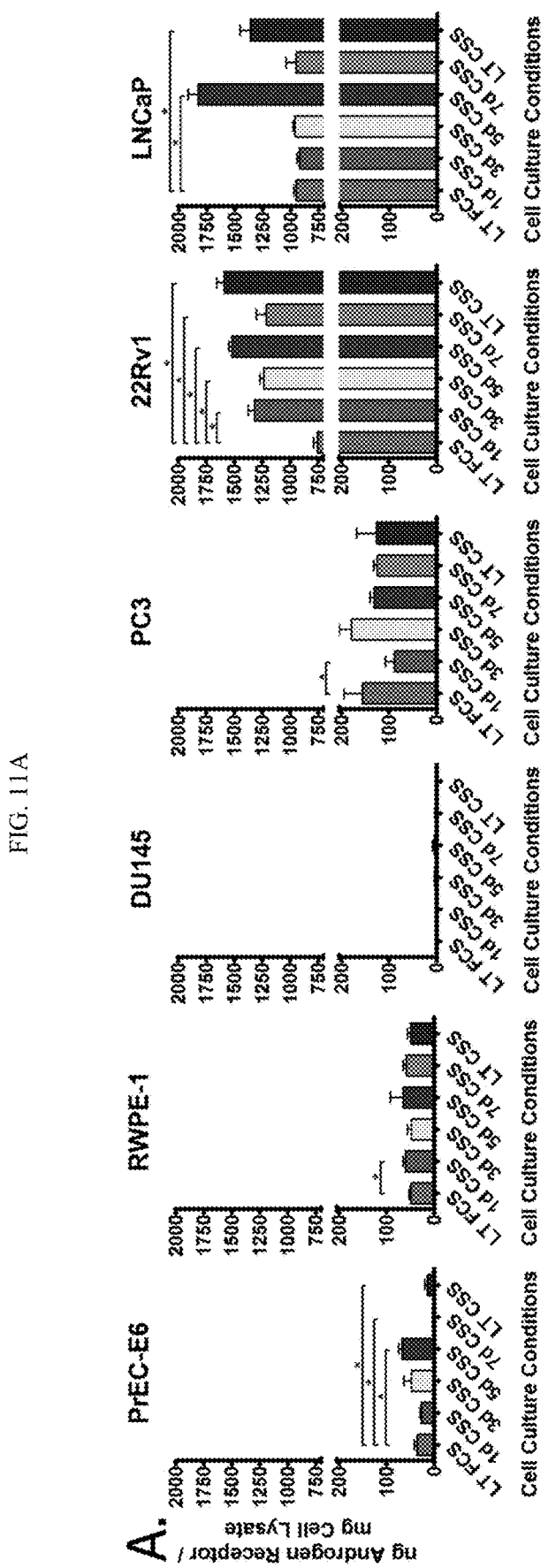
FIG. 11A shows prostate cell lines (immortalized human epithelial lines: RWPE-1 and PrEC-E6; androgen-independent prostate cancer cell lines: DU-145 and PC-3; and androgen-dependent prostate cancer cell lines: LNCaP and 22Rv1) cultured in either androgen-replete (FCS) or androgen-deprived (CSS) medium for one to seven days (1d-7d) or for greater than six months (long-term: LT) analyzed for androgen receptor protein expression by quantitative ELISA (panel A).
Figure 11B:
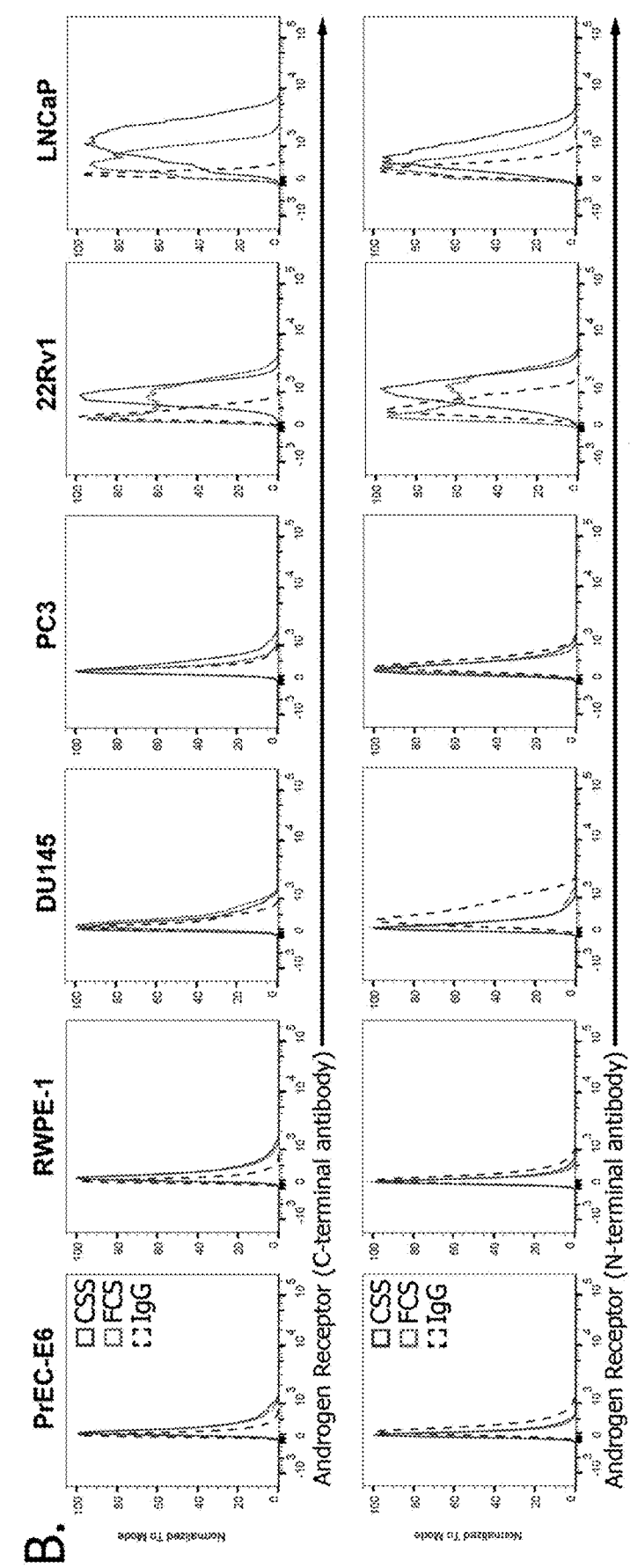
FIG. 11B shows prostate cell lines cultured long-term FCS (light grey) or CSS (dark grey). Cultured cell lines were analyzed for AR expression by intracellular staining using antibodies specific for the ligand-binding domain (top panels) or amino-terminal domain (lower panels).
Figures 11C, 11D, 11E:
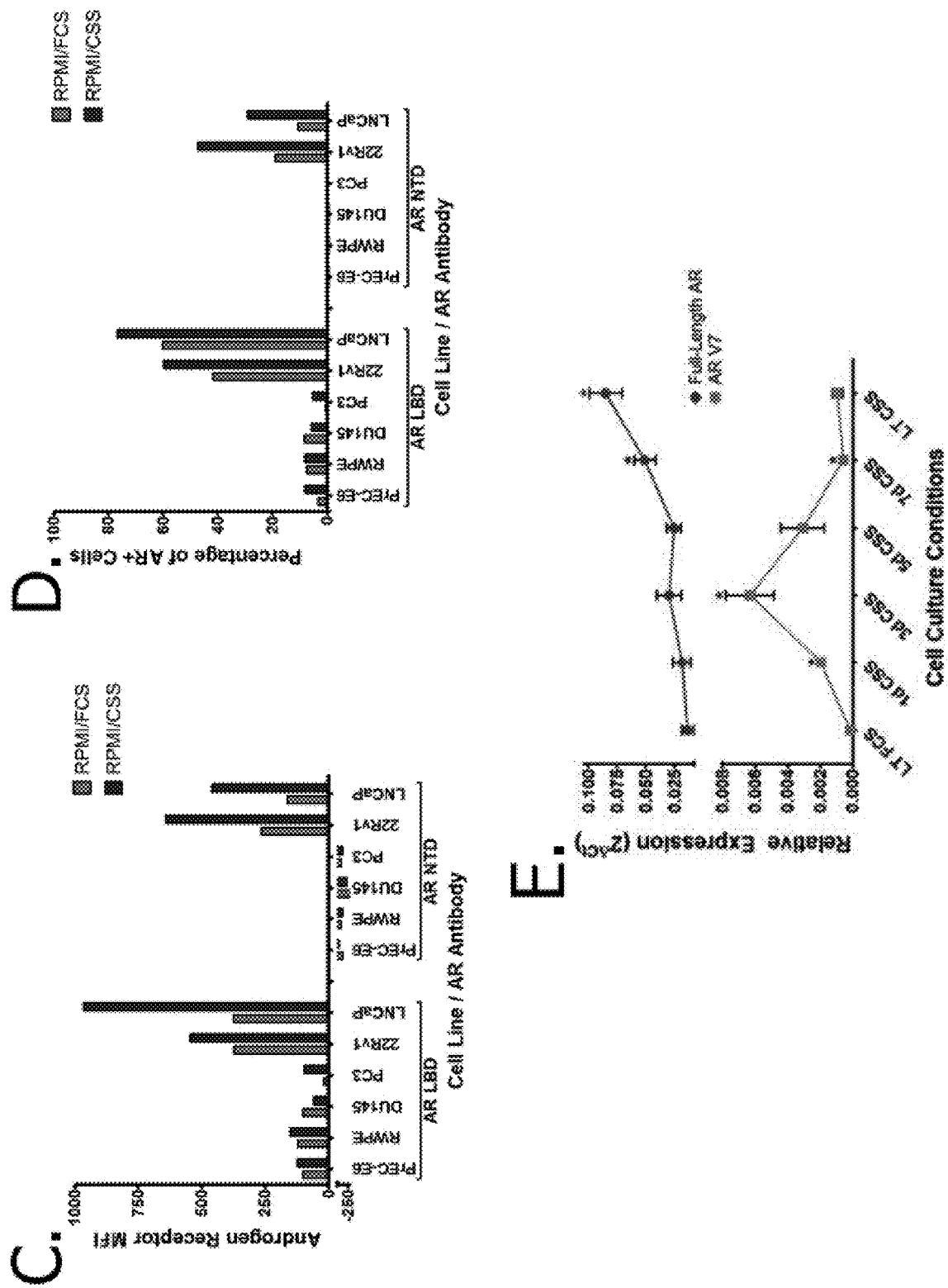
FIG. 11C shows quantified amplitude of AR expression in cultured prostate cell lines.
FIG. 11D shows frequency of AR+ cells in cultured prostate cell lines.
FIG. 11E shows RNA quantified from 22RV1/CSS cells cultured for different periods of time analyzed for the presence of full-length (dark grey) or AR-V7 (light grey) AR transcripts. In all panels, * indicates p<0.05 by student's t-test and data is representative of at least two independent experiments.

Androgen Deprivation Increases Androgen Receptor Expression and Enhances AR-Specific T Cell Responses to Androgen-Deprived Prostate Tumor Cell Lines In this Example, a panel of six prostate cell lines (two immortalized prostate epithelial lines, two androgen-independent prostate cancer lines, and two androgen-dependent prostate cancer lines) were cultured for short (one to seven days) or extended periods (greater than six months) in androgen-deprived medium and analyzed for AR expression. Androgen deprivation was found to result in an increase in AR protein expression in androgen-dependent prostate tumor cells by quantitative ELISA (FIG. 11A), as well as by intracellular staining using antibodies directed against both the ligand-binding domain as well as the amino-terminal domain (FIG. 11B, with the amplitude and frequency of AR expression quantified in FIGS. 11C and 11D, respectively). Analysis of 22Rv1 cells (which are known to express AR-V7, an LBD-loss splice variant) showed that androgen deprivation led to a steadily increasing expression in full-length AR as well as a transient increase in AR-V7 (FIG. 11E), with no detectable expression of AR-V1, AR567es, or other splice variants). However, AR-V7 expression was at significantly lower levels compared to full-length AR transcripts.

Figures 11F, 11G, 11H, 11I:
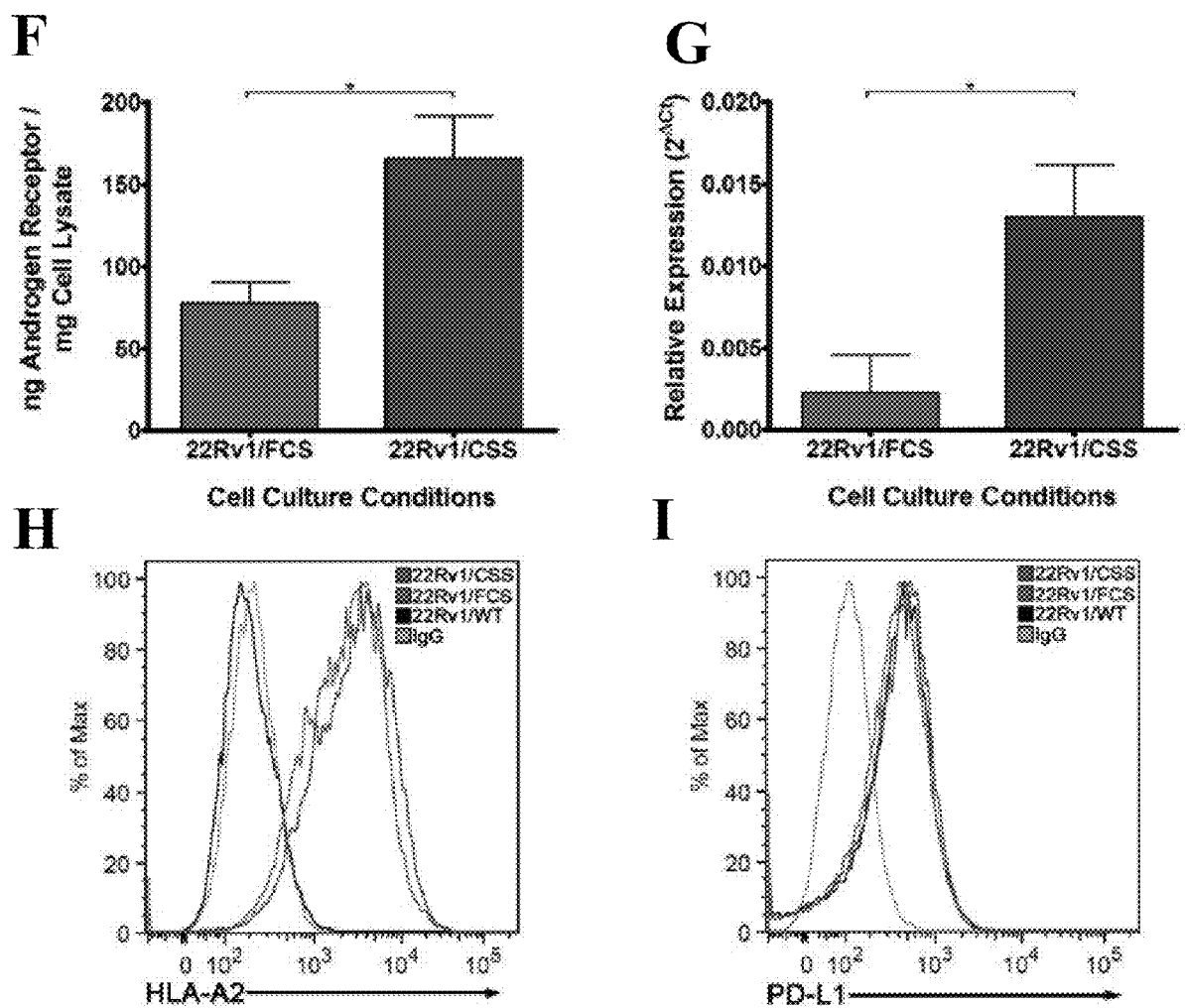
FIG. 11F shows phenotypic validation of HLA-A2-transfected 22Rv1/FCS and 22Rv1/CSS cells. 22Rv1 cells cultured for greater than six months in androgen replete (22Rv1/FCS) or androgen deprived (22Rv1/CSS) medium were transfected with a lentiviral vector encoding HLA-A2. HLA-A2-expressing cells were then sorted by fluorescence-activated cell sorting, and expanded lines were evaluated for AR protein by quantitative ELISA. In all panels, * indicates p<0.05 by Student's t-test.
FIG. 11G shows expanded lines of FIG. 11F evaluated for AR protein by qRT-PCR.
FIG. 11H shows cells of FIG. 11G analyzed for the expression of HLA-A2.
FIG. 11I shows cells of FIG. 11G analyzed for the checkpoint ligand PD-L1 by flow cytometry.
Figures 12A, 12B, 12C, 12D, 12E, 12F:
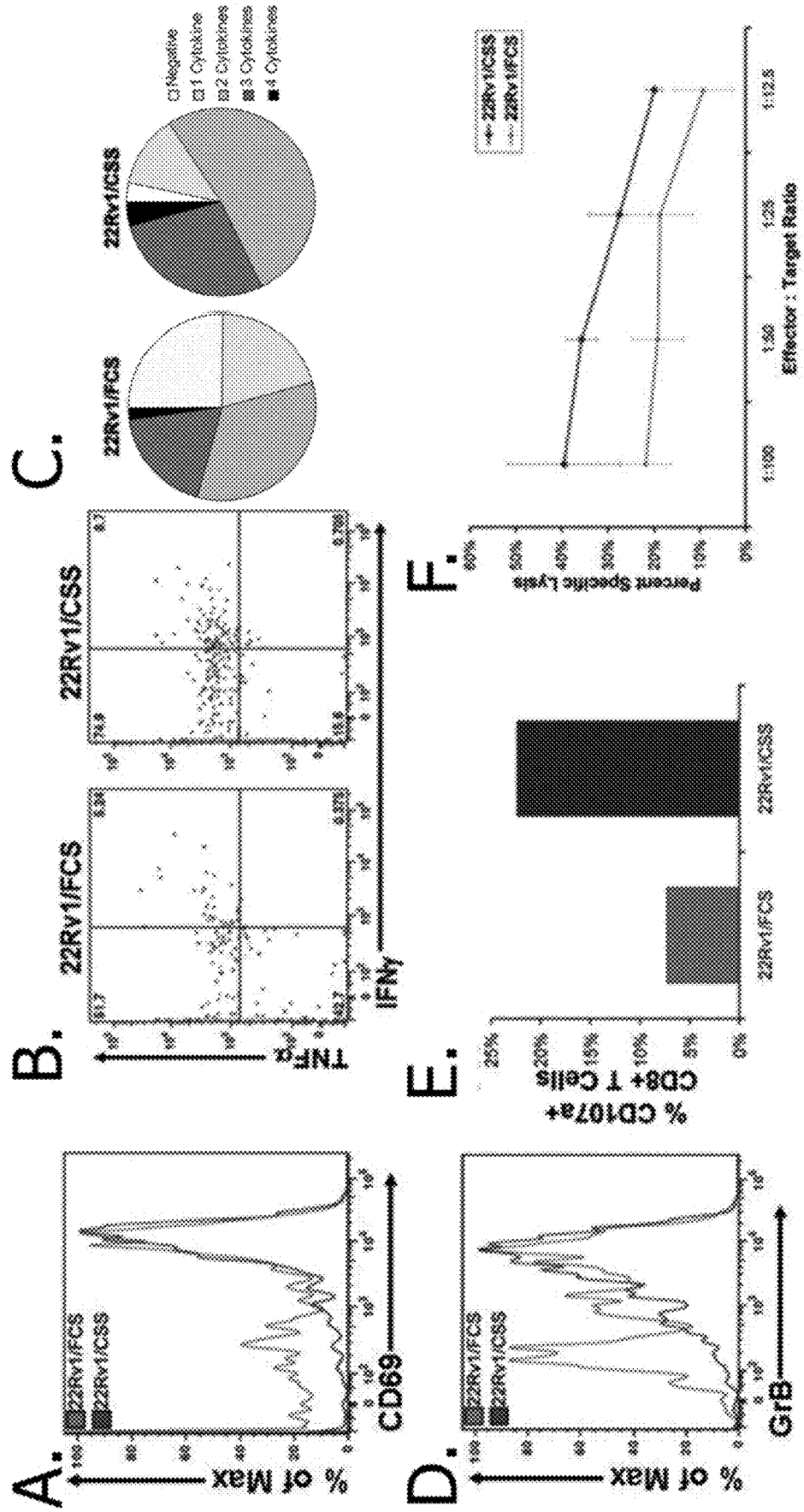
FIG. 12A shows AR-specific T cells have increased recognition and lysis of androgen-deprived tumor cells. AR805-specific human T-cell cultures incubated with HLA-A2-expressing 22Rv1/FCS or 22Rv1/CSS cells were measured for surface expression of CD69.
FIG. 12B show AR805-specific human T-cell cultures incubated with HLA-A2-expressing 22Rv1/FCS or 22Rv1/CSS cells and measured for intracellular cytokine expression of IFNγ and/or TNFα.
FIG. 12C demonstrates polyfunctional cytokine expression quantified in AR805-specific human T-cell cultures incubated with HLA-A2-expression 22Rvi/FCS or 22Rv1/CSS cells.
FIG. 12D shows cytolytic and degranulation activity of AR-specific T cells measured by intracellular granzyme B expression.
FIG. 12E shows cytolytic and degranulation activity of AR-specific T cells measured by surface CD107a expression.
FIG. 12F shows tumor cell cytotoxicity of AR-specific T cells.

To determine whether this increase in AR expression following androgen deprivation resulted in enhanced AR-specific T-cell effector function against these tumor cells, 22Rv1 cells were first transfected to express HLA-A2 as a model MHC molecule, and one for which AR-restricted epitopes have been previously identified (19). After generating this cell line, increased AR protein and RNA expression following androgen-deprivation observed in the parental cell lines was confirmed in these HLA-A2-expressing lines (FIG. 11F-G). These 22Rv1/FCS and 22Rv1/CSS cells were then incubated with T cell lines specific for the HLA-A2-restricted AR805 epitope. T cells cultured with the 22Rv1/CSS cell line were shown to have higher levels of T-cell activation (as measured by CD69 expression—FIG. 12A), as well as increased expression of Th1 cytokines (FIG. 12B), including CD8+ T cells with polyfunctional cytokine expression (FIG. 12C), compared to T cells that had been stimulated with 22Rv1 cells cultured under androgen-replete conditions. Co-culture with 22Rv1/CSS cells also resulted in higher expression of granzyme B (FIG. 12D), the degranulation marker CD107a (FIG. 12E), as well as increased cytotoxicity (FIG. 12F) compared to co-culture with 22Rv1/FCS cells. Similar studies, using splenocytes from HLA-A2 transgenic mice that were directly immunized with another HLA-A2 restricted epitope, AR811, replicated these results in terms of increased cytokine expression, T-cell activation, and cytotoxicity when cultured with androgen-deprived HLA-A2-expressing 22Rv1 cells (FIG. 12G). These differences in T-cell recognition and cytotoxicity were likely not due to altered MHC class I nor PD-L1 expression, as 22Rv1/CSS and 22Rv1/FCS cells expressed identical levels of both HLA-A2 and PD-L1 (FIG. 11H-I).

Figures 13A, 13B:
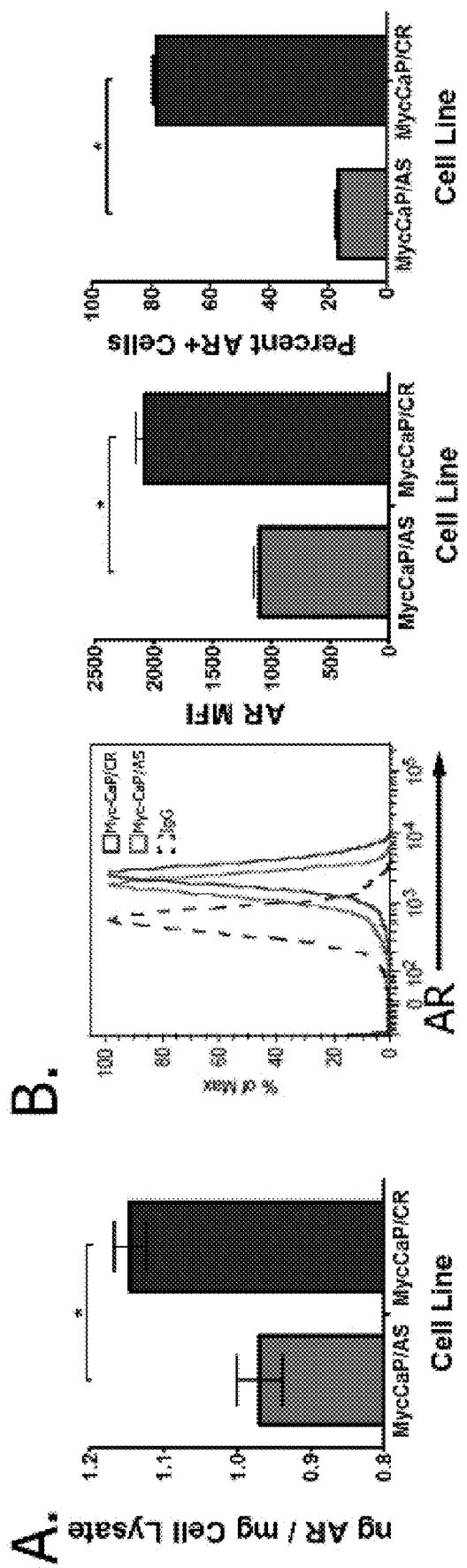
FIG. 13A demonstrates that androgen deprivation increases AR expression in Myc-CaP tumor cells in vitro and in vivo. Androgen-sensitive (Myc-CaP/AS) and castrate-resistant (Myc-CaP/CR) cells were analyzed for AR protein expression by quantitative ELISA.
FIG. 13B shows androgen-sensitive (Myc-CaP/AS) and castrate-resistant (Myc-CaP/CR) cells analyzed for AR protein expression by intracellular staining (quantified for amplitude and frequency of expression in side panels).
Figures 13C, 13D:
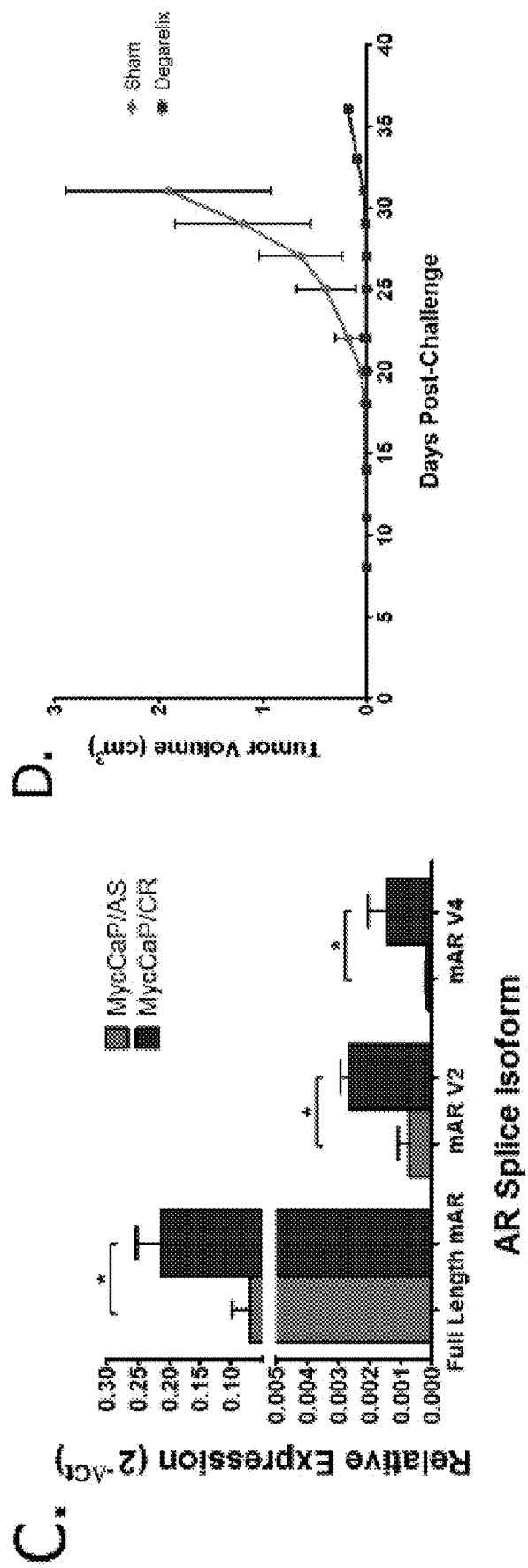
FIG. 13C shows RNA samples from Myc-CaP/AS and Myc-CaP/CR cells analyzed by quantitative PCR for expression of full-length or splice variants mAR V2 or mAR V4.
FIG. 13D shows Myc-CaP/AS tumor-bearing FVB mice with palpable tumors were treated with degarelix (n=4) or sham-treatment (n=3) and followed for tumor growth. Results are representative of two independent studies.
Figure 13E:
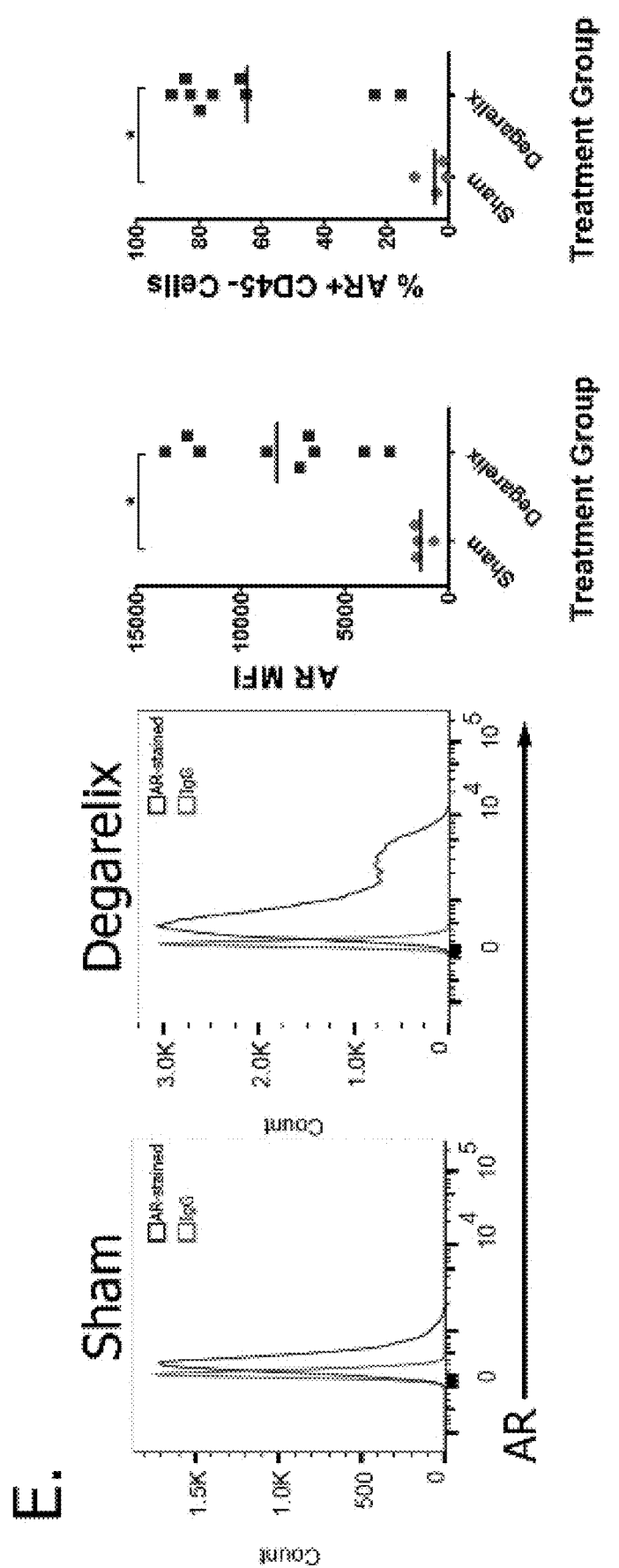
FIG. 13E shows recurrent tumors collected and analyzed for AR expression by intracellular staining using an antibody directed against the ligand-binding domain (amplitude and frequency quantified in side panels). In all panels, * indicates p<0.05 by student's t-test.

Androgen Deprivation Increases AR Expression in Myc-CaP Tumor Cells In Vitro and in Vivo We have previously used the TRAMP mouse model to study the impact of vaccines targeting AR on tumor development and progression (20). However, it has previously been reported that androgen deprivation of TRAMP mice, and many other murine prostate tumor models, results in AR loss and the development of neuroendocrine tumors (29). Consequently, we sought to evaluate other models more representative of human prostate cancer that continue to express AR following androgen deprivation. One such model is the Myc-CaP cell line, which mimics the human disease in that it maintains AR expression following castration (22). To confirm this, androgen-sensitive Myc-CaP cells (Myc-CaP/AS, generated from untreated FVB mice), and castration-resistant Myc-CaP cells (Myc-CaP/CR, generated from serial passaging of the Myc-CaP/AS cell line through castrated mice) were studied. Similar to what was observed in the human prostate cancer cell lines, the Myc-CaP/CR cell line was found to have increased full-length AR expression by both quantitative ELISA (FIG. 13A) and intracellular staining compared to the Myc-CaP/AS cell line (FIG. 13B). While analysis of RNA transcripts showed an increase in the murine AR splice variants mAR-V2 and mAR-V4, these splice variants were similarly several fold lower in expression than the full-length AR (FIG. 13C). To study the expression of AR in vivo, FVB mice were inoculated with Myc-CaP/AS cells, and then given either a sham treatment or castration by administration of a GnRH antagonist (degarelix). Animals were followed for tumor growth (FIG. 13D), and recurrent tumors were collected and CD45− cells were analyzed for AR expression by intracellular staining. Tumors that recurred following androgen deprivation were found to have increased AR expression, both in terms of frequency of CD45− cells with detectable expression of the AR, as well as the amplitude of AR expression within these cells (FIG. 13E).

Figures 14A, 14B:
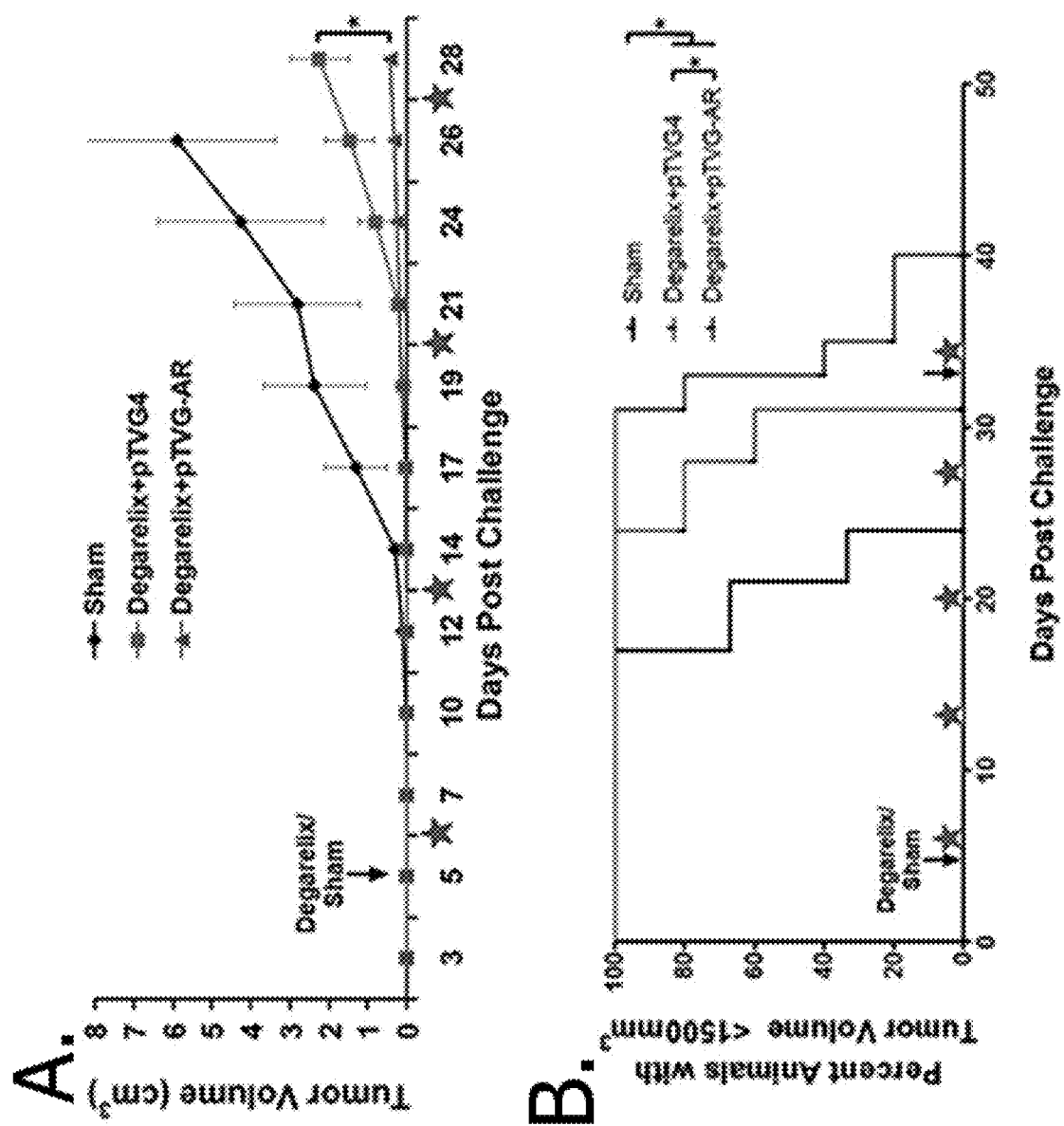
FIG. 14A shows androgen deprivation combined with immunization using pTVG-AR delayed the recurrence of castrate-resistant Myc-CaP tumors. Myc-CaP/AS tumor-bearing mice with palpable tumors were given a sham-treatment (n=3) or degarelix along with biweekly immunization with pTVG-AR (n=5) or empty vector (n=5) and followed for tumor growth (tumor volumes). Results are representative of three independent studies.
FIG. 14B shows the Kaplan Meier curve for FIG. 14A. Results are representative of three independent studies.
Figures 14C, 14D:
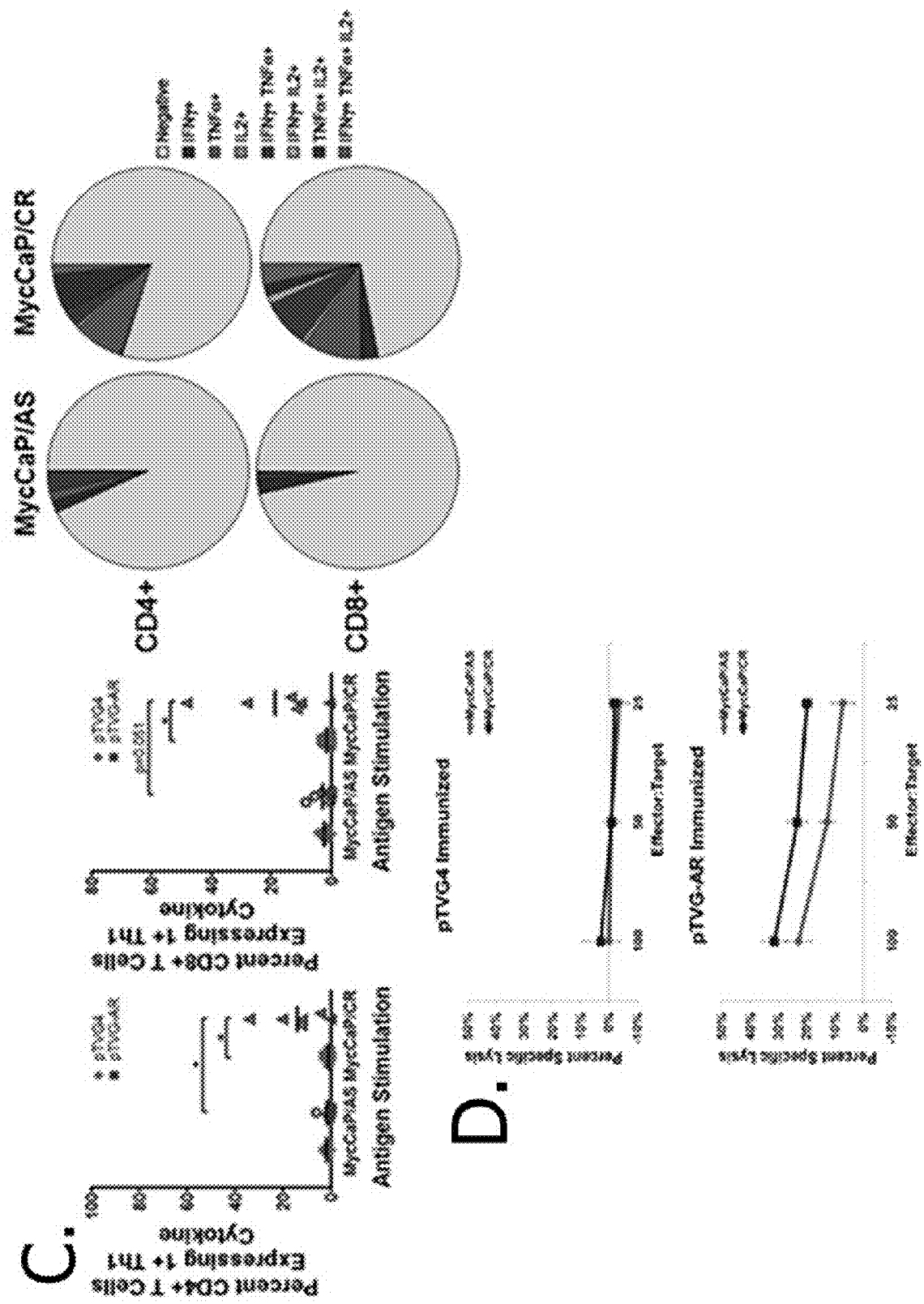
FIG. 14C shows splenocytes from androgen-deprived animals immunized with pTVG4 or pTVG-AR cultured with Myc-CaP/AS or Myc-CaP/CR cells and assessed for CD4+ and CD8+ T-cell intracellular cytokine expression (with polyfunctional expression quantified in side pie charts).
FIG. 14D shows splenocytes from androgen-deprived animals immunized with pTVG4 or pTVG-AR cultured with Myc-CaP/AS or Myc-CaP/CR cells and assessed for cytotoxicity.
Figures 14E, 14F, 14G:
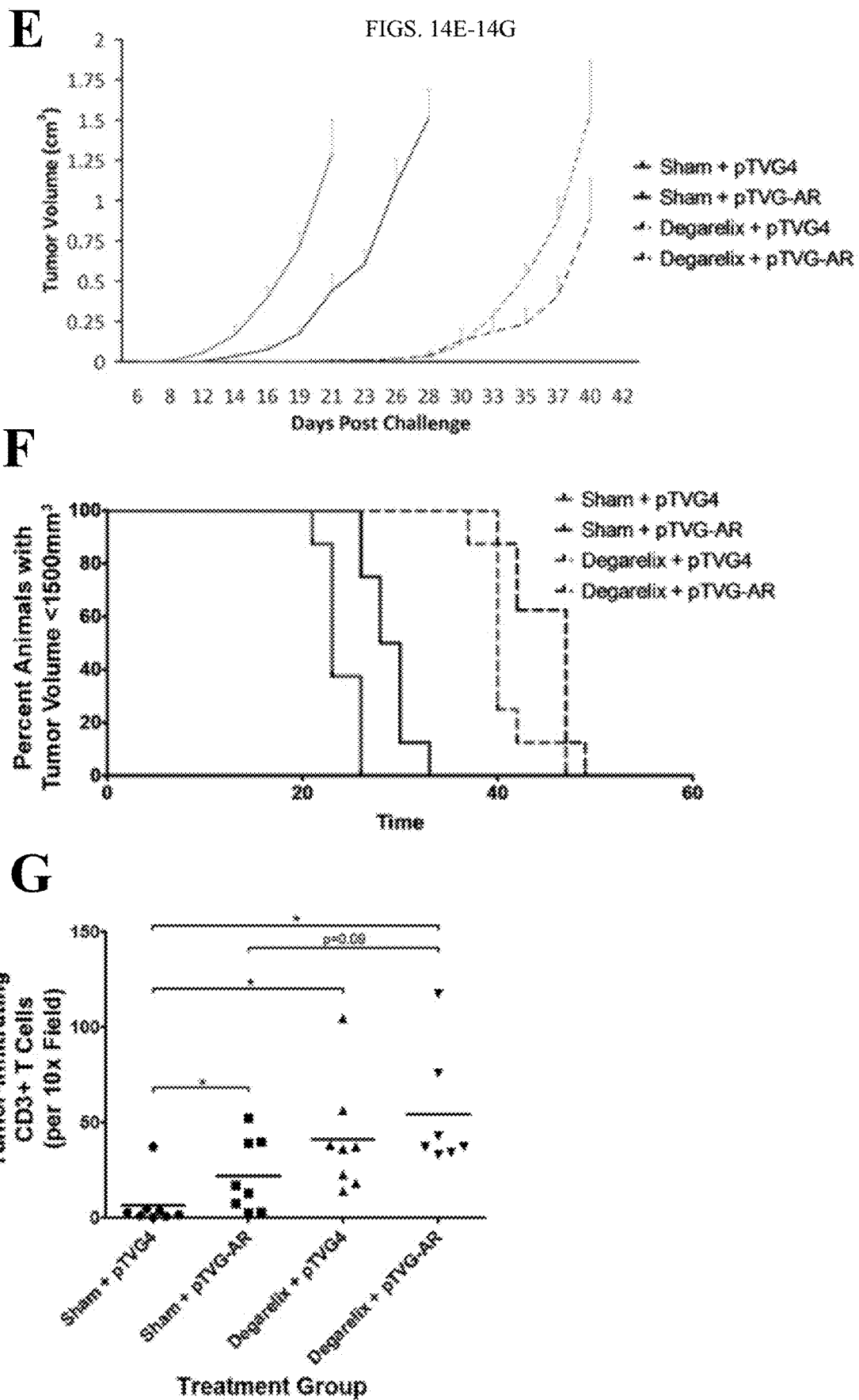
FIG. 14E demonstrates immunization with pTVG-AR delays tumor growth in the presence or absence of ADT, and results in increased tumor-infiltrating T cells. Myc-CaP/AS tumor-bearing mice were given degarelix or sham treatments, then immunized with either pTVG-AR or pTVG4 control, and assayed for tumor growth (tumor volumes).
FIG. 14F shows Kaplan Meier plots for mice of FIG. 14E.
FIG. 14G shows analysis of tumor collected from FIG. 14E for the frequency of infiltrating T cells by IHC. * indicates p<0.05 by Mann-Whitney U test.

Immunization with pTVG-AR Delays the Growth of Castration-Resistant Prostate Tumors Following Androgen Deprivation This Example also demonstrates that androgen deprivation in combination with AR-targeted vaccination delays the outgrowth of castration-resistant tumors by specifically targeting cells overexpressing AR. Mice were implanted with Myc-CaP/AS tumors, and mice with established tumors were given either a sham treatment or degarelix. Mice treated with degarelix were then randomized to immunization with either a DNA vaccine encoding the AR LBD (pTVG-AR), or an empty vector control (pTVG4). The combination treatment with degarelix and pTVG-AR was found to delay tumor growth compared to treatment with degarelix and control vaccine (FIG. 14A-B). Additionally, when animals were evaluated for evidence of immune responses against the Myc-CaP/AS or Myc-CaP/CR cell lines, animals immunized with pTVG-AR were found to have increased immune responses against the castration-resistant cell line, both in terms of cytokine expression (FIG. 14C) as well as cytotoxicity (FIG. 14D). In parallel studies, we found that immunization of Myc-CaP/AS-bearing mice with pTVG-AR resulted in an increased frequency of tumor-infiltrating CD3+ T cells, and this was further increased when vaccination was combined with degarelix treatment (FIG. 14E).

Figures 15A, 15B:
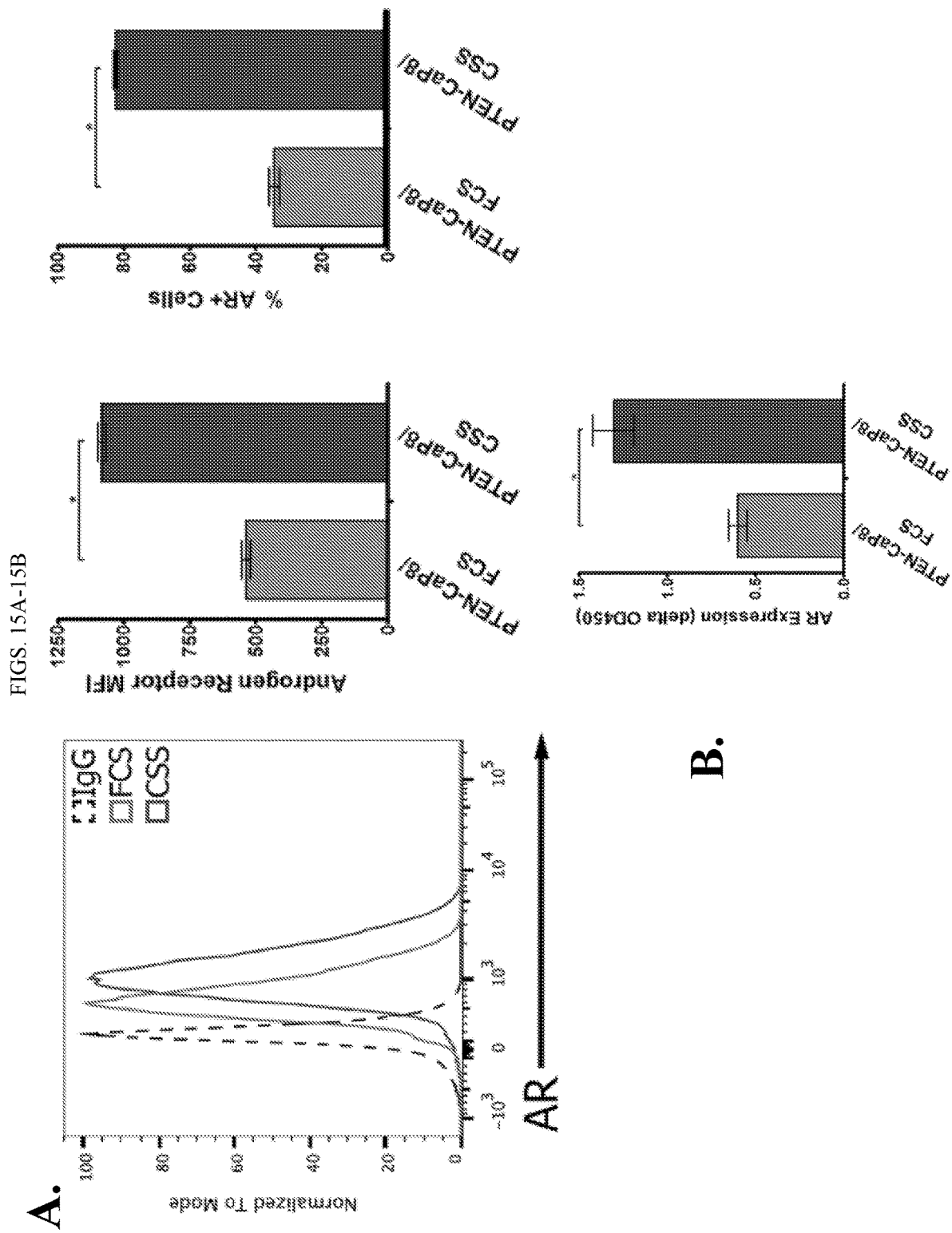
FIG. 15A shows androgen deprivation increases AR expression in PTEN-deficient tumors, and immunization with pTVG-AR delays the development of castrate-resistant prostate tumors in Pten−/− mice. PTEN-CaP8 tumor cells cultured in androgen-replete (FCS) or androgen-deprived (CSS) medium were analyzed for AR expression by intracellular staining (quantified for amplitude and expression in side panels). * indicates p<0.05 by student's t-test.
FIG. 15B shows the results of PTEN-CaP8 tumor cells cultured in androgen-replete (FCS) or androgen-deprived (CSS) medium analyzed for AR expression by quantitative ELISA. * indicates p<0.05 by student's t-test.
Figure 15C:
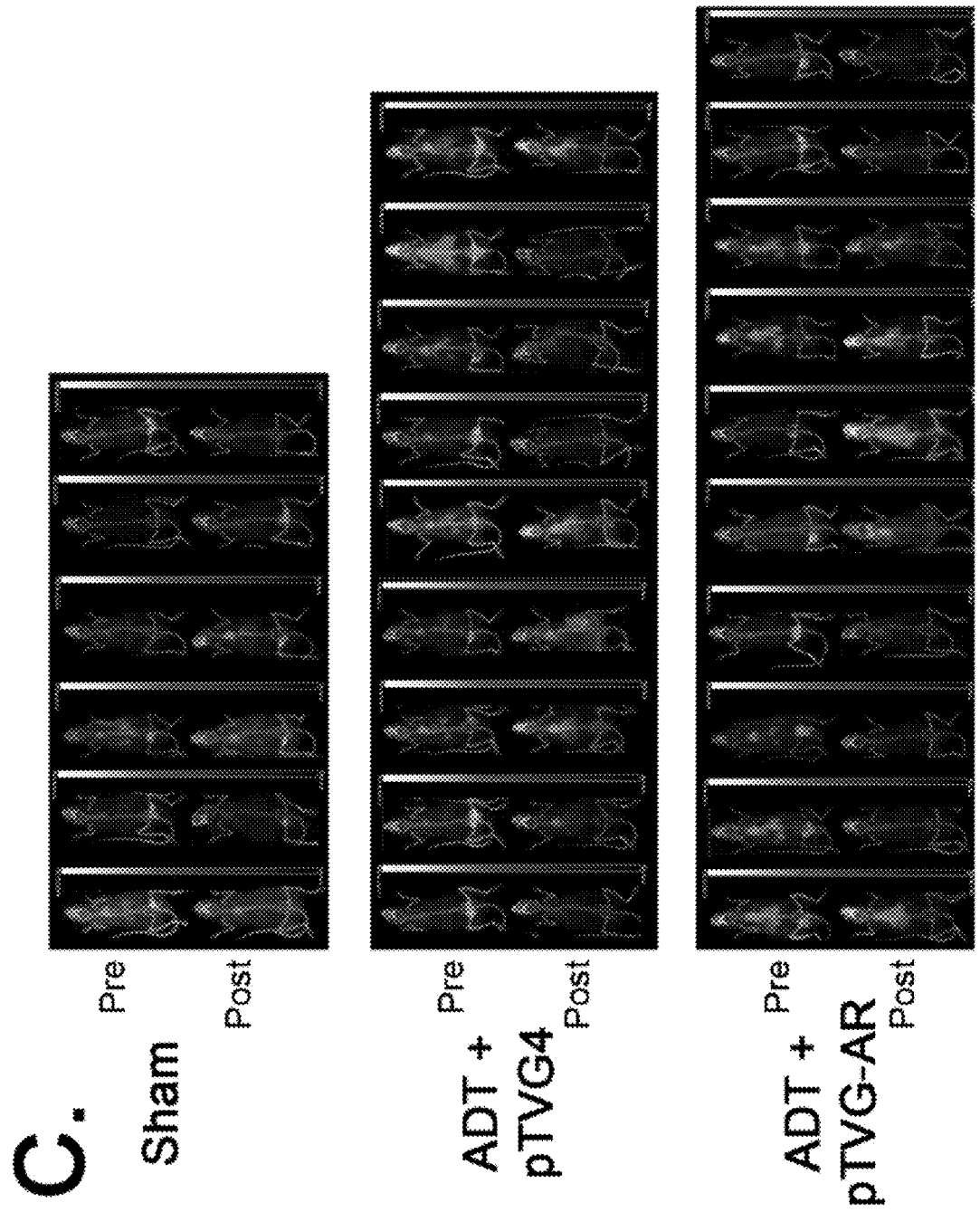
FIG. 15C shows the results of twenty-week old PbCre+ PTEN$^{fl/fl}$ mice given a sham treatment (n=9), or degarelix along with biweekly immunization with pTVG4 (n=13) or pTVG-AR (n=13), for five months. One week prior to initiation and completion of treatment, animals were administered $^{124}$I-CLR1404 and PET/CT scanned 96 hr post intravenous injection (PET/CT images pre- and post-treatment). Signal greater than sixty percent of the max PET signal was used to calculate the mean and max percent injected dose (% ID/$g_{tissue}$) for tumor, and was normalized to background muscle uptake.
Figures 15D, 15E, 15F, 15G, 15H:
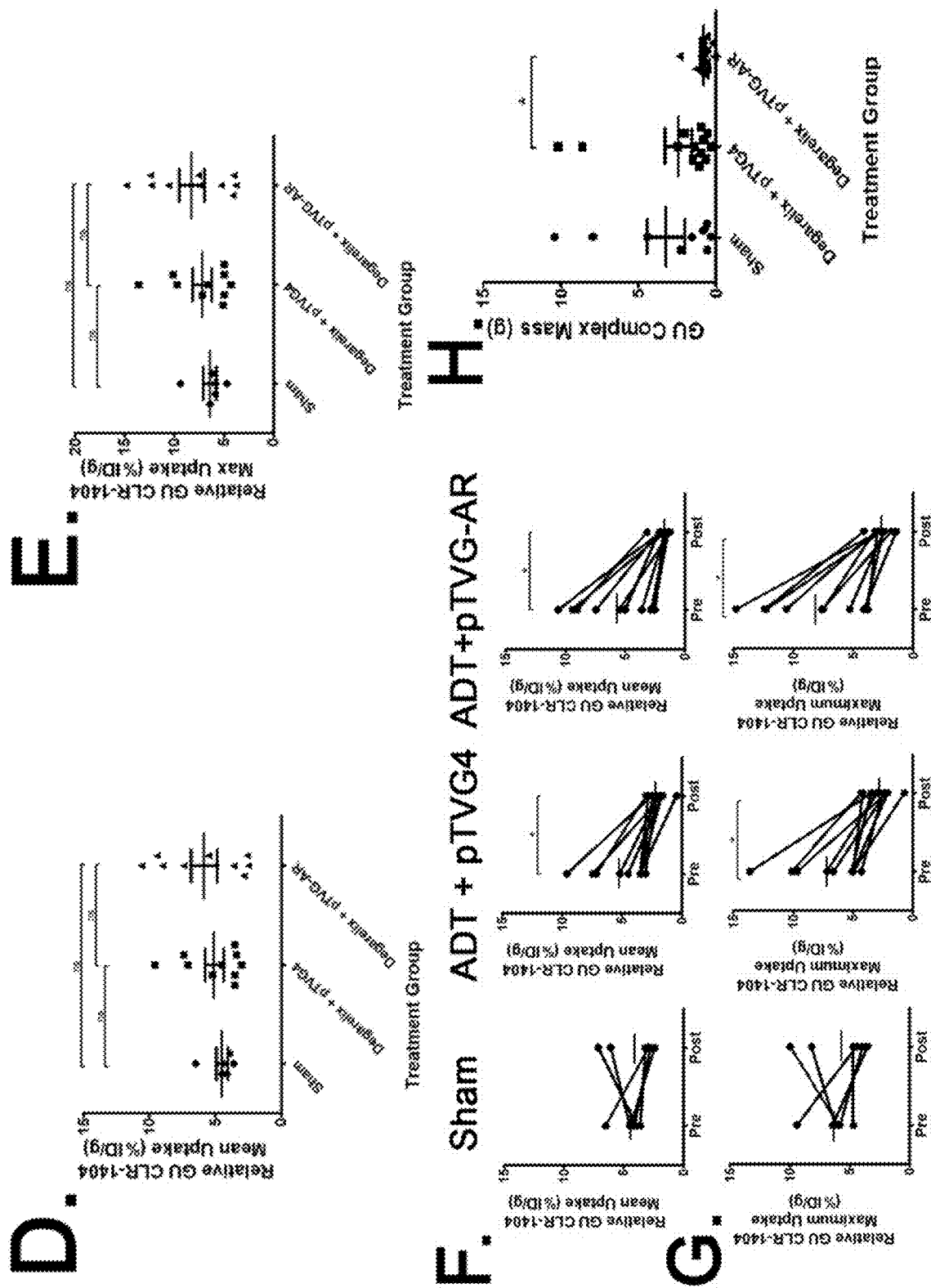
FIG. 15D shows the pre-treatment mean $^{124}$I-CLR1404 uptake for randomization of treatment groups. * indicates p<0.05 by Mann-Whitney U test.
FIG. 15E shows the pre-treatment maximum $^{124}$I-CLR1404 uptake for randomization of treatment groups. * indicates p<0.05 by Mann-Whitney U test.
FIG. 15F shows changes in % ID/$g_{mean}$ pre- to post-treatment calculated (mean values shown by solid horizontal bars). * indicates p<0.05 by Mann-Whitney U test.
FIG. 15G shows % ID/$g_{mean}$ pre- to post-treatment calculated (mean values shown by solid horizontal bars). * indicates p<0.05 by Mann-Whitney U test.
FIG. 15H shows genitourinary complex masses collected during necropsy and analyzed. * indicates p<0.05 by Mann-Whitney U test.

Androgen Deprivation Increases AR Expression in PTEN-Deficient Tumors, and Immunization with pTVG-AR, Combined with ADT, Decreased Growth of Castration-Resistant Tumors As an additional, relevant model of human prostate cancer, this Example utilized the PbCre PTENfl/fl mice, in which prostate-specific expression of the Cre recombinase drives deletion of the PTEN tumor suppression and the formation of autochthonous prostate tumors. The PTEN-CaP8 cell line (derived from one of these autochthonous tumors) was similarly cultured in androgen-replete and androgen-deprived medium. As shown in FIG. 15A-B, androgen-deprivation resulted in a significant increase in AR protein expression, similar to the human prostate cancer cell lines and Myc-CaP cell lines above. Twenty-week old PbCre+ PTENfl/fl mice were then given either a sham treatment, or degarelix in combination with pTVG-AR vaccine or vector control. To non-invasively monitor tumor growth, as well as to randomize animals prior to treatment, we utilized micro-PET/CT imaging, employing the novel radiotracer 124I-CLR1404, which is a radioiodinated alkylphosphocholine (APC) analog that has shown selective tumor uptake in >95% of malignant models to date (30). Animals were intravenously administered 124I-CLR1404 and subsequently PET/CT scanned within one week prior to initiation and completion of therapy (FIG. 15C), and imaging results were analyzed for mean and maximum tumor uptake. Analysis of tumors pre-treatment showed no difference between mean and maximum tumor uptake (FIG. 15D-E). While some animals with large tumors died prior to the last imaging session, and hence not all animals underwent post-treatment imaging, notwithstanding, androgen deprivation was shown to result in decreased 124I-CLR1404 mean and max tumor uptake, as shown in FIG. 15F and FIG. 15G, respectively. No significant difference in % ID/gmean or % ID/gmax was detected post-treatment between animals receiving ADT and control vaccine versus animals receiving ADT and AR-targeted vaccine. However, as measured during necropsy, animals treated with degarelix and pTVG-AR had significantly smaller tumor volumes, as determined by genitourinary complex weight, compared to animals receiving degarelix and pTVG4 (FIG. 15H).

Discussion

This Example demonstrates that androgen deprivation results in increased full-length AR expression in vitro and in vivo that persists over time, and that this increased AR expression is associated with these cells being better targets for AR-specific T cells. Furthermore, a DNA vaccine encoding the AR LBD enhanced immune responses that preferentially recognized and lysed castrate-resistant prostate cancer cells, and delayed the recurrence of castrate-resistant disease when combined with ADT. A vaccine targeting the AR may be preferred over other antigen-specific vaccines when specifically combined with ADT by targeting a major mechanism of resistance that drives castrate-resistant tumor growth.

In summary, this Example shows that increased AR expression in prostate cancer cells following ADT results in enhanced recognition and lysis by AR-specific T cells. The combination of ADT and AR-specific immunization in vivo enhanced anti-tumor T cell immunity, as well as delayed the recurrence of castrate-resistant tumors. These studies provide a rationale for combining ADT with AR-targeted immunization, an approach that is being evaluated in a Phase I clinical trial (NCT02411786).

Example 6

Immunization Elicits PD-L1 Expression in Tumors and PD-1/PD-L1 Blockage can Increase the Anti-Tumor Efficacy of DNA Vaccination Using different tumor antigen systems we have found that DNA vaccination can elicit PD-L1 expression in tumors as a result of tumor-specific T cells elicited that secrete IFNγ. Specifically, we have reported that tumors expressing a model antigen had an increase in PD-L1 expression following immunization with a DNA vaccine encoding that antigen (Rekoske, B. T., H. A. Smith, B. M. Olson, B. B. Maricque, and D. G. McNeel. (2015). "PD-1 or PD-L1 Blockade Restores Antitumor Efficacy Following SSX2 Epitope-Modified DNA Vaccine Immunization." *Cancer Immunol Res.* 3:946-55). If the immunization was modified to elicit CD8+ T cells with higher PD-1 expression, this resulted in an inferior anti-tumor response. Combining vaccination with anti-PD-1 or anti-PD-L1 antibody treatment resulted in a greater anti-tumor response and eradication of tumors in some animals (Rekoske, B. T., H. A. Smith, B. M. Olson, B. B. Maricque, and D. G. McNeel. (2015). "PD-1 or PD-L1 Blockade Restores Antitumor Efficacy Following SSX2 Epitope-Modified DNA Vaccine Immunization." *Cancer Immunol Res.* 3:946-55). We have recently identified that this also occurs following human immunization using cryopreserved blood samples collected from patients with advanced prostate cancer treated with a DNA vaccine encoding prostatic acid phosphatase (PAP).

Figures 9A, 9B, 9C:
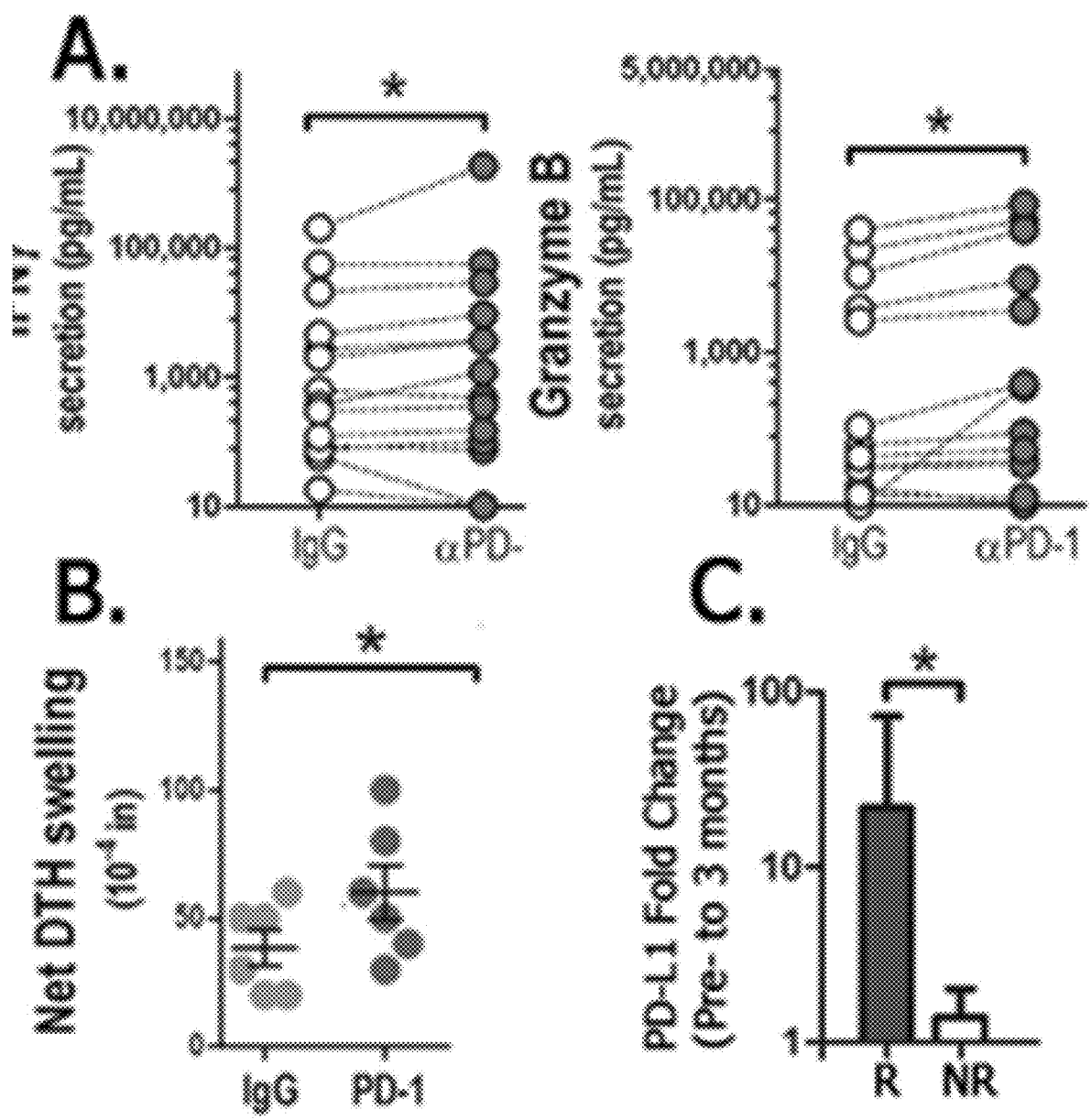
FIG. 9A shows PBMC from patients previously immunized with a PAP-targeting vaccine were cultured in vitro for 72 hours with PAP in the presence of a PD-1-blocking antibody (or IgG control), and measured for IFNγ (left panel) or granzyme B (right panel) secretion by ELISA.
FIG. 9B shows PBMC obtained from patients after immunization were injected into the footpads of NOD/SCID mice with PAP protein and PD-1 blocking antibody (or IgG control), and 24 hours later, footpad swelling was measured.
FIG. 9C shows that PD-L1 expression was measured on circulating tumor cells from patients with persistent PAP-specific Th1-biased immune responses (R) vs non-responders (NR) following immunization with a DNA vaccine targeting PAP. The ratio PD-L1 MFI on post-treatment samples compared to pre-treatment samples is shown. In all panels, * indicates $p<0.05$ by Student's t-test.

Using in vitro and trans vivo methods, we found that immune responses to PAP were detected and/or augmented when combined with PD-1 blockade (FIG. 9A, B). Moreover, we detected increased expression of PD-L1 on circulating tumor cells following DNA vaccination, and we found that higher expression correlated with the development of persistent antigen-specific IFNγ-secreting T cell immune responses (FIG. 9C). We observed similar results in blood samples from patients treated with sipuleucel-T, an FDA-approved vaccine for prostate cancer which targets the same PAP antigen (data not shown). Together, these data provide evidence to support combining anti-tumor vaccines with a PD-1 pathway inhibitor. Briefly, FIG. 9A shows PBMC from patients previously immunized with a PAP-targeting vaccine were cultured in vitro for 72 hours with PAP in the presence of a PD-1-blocking antibody (or IgG control), and measured for IFNγ (left panel) or granzyme B (right panel) secretion by ELISA. FIG. 9B shows PBMC obtained from patients after immunization were injected into the footpads of NOD/SCID mice with PAP protein and PD-1 blocking antibody (or IgG control), and 24 hours later, footpad swelling was measured. FIG. 9C, PD-L1 expression was measured on circulating tumor cells from patients with persistent PAP-specific Th1-biased immune responses (R) vs. non-responders (NR) following immunization with a DNA vaccine targeting PAP. The ratio of PD-L1 MFI on post-treatment samples compared to pre-treatment samples is shown. In all panels, * indicates $p<0.05$ by Student's t-test.

More recent preliminary data also suggest that targeting the PD-1/PD-L1 pathway in combination with an AR-targeting vaccine is a rationale combination to circumvent this means of tumor-mediated immune suppression. In Myc-CaP tumor-bearing animals treated with AD and immunized with pTVG-AR (as in FIG. 8), CD8+ T cells were found to have elevated PD-1 expression (FIG. 10A). Additionally, it was observed in other models following the generation of antigen-specific immune responses following immunization, some recurrent tumors had elevated PD-L1 expression (FIG. 10B). When AR-targeted immunization was combined along with a PD-1 blocking antibody, this treatment significantly delayed tumor growth compared to immunization with pTVG-AR alone (FIG. 10C). Furthermore, combining ADT with AR-directed immunization and PD-1 blockade further delayed tumor growth (FIG. 10D). Together, these finding suggest that PD-1 pathway inhibitors would be an effective means to target resistance to combined ADT and AR-directed immunization and could prevent (or significantly delay) the formation of the lethal, castrate-resistant form of prostate cancer.

Briefly, FVB mice were implanted subcutaneously with MycCaP tumor cells, treated the following day with degarelix, and the following day were immunized with pTVG4 (vector control) or pTVG-AR. At the time of tumor outgrowth, animals were analyzed for PD-1 expression on splenic CD8+ T-cells (FIG. 10A) and PD-L1 expression on CD45− tumor cells (FIG. 10B). For FIG. 10C, FVB mice (n=5) were implanted with MycCaP tumors, and the following day immunized with pTVG-AR (repeated weekly), without castration, and each day following vaccination were treated with a PD-1-blocking antibody or control, and followed for tumor growth. For FIG. 10D, MycCaP tumor-bearing FVB mice were treated with degarelix, pTVG-AR, and anti-PD-1 (n=5) or IgG control (n=9), and followed for tumor growth. In all panels, * indicates $p<0.05$ by Student's t-test.

Example 7

Clinical Trial Design Using AR-Targeted Vaccination in Combination with Androgen Deprivation and T-Cell Checkpoint Blockade An open-label, randomized pilot clinical trial is to be performed, with a maximum of 50 patients with newly diagnosed prostate cancer. The patients are randomly assigned to one of three treatment arms below.

Study Objectives:

The primary clinical objectives of the trial is safety and pathological complete response rate per study arm. Primary objectives include evaluating the safety of combination androgen deprivation, alone or in combination pTVG-AR DNA vaccine with or without pembrolizumab, in patients with newly diagnosed prostate cancer; and to determine the pathological complete response rate in patients with prostate cancer treated with combination androgen deprivation (LHRH agonist, abiraterone acetate, and apalutamide) or with pTVG-AR, with or without pembrolizumab, prior to radical prostatectomy.

Secondary objectives include determining one year PSA progression-free survival rates; determining whether treatment with pTVG-AR, with or without pembrolizumab, elicits persistent systemic AR-specific Th1-biased T-cell responses, and determining whether treatment with pTVG-AR, with or without pembrolizumab, elicits increased prostate tissue-infiltrating CD8+ T cells.

Subject Population:

Eligible subjects are patients with newly diagnosed prostate cancer who are planning to undergo radical prostatectomy as extirpative treatment. Subjects need not be HLA-A2 positive, however serological typing is performed to identify patients for epitope-specific T-cell analyses. In previous trials at our institution, we have found ~50% of patients were HLA-A2-expressing, consequently we anticipate ~50% of patients are available for these analysis.

Trial Design:

This will be a randomized, open-label, multi-institution pilot trial designed to evaluate the immunological and clinical effect of a DNA vaccine encoding AR with rhGM-CSF adjuvant given with or without pembrolizumab. Study arms will be defined as follows:

Arm 1: Leuprolide depot (or equivalent) 22.5 mg intramuscular injection day 1, day 85
  Abiraterone acetate 1000 mg p.o. daily, beginning day 1 until day prior to surgery
  Prednisone 5 mg p.o. daily, beginning day 1 until 1 week after surgery, then taper
  Apalutamide 240 mg p.o. daily, beginning day 1 until day prior to surgery Arm 2: Leuprolide depot (or equivalent) 22.5 mg intramuscular injection day 1, day 85
  Abiraterone acetate 1000 mg p.o. daily, beginning day 1 until day prior to surgery
  Prednisone 5 mg p.o. daily, beginning day 1 until 1 week after surgery, then taper
  Apalutamide 240 mg p.o. daily, beginning day 1 until day prior to surgery
  pTVG-AR (100 µg) with rhGM-CSF (208 µg) administered intradermally (i.d.) biweekly 6 times, beginning day 1

Arm 3: Leuprolide depot (or equivalent) 22.5 mg intramuscular injection day 1, day 85
  Abiraterone acetate 1000 mg p.o. daily, beginning day 1 until day prior to surgery
  Prednisone 5 mg p.o. daily, beginning day 1 until 1 week after surgery, then taper
  Apalutamide 240 mg p.o. daily, beginning day 1 until day prior to surgery
  pTVG-AR (100 µg) with rhGM-CSF (208 µg) administered intradermally (i.d.) every 3 weeks 8 times, beginning day 1
  Pembrolizumab 2 mg/kg, administered intravenously over 30 minutes, every 3 weeks 8 times, beginning day 1, each dose following pTVG-AR vaccination A total of 50 eligible patients (10 in Arm 1, 20 in Arm 2 and 20 in Arm 3) will be randomized. All subjects are followed for adverse events; if adverse events attributed to study treatment exceed the tolerability limit (≥33% grade>2 toxicity, or ≥10% grade>3 toxicity), further accrual would halt.

Measurement of Effect:

Patients eligible for this trial will not have metastatic disease at the time of enrollment.

Pathological evaluation: Prostate tissues obtained by biopsy pre-treatment and at the time of prostatectomy, will be reviewed and graded by a single pathologist (Dr. Jiaoti Huang, MD PhD or designee) as per standard clinical pathology review. The absence of identifiable prostate cancer at the time of prostatectomy will be used to define a pathological complete response.

Serum PSA evaluation: Serum PSA is expected to be undetectable following prostatectomy in the absence of residual/recurrent disease. Hence PSA progression will be defined as a detectable PSA (above the clinical lab's lower limit of detection) at any point after 3 months after the date of prostatectomy, and confirmed by a second reading at least 2 weeks later.

Safety:

All subjects are observed at every visit during the period of treatment for symptoms assessment. Laboratory analyses is performed at regular intervals for evidence of adverse events. These clinical laboratory studies include complete blood counts, creatinine, liver function tests, PSA, serum aldolase (for muscle-related toxicity assessment), and anti-nuclear antibodies. Adverse events are graded by the current version (4.0) of the NCI Common Terminology Criteria. The number and severity of toxicity incidents are analyzed descriptively in tabular format.

Immunological Monitoring:

Blood will be collected by either peripheral blood draw (up to 210 mL) or leukapheresis (50-100 mL) pre-immunization, after 3 months of treatment, at the time of prostatectomy, and at 3 months, 6 months, and 12 months after prostatectomy, for immunological monitoring. From the heparinized blood, peripheral blood mononuclear cells (PBMC) will be prepared by density centrifugation over Ficoll-Paque using standard techniques. PBMC will be used directly for analysis, and residual material cryopreserved in liquid nitrogen using 90% autologous serum collected at the time of blood draw, or 90% fetal calf serum, and 10% DMSO. Sera will be prepared from the red-top tubes and stored in aliquots at −80° C. for antibody analyses. IFNγ and granzyme B ELISPOT analysis, and ELISA tests for antigen-specific antibodies, will be the primary methods of analysis. The primary antigens tested will be AR (experimental), PSA (negative control), and tetanus toxoid (positive control). The primary immune analysis will be conducted at the 6-month post-surgery time point, and compared with the pre-treatment time point, and for patients to be evaluable for immune response (primary endpoint), blood (PBMC and serum) from this time point must be available for analysis. However, immune monitoring will be conducted at the other time points indicated in secondary analyses to evaluate kinetic measures of immunity, and evaluate whether durable immune responses of particular phenotypes are elicited and/or maintained. Assays may be conducted at the time of sample collection (fresh) and/or batched and performed at one time from multiple cryopreserved samples collected at different time points. Other methods of effector and regulatory T-cell response to AR and other human tissue antigens may be used.

Quantitative Assessment of AR-Specific CD8+ T-Cell Effector Immunity AR-Specific IFNγ- and Granzyme B-Secreting T-Cell Precursor Frequency Quantification by ELISPOT:

ELISPOT will be used as the preferred methodology, as it permits analysis of low-frequency events (LOD~1:100,000 cells) and also permits simultaneous analysis of cryopreserved batched specimens [22]. IFNγ and granzyme B will be preferred analytes evaluated, as these are specifically associated with inflammatory/tissue-destructive (Th1-type, cytolytic) immune responses. Specifically, cryopreserved PBMC from subjects at the various time points will be thawed, rested, and then transferred to 96-well nitrocellulose microtiter (ELISPOT) plates previously coated with monoclonal capture antibodies specific for IFNγ or granzyme B. $10^5$ cells per well will be cultured in the presence of media (RPMI 1640 supplemented with L-glutamine, penicillin/streptomycin, β-mercaptoethanol and 10% human AB serum) only (no antigen), 2 µg/ml AR protein, 2 µg/ml PSA protein (negative control), 2 µg/ml of peptide libraries specific for AR or control, 250 ng/ml tetanus toxoid, or 2.5 µg/ml PHA (positive mitogenic control) for 24-48 hours. Plates will then be washed with PBS containing 0.05% Tween-20 and incubated for 2.5 hours at room temperature with 50 µl/well PBS containing 5 µg/ml biotinylated detection antibodies for either IFNγ or granzyme B. After incubation, wells will be washed with PBS, and further incubated with 100 µl/well streptavidin-labeled alkaline phosphatase (BioRad, Hercules, Calif.) and then developed with 100 µl/well BCIP/NBT colorimetric substrate (Bio-Rad). The colorimetric reaction will be stopped by rinsing the plates under cool tap water, and wells will be allowed to dry completely before spots are enumerated with an ELISPOT automatic plate reader.

Reporting and Response Definition:

Results will be presented as previously reported as the mean (+/−standard deviation) number of spot-forming-units (sfu) per $10^6$ cells (frequency), calculated by subtracting the mean number of spots obtained from the no antigen control wells from the mean number obtained in the experimental wells, normalized to $10^6$ starting PBMC, from 8-well replicate assays [23]. Comparison of experimental wells with control, no antigen, wells will be performed using a two-sample t-test, with p<0.05 (two-sided) defined as a significant antigen-specific T-cell response. A significant antigen-specific response resulting from immunization will then be defined as a AR-specific response detectable at the 6-month post-surgery time point (or other post-treatment time point evaluated) that is significantly higher than to media only (as above), at least 3-fold higher than the mean baseline value, and with a frequency>10 per $10^6$ PBMC.

Assessment of Antigen-Specific Antibody Immunity: Enzyme-Linked Immunosorbent Assay (ELISA) for the Detection of Antibodies Responses to AR:

The presence of a coexisting humoral immune response to AR (or other antigens) will be evaluated by ELISA using an indirect method similar to that described previously [61]. Specifically, Immulon-4 ELISA plates (Dynex Technologies Inc.) will be coated with 2 µg/ml purified AR LBD protein (Research Diagnostics, Inc., or other antigens or commercial sources) in 0.1 M $NaHCO_3/Na_2CO_3$ buffer (pH 9.6) overnight at 4° C. After blocking with PBS/1% BSA for 1 hour at room temperature, wells will be washed with PBS+0.05% Tween-20 (PBS-Tween) and then incubated for 1 hour with human sera diluted 1:25, 1:50, 1:100 and 1:200. After washing, plates will then be sequentially incubated with a peroxidase-conjugated anti-human IgG detection antibody (Amersham), followed by peroxidase enzyme TMB substrate (Kierkegaard and Perry Laboratories). The color reaction will be stopped with 1N H2504 and the optical density measured at 450 nm. Antibody titers for AR-specific IgG antibodies will be determined as previously described [61].

Reporting and Response Definition:

These are not strictly quantitative assays. IgG response will be reported graphically demonstrating sera dilution curves, and by titer—defined as the highest sera dilution at which IgG responses are detectable above the mean+3 standard deviations of the negative control. A positive IgG response resulting from immunization will be defined as an antigen-specific (anti-AR) IgG titer at least 4-fold higher than the baseline titer detectable at the 6-month post-treatment time point (or other post-treatment time point evaluated).

Histopathology Evaluation:

Tissue biopsies obtained pre-treatment and at the time of prostatectomy will be available from all subjects. The purpose of these studies is first to determine whether treatment with androgen deprivation alone (ARM 1) results in an increase in CD8+ T cells, and whether this is further increased by the use of an AR-targeting vaccine (ARM 2) and further yet with pembrolizumab (ARM 3). This will be determined by standard immunohistochemistry, and by quantitative flow cytometry (when feasible with fresh tissue). As an exploratory method, the frequency of CD8+ T cells, relative to other populations, will also be determined by mRNA analysis of frozen or paraffin-embedded tissue samples. As a further exploratory method, the frequency of specific CD8+ T cell populations will be determined by TCR sequencing using frozen tissue samples (Adaptive Biotechnologies, Seattle, Wash.).

Secondary goals of the histopathology evaluation will be to determine whether immunization with pTVG-AR affects PD-L1 expression in the tumor (likely by eliciting tumor antigen-specific T cells secreting IFNγ), and whether treatment increases expression of other T-cell regulatory ligands on T cells (PD-1, CTLA-4, TIM-3, BTLA, VISTA, LAG-3) or tumors (e.g. HVEM, phosphatidyl serine, PD-L2). Consequently, biopsy specimens obtained pre-treatment and after 12 weeks will be stained with antibodies specific for CD3, CD4, CD8, FoxP3, PD-1, CTLA-4, TIM3, BTLA, VISTA, LAG-3, PD-L1, PD-L2, phosphatidyl serine, HVEM and potentially other markers. Staining and quantification will be reviewed by a pathologist blinded to the treatment groups to determine CD8+ T cells per field, CD4+FoxP3+ (Treg):CD8+ T cell ratio, PD-L1 expression, and whether these or the expression of CD8+ T cells expressing one regulatory receptors (or tumor cells expressing one or more regulatory ligands) change from pre-treatment to the prostatectomy time point.

At the University of Wisconsin, samples will be transported to the UWCCC TRIP (Translational Research Initiatives in Pathology) lab for formalin fixation, paraffin embedding, sectioning, H&E staining, and ultimately for IHC analysis as described above.

Example 8

Figure 16:
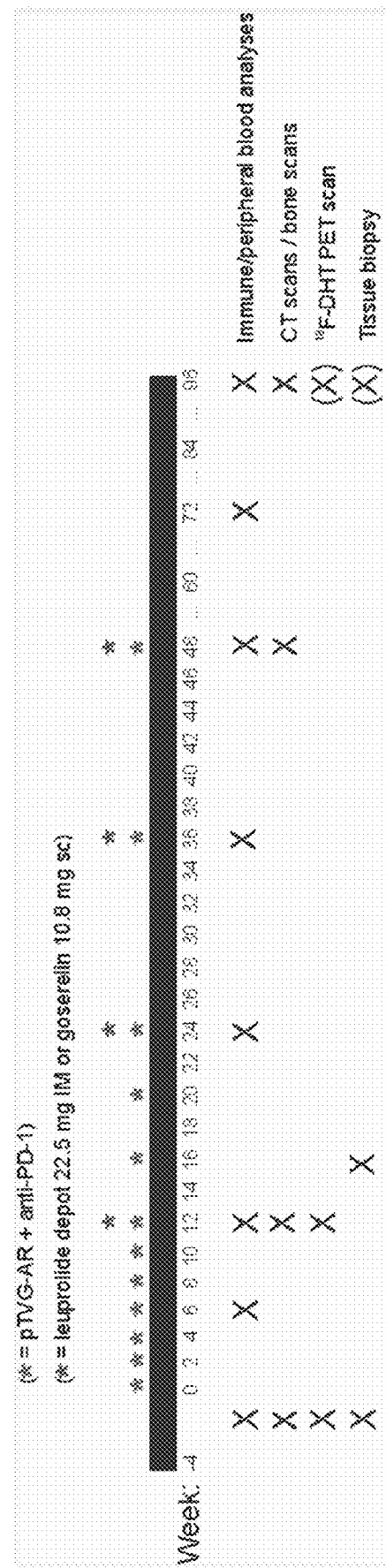
FIG. 16 is a schematic of a treatment using an anti-androgen therapy leuprolide in combination with a DNA vaccine and an anti-PD1 therapy.

Similar to Example 7, a suitable dosage regimen for the combination treatment using vaccine, ADT and a PD-1 pathway blockage is diagramed in FIG. 16. Suitable testing parameters are shown under the timeline and will be performed as discussed in Example 7.

Each publication, patent, and patent publication cited in this disclosure is incorporated in reference herein in its entirety. The present invention is not intended to be limited to the foregoing examples, but encompasses all such modifications and variations as come within the scope of the appended claims.

REFERENCES FROM EXAMPLE 5, each is incorporated by reference in its entirety
1. Colluru V T, Johnson L E, Olson B M, McNeel D G. Preclinical and clinical development of DNA vaccines for prostate cancer. Urol Oncol. 2016; 34:193-204.
2. Hodge J W, Ardiani A, Farsaci B, Kwilas A R, Gameiro S R. The tipping point for combination therapy: cancer vaccines with radiation, chemotherapy, or targeted small molecule inhibitors. Semin Oncol. 2012; 39:323-39.
3. Ardiani A, Gameiro S R, Kwilas A R, Donahue R N, Hodge J W. Androgen deprivation therapy sensitizes prostate cancer cells to T-cell killing through androgen receptor dependent modulation of the apoptotic pathway. Oncotarget. 2014; 5:9335-48.
4. Mercader M, Bodner B K, Moser M T, Kwon P S, Park E S, Manecke R G, et al. T cell infiltration of the prostate induced by androgen withdrawal in patients with prostate cancer. Proc Natl Acad Sci USA. 2001; 98:14565-70.
5. Morse M D, McNeel D G. Prostate Cancer Patients Treated with Androgen Deprivation Therapy Develop Persistent Changes in Adaptive Immune Responses. Human immunology. 2010; 71:496-504.
6. Morse M D, McNeel D G. T cells localized to the androgen-deprived prostate are TH1 and TH17 biased. Prostate. 2012; 72:1239-47.
7. Roden A C, Moser M T, Tri S D, Mercader M, Kuntz S M, Dong H, et al. Augmentation of T cell levels and responses induced by androgen deprivation. J Immunol. 2004; 173:6098-108.
8. Mercader M, Sengupta S, Bodner B K, Manecke R G, Cosar E F, Moser M T, et al. Early effects of pharmacological androgen deprivation in human prostate cancer. BJU Int. 2007; 99:60-7.
9. Gannon P O, Poisson A O, Delvoye N, Lapointe R, Mes-Masson A M, Saad F. Characterization of the intra-prostatic immune cell infiltration in androgen-deprived prostate cancer patients. Journal of immunological methods. 2009; 348:9-17.
10. Shen Y C, Kochel C, Francica B, Alme A, Nirschl C, Nirschl T, et al. Combining androgen deprivation with immune checkpoint blockade delays the development of castration resistance in a murine model of prostate cancer. AACR 106th Annual Meeting 2015; 2015; Philadelphia, Pa.
11. Akins E J, Moore M L, Tang S, Willingham M C, Tooze J A, Dubey P. In situ vaccination combined with androgen ablation and regulatory T-cell depletion reduces castration-resistant tumor burden in prostate-specific pten knockout mice. Cancer Res. 2010; 70:3473-82.
12. Drake C G, Doody A D, Mihalyo M A, Huang C T, Kelleher E, Ravi S, et al. Androgen ablation mitigates tolerance to a prostate/prostate cancer-restricted antigen. Cancer cell. 2005; 7:239-49.
13. Koh Y T, Gray A, Higgins S A, Hubby B, Kast W M. Androgen ablation augments prostate cancer vaccine immunogenicity only when applied after immunization. Prostate. 2009.
14. Ardiani A, Farsaci B, Rogers C J, Protter A, Guo Z, King T H, et al. Combination therapy with a second-generation androgen receptor antagonist and a metastasis vaccine improves survival in a spontaneous prostate cancer model. Clin Cancer Res. 2013; 19:6205-18.
15. McNeel D G, Smith H A, Eickhoff J C, Lang J M, Staab M J, Wilding G, et al. Phase I trial of tremelimumab in combination with short-term androgen deprivation in patients with PSA-recurrent prostate cancer. Cancer Immunol Immunother. 2012; 61:1137-47.
16. Small E J, Lance R S, Gardner T A, Karsh L I, Fong L, McCoy C, et al. A Randomized Phase II Trial of Sipuleucel-T with Concurrent versus Sequential Abiraterone Acetate plus Prednisone in Metastatic Castration-Resistant Prostate Cancer. Clin Cancer Res. 2015; 21:3862-9.
17. Antonarakis E S, Kibel A S, Yu E Y, Karsh L I, Elfiky A, Shore N D, et al. Sequencing of Sipuleucel-T and Androgen Deprivation Therapy in Men with Hormone-Sensitive Biochemically-Recurrent Prostate Cancer: A Phase II Randomized Trial. Clin Cancer Res. 2016.
18. Madan R A, Gulley J L, Schlom J, Steinberg S M, Liewehr D J, Dahut W L, et al. Analysis of overall survival in patients with nonmetastatic castration-resistant prostate cancer treated with vaccine, nilutamide, and combination therapy. Clin Cancer Res. 2008; 14:4526-31.
19. Olson B M, McNeel D G. CD8+ T cells specific for the androgen receptor are common in patients with prostate cancer and are able to lyse prostate tumor cells. Cancer Immunol Immunother. 2011; 60:781-92.
20. Olson B M, Johnson L E, McNeel D G. The androgen receptor: a biologically relevant vaccine target for the treatment of prostate cancer. Cancer Immunol Immunother. 2013; 62:585-96.
21. Gregory C W, Hamil K G, Kim D, Hall S H, Pretlow T G, Mohler J L, et al. Androgen receptor expression in androgen-independent prostate cancer is associated with increased expression of androgen-regulated genes. Cancer Res. 1998; 58:5718-24.
22. Ellis L, Lehet K, Ramakrishnan S, Adelaiye R, Pili R. Development of a castrate resistant transplant tumor model of prostate cancer. Prostate. 2012; 72:587-91.
23. Wang S, Gao J, Lei Q, Rozengurt N, Pritchard C, Jiao J, et al. Prostate-specific deletion of the murine Pten tumor suppressor gene leads to metastatic prostate cancer. Cancer cell. 2003; 4:209-21.
24. Hornberg E, Ylitalo E B, Crnalic S, Antti H, Stattin P, Widmark A, et al. Expression of androgen receptor splice variants in prostate cancer bone metastases is associated with castration-resistance and short survival. PloS one. 2011; 6:e19059.
25. Watson P A, Chen Y F, Balbas M D, Wongvipat J, Socci N D, Viale A, et al. Constitutively active androgen receptor splice variants expressed in castration-resistant prostate cancer require full-length androgen receptor. Proc Natl Acad Sci USA. 2010; 107:16759-65.
26. Smith H A, Cronk R J, Lang J M, McNeel D G. Expression and Immunotherapeutic Targeting of the SSX Family of Cancer-Testis Antigens in Prostate Cancer. Cancer Res. 2011; 71:6785-95.
27. Fueger B J, Czernin J, Hildebrandt I, Tran C, Halpern B S, Stout D, et al. Impact of animal handling on the results of 18F-FDG PET studies in mice. J Nucl Med. 2006; 47:999-1006.
28. Disselhorst J A, Brom M, Laverman P, Slump C H, Boerman O C, Oyen W J, et al. Image-quality assessment for several positron emitters using the NEMA NU 4-2008 standards in the Siemens Inveon small-animal PET scanner. J Nucl Med. 2010; 51:610-7.

29. Valkenburg K C, Williams B O. Mouse models of prostate cancer. Prostate cancer. 2011; 2011:895238.
30. Weichert J P, Clark P A, Kandela I K, Vaccaro A M, Clarke W, Longino M A, et al. Alkylphosphocholine analogs for broad-spectrum cancer imaging and therapy. Science translational medicine. 2014; 6:240ra75.
31. Graff J N, Alumkal J J, Drake C G, Thomas G V, Redmond W L, Farhad M, et al. Early evidence of anti-PD-1 activity in enzalutamide-resistant prostate cancer. Oncotarget. 2016.
32. Pu Y, Xu M, Liang Y, Yang K, Guo Y, Yang X, et al. Androgen receptor antagonists compromise T cell response against prostate cancer leading to early tumor relapse. Science translational medicine. 2016; 8:333ra47.
33. Kissick H T, Sanda M G, Dunn L K, Pellegrini K L, On S T, Noel J K, et al. Androgens alter T-cell immunity by inhibiting T-helper 1 differentiation. Proc Natl Acad Sci USA. 2014; 111:9887-92.
34. Garnett C T, Palena C, Chakraborty M, Tsang K Y, Schlom J, Hodge J W. Sublethal irradiation of human tumor cells modulates phenotype resulting in enhanced killing by cytotoxic T lymphocytes. Cancer Res. 2004; 64:7985-94.
35. Gameiro S R, Jammeh M L, Wattenberg M M, Tsang K Y, Ferrone S, Hodge J W. Radiation-induced immunogenic modulation of tumor enhances antigen processing and calreticulin exposure, resulting in enhanced T-cell killing. Oncotarget. 2014; 5:403-16.
36. Chakraborty M, Abrams S I, Camphausen K, Liu K, Scott T, Coleman C N, et al. Irradiation of tumor cells up-regulates Fas and enhances CTL lytic activity and CTL adoptive immunotherapy. J Immunol. 2003; 170:6338-47.
37. Chakraborty M, Abrams S I, Coleman C N, Camphausen K, Schlom J, Hodge J W. External beam radiation of tumors alters phenotype of tumor cells to render them susceptible to vaccine-mediated T-cell killing. Cancer Res. 2004; 64:4328-37.
38. Harris T J, Hipkiss E L, Borzillary S, Wada S, Grosso J F, Yen H R, et al. Radiotherapy augments the immune response to prostate cancer in a time-dependent manner. Prostate. 2008; 68:1319-29.
39. Demaria S, Kawashima N, Yang A M, Devitt M L, Babb J S, Allison J P, et al. Immune-mediated inhibition of metastases after treatment with local radiation and CTLA-4 blockade in a mouse model of breast cancer. Clin Cancer Res. 2005; 11:728-34.
40. Golden E B, Chhabra A, Chachoua A, Adams S, Donach M, Fenton-Kerimian M, et al. Local radiotherapy and granulocyte-macrophage colony-stimulating factor to generate abscopal responses in patients with metastatic solid tumours: a proof-of-principle trial. The lancet oncology. 2015; 16:795-803.
41. Slovin S F, Higano C S, Hamid O, Tejwani S, Harzstark A, Alumkal J J, et al. Ipilimumab alone or in combination with radiotherapy in metastatic castration-resistant prostate cancer: results from an open-label, multicenter phase I/II study. Ann Oncol. 2013; 24:1813-21.
42. Spratt D E, Evans M J, Davis B J, Doran M G, Lee M X, Shah N, et al. Androgen Receptor Upregulation Mediates Radioresistance after Ionizing Radiation. Cancer Res. 2015; 75:4688-96.
43. Drake C G, Sharma P, Gerritsen W. Metastatic castration-resistant prostate cancer: new therapies, novel combination strategies and implications for immunotherapy. Oncogene. 2014; 33:5053-64.
44. Gan L, Chen S, Wang Y, Watahiki A, Bohrer L, Sun Z, et al. Inhibition of the androgen receptor as a novel mechanism of taxol chemotherapy in prostate cancer. Cancer Res. 2009; 69:8386-94.
45. Zhu M L, Horbinski C M, Garzotto M, Qian D Z, Beer T M, Kyprianou N. Tubulin-targeting chemotherapy impairs androgen receptor activity in prostate cancer. Cancer Res. 2010; 70:7992-8002.
46. Sweeney C J, Chen Y H, Carducci M, Liu G, Jarrard D F, Eisenberger M, et al. Chemohormonal Therapy in Metastatic Hormone-Sensitive Prostate Cancer. The New England journal of medicine. 2015; 373:737-46.
47. Rowe S P, Macura K J, Mena E, Blackford A L, Nadal R, Antonarakis E S, et al. PSMA-Based [(18)F]DCFPyL PET/C T Is Superior to Conventional Imaging for Lesion Detection in Patients with Metastatic Prostate Cancer. Molecular imaging and biology: MIB: the official publication of the Academy of Molecular Imaging. 2016; 18:411-9.
48. Beattie B J, Smith-Jones P M, Jhanwar Y S, Schoder H, Schmidtlein C R, Morris M J, et al. Pharmacokinetic assessment of the uptake of 16beta-18F-fluoro-5alpha-dihydrotestosterone (FDHT) in prostate tumors as measured by PET. J Nucl Med. 2010; 51:183-92.
49. Antonarakis E S, Lu C, Wang H, Luber B, Nakazawa M, Roeser J C, et al. A R-V7 and resistance to enzalutamide and abiraterone in prostate cancer. N Engl J Med. 2014; 371:1028-38.
50. Yu Z, Chen S, Sowalsky A G, Voznesensky O S, Mostaghel E A, Nelson P S, et al. Rapid induction of androgen receptor splice variants by androgen deprivation in prostate cancer. Clin Cancer Res. 2014; 20:1590-600.

This specification includes the sequence listing that is concurrently filed in computer readable form. This sequence listing is incorporated by reference herein.

We claim:

1. A method of eliciting an anti-tumor response in a subject having prostate cancer comprising:
   a. administering to the subject androgen deprivation therapy (ADT) comprising degarelix; and
   b. administering to the subject a recombinant DNA vaccine comprising a polynucleotide operably linked to a transcriptional regulatory element wherein the polynucleotide encodes an androgen receptor or a fragment of the androgen receptor selected from the group consisting of (i) a mammalian androgen receptor, (ii) a fragment of the androgen receptor that comprises a ligand-binding domain, (iii) a fragment of the ligand-binding domain defined by SEQ ID NO:9, (iv) a fragment of the ligand-binding domain defined by SEQ ID NO:10, (v) a fragment of the ligand-binding domain defined by SEQ ID NO:11, and (vi) a fragment of the ligand-binding domain defined by SEQ ID NO:12, whereby the DNA vaccine elicits an immune response in the subject against the androgen receptor,
   wherein the recombinant DNA vaccine is administered in an amount effective to elicit an increased anti-tumor response to the prostate cancer, wherein the combination treatment of ADT and the recombinant DNA vaccine inhibits, delays or reduces the growth of the prostate cancer.

2. The method of claim 1, wherein the DNA vaccine comprises the polynucleotide that encodes a fragment of the androgen receptor ligand binding fragment.

3. The method of claim 1, wherein the DNA vaccine is administered every two weeks to every three months.

4. The method of claim 1, wherein the DNA vaccine is administered biweekly for about 6 to about 10 weeks and subsequently administered quarterly for at least a year.

5. The method of claim 1, wherein the vaccine is administered in a dosage of about 10 mcg to 1 mg.

6. The method of claim 1, wherein the ADT and recombinant vaccine are administered concurrently.

7. The method of claim 1, wherein the ADT is administered before administering the recombinant vaccine.

8. The method of claim 1, wherein the ADT is administered after administering at least one dosage of the recombinant vaccine.

9. The method of claim 1, wherein the DNA vaccine is administered intradermally, intramuscularly, subcutaneously, intravenously or intra-arterially, with or without electroporation.

10. The method of claim 1, wherein the DNA vaccine comprises pTVG-ARLBD.

11. The method of claim 1, wherein the method further comprises administering to the subject an effective amount of a PD-pathway inhibitor.

12. The method of claim 1, wherein the prostate cancer is castration resistant prostate cancer (mCRPC).

13. The method of claim 1, wherein the prostate cancer is recurrent or metastatic prostate cancer.

14. A method of eliciting an anti-tumor response in a subject having prostate cancer comprising:
   a. administering to the subject androgen deprivation therapy (ADT) comprising degarelix;
   b. administering to the subject a recombinant DNA vaccine comprising a polynucleotide operably linked to a transcriptional regulatory element wherein the polynucleotide encodes an androgen receptor or a fragment of the androgen receptor selected from the group consisting of (i) a mammalian androgen receptor, (ii) a fragment of the androgen receptor that comprises a ligand-binding domain, (iii) a fragment of the ligand-binding domain defined by SEQ ID NO:9, (iv) a fragment of the ligand-binding domain defined by SEQ ID NO:10, (v) a fragment of the ligand-binding domain defined by SEQ ID NO:11, and (vi) a fragment of the ligand-binding domain defined by SEQ ID NO:12, whereby the DNA vaccine elicits an immune response in the subject against the androgen receptor, and
   c. administering to the subject an effective amount of a PD-pathway inhibitor,
   wherein the recombinant DNA vaccine and PD-pathway inhibitor are administered in an amount effective to elicit an increased anti-tumor response to the prostate cancer, wherein the combination treatment of ADT, the recombinant DNA vaccine and PD-pathway inhibitor inhibits, delays or reduces the growth of the prostate cancer.

15. The method of claim 14, wherein the DNA vaccine comprises the polynucleotide that encodes a fragment of the androgen receptor ligand binding fragment.

16. The method of claim 14, wherein the DNA vaccine is administered every two weeks to every three months.

17. The method of claim 14, wherein the DNA vaccine is administered biweekly for about 6 to about 10 weeks and subsequently administered quarterly for at least a year.

18. The method of claim 14, wherein the vaccine is administered in a dosage of about 10 mcg to 1 mg.

19. The method of claim 14, wherein the DNA vaccine comprises pTVG-ARLBD.

* * * * *

UNITED STATES PATENT AND TRADEMARK OFFICE
CERTIFICATE OF CORRECTION

PATENT NO. : 10,881,719 B2
APPLICATION NO. : 15/619140
DATED : January 5, 2021
INVENTOR(S) : Douglas McNeel et al.

It is certified that error appears in the above-identified patent and that said Letters Patent is hereby corrected as shown below:

In the Specification

Column 2, Line 9, "MEW" should be --MHC--.

Column 11, Line 10, "Amon" should be --Arnon--.

Column 21, Line 40, "foxed" should be --floxed--.

Column 32, Line 6, "H2504" should be --$H_2SO_4$--.

Signed and Sealed this
Ninth Day of March, 2021

Drew Hirshfeld
*Performing the Functions and Duties of the*
*Under Secretary of Commerce for Intellectual Property and*
*Director of the United States Patent and Trademark Office*